US007732569B2

(12) United States Patent
Decarolis et al.

(10) Patent No.: US 7,732,569 B2
(45) Date of Patent: Jun. 8, 2010

(54) ZEIN-BASED PEPTIDE TAGS FOR THE EXPRESSION AND PURIFICATION OF BIOACTIVE PEPTIDES

(75) Inventors: Linda Jane Decarolis, Wilmington, DE (US); Stephen R. Fahnestock, Wilmington, DE (US); Hong Wang, Kennett Square, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 429 days.

(21) Appl. No.: 11/641,936

(22) Filed: Dec. 19, 2006

(65) Prior Publication Data
US 2008/0096246 A1 Apr. 24, 2008

Related U.S. Application Data

(60) Provisional application No. 60/852,838, filed on Oct. 19, 2006.

(51) Int. Cl.
C07K 1/00 (2006.01)
(52) U.S. Cl. ..................................... 530/350
(58) Field of Classification Search ................ 530/350; 435/69.1, 252.3, 320.1
See application file for complete search history.

(56) References Cited

U.S. PATENT DOCUMENTS

| 4,870,023 | A | 9/1989 | Fraser et al. |
|---|---|---|---|
| 5,110,729 | A | 5/1992 | Maeda et al. |
| 5,206,154 | A | 4/1993 | Lai et al. |
| 5,215,896 | A | 6/1993 | Keck et al. |
| 5,223,409 | A | 6/1993 | Ladner et al. |
| 5,302,526 | A | 4/1994 | Keck et al. |
| 5,330,902 | A | 7/1994 | Keck et al. |
| 5,403,484 | A | 4/1995 | Ladner et al. |
| 5,449,754 | A | 9/1995 | Nishioka et al. |
| 5,480,971 | A | 1/1996 | Houghten et al. |
| 5,571,698 | A | 11/1996 | Ladner et al. |
| 5,585,275 | A | 12/1996 | Hudson et al. |
| 5,639,603 | A | 6/1997 | Dower et al. |
| 5,648,244 | A | 7/1997 | Kuliopulos et al. |
| 5,670,340 | A | 9/1997 | Yabuta et al. |
| 5,837,500 | A | 11/1998 | Ladner et al. |
| 6,037,145 | A | 3/2000 | Yabuta et al. |
| 6,242,219 | B1 | 6/2001 | Better et al. |
| 6,613,548 | B1 | 9/2003 | Chu |
| 6,620,419 | B1 | 9/2003 | Lintner |
| 6,699,689 | B1 | 3/2004 | Kim et al. |
| 2003/0152976 | A1 | 8/2003 | Janssen et al. |
| 2003/0185870 | A1 | 10/2003 | Grinstaff et al. |
| 2004/0142492 | A1 | 7/2004 | Kiesewetter et al. |
| 2005/0221444 | A1 | 10/2005 | Williams et al. |
| 2007/0243198 | A1* | 10/2007 | Heifetz et al. ............ 424/184.1 |

FOREIGN PATENT DOCUMENTS

| WO | WO 94/04688 | A2 | 3/1994 |
|---|---|---|---|
| WO | WO 03/100021 | A2 | 12/2003 |
| WO | WO 2004/003207 | * | 1/2004 |

OTHER PUBLICATIONS

U.S. Appl. No. 10/935,642, filed Mar. 10, 2005, Xueying Huang et al.
U.S. Appl. No. 10/935,254, filed Mar. 10, 2005, John P. O'Brien et al.
D.J. Kemp, Direct Immunoassay for Detecting *Escherichia coli* Colonies that Contain Polypeptides Encoded by Cloned DNA Segments, Proc. Natl. Acad. Sci., 1981, vol. 78:4520-4524.
Chien et. al., The Two-Hybird System: A Method to Identify and Clone Genes for Proteins that Interact With a Protein of Interest, Proc. Natl. Acad. Sci., 1991, vol. 88:9578-9582.
Dykes et. al., Expression of Atrial Natriuretic Factor as a Cleavable Fusion Protein With Chloramphenicol Acetyltransferase in *Escherichia coli*, Eur. J. Biochem., 1988, vol. 174:411-416.
Schellenberger et. al., Peptide Production by a Combination of Gene Expression, Chemical Syntheisis, and Protease-Catalyzed Conversion, Int. J. Peptide Protein Res., 1993, vol. 41:326-332.
Shen et. al., Multiple Joined Genes Prevent Product Degradation in *Escherichia coli*, Proc. Natl. Acad. Sci., 1984, vol. 281:4627-4631.
Kempe et. al., Multiple-Copy Genes: Production and Modification of Monomeric Peptides From Large Multimeric Fusion Proteins, Gene, 1985, vol. 39:239-245.
Ray et. al., Production of Recombinant Salmon Calcitonin by In Vitro Amidation of an *Escherichia coli* Produced Precursor Peptide, Bio/Technology, 1993, vol. 11:64-70.
Gram et. al., A Novel Approach for High Level Production of a Recombinant Human Parathyroid Hormone Fragment in *Escherichia coli*, Bio/Technology, 1994, vol. 12:1017-1023.
Kuliopulos et. al., Production, Purification, and Cleavage of Tandem Repeats of Recombinant Peptides, J. Am. Chem. Soc., 1994, vol. 116:4599-4607.
Pilon et. al., Ubiquitin Fusion Technology: Bioprocessing of Peptides, Biotechnol. Prog., 1997, vol. 13:374-379.
Haught et. al., Recombinat Production and Purification of Novel Antisense Antimicrobial Peptide in *Escherichia coli*, Biotechnol. Bioengineer., 1988, vol. 57:55-61.

* cited by examiner

*Primary Examiner*—Maryam Monshipouri

(57) ABSTRACT

Zein-based peptide tags, referred to here as inclusion body tags (IBTs), are disclosed useful for the generation of insoluble fusion peptides. The fusion peptides comprise at least one inclusion body tag operably linked to a peptide of interest. Expression of the fusion peptide in a host cell results in a product that is insoluble and contained within inclusion bodies in the cell and/or cell lysate. The inclusion bodies may then be purified and the protein of interest may be isolated after cleavage from the inclusion body tag.

4 Claims, No Drawings

SEQUENCE LISTING

<160> NUMBER OF SEQ ID NOS: 445

<210> SEQ ID NO 1
<211> LENGTH: 672
<212> TYPE: DNA
<213> ORGANISM: Zea mays

<400> SEQUENCE: 1

| | | | | | |
|---|---|---|---|---|---|
| atgagggtgt | tgctcgttgc | cctcgctctc | ctggctctcg | ctgcgagcgc | cacctccacg | 60 |
| catacaagcg | gcggctgcgg | ctgccagcca | ccgccgccgg | ttcatctacc | gccgccggtg | 120 |
| catctgccac | ctccggttca | cctgccacct | ccggtgcatc | tcccaccgcc | ggtccacctg | 180 |
| ccgccgccgg | tccacctgcc | accgccggtc | catgtgccgc | cgccggttca | tctgccgccg | 240 |
| ccaccatgcc | actaccctac | tcaaccgccc | ggcctcagc | ctcatcccca | gccacaccca | 300 |
| tgcccgtgcc | aacagccgca | tccaagcccg | tgccagctgc | agggaacctg | cggcgttggc | 360 |
| agcaccccga | tcctgggcca | gtgcgtcgag | ttcctgaggc | atcagtgcag | cccgacggcg | 420 |
| acgccctact | gctcgcctca | gtgccagtcg | ttgcggcagc | agtgttgcca | gcagctcagg | 480 |
| caggtggagc | cgcagcaccg | gtaccaggcg | atcttcggct | tggtcctcca | gtccatcctg | 540 |
| cagcagcagc | cgcaaagcgg | ccaggtcgcg | gggctgttgg | cggcgcagat | agcgcagcaa | 600 |
| ctgacggcga | tgtgcggcct | gcagcagccg | actccatgcc | cctacgctgc | tgccggcggt | 660 |
| gtcccccact | ga | | | | | 672 |

<210> SEQ ID NO 2
<211> LENGTH: 223
<212> TYPE: PRT
<213> ORGANISM: Zea mays

<400> SEQUENCE: 2

Met Arg Val Leu Leu Val Ala Leu Ala Leu Ala Leu Ala Ala Ser
1               5                   10                  15

Ala Thr Ser Thr His Thr Ser Gly Gly Cys Gly Cys Gln Pro Pro
            20                  25                  30

Pro Val His Leu Pro Pro Val His Leu Pro Pro Val His Leu
            35                  40                  45

Pro Pro Val His Leu Pro Pro Val His Leu Pro Pro Val
        50                  55                  60

His Leu Pro Pro Val His Val Pro Pro Val His Leu Pro Pro
65                  70                  75                  80

Pro Pro Cys His Tyr Pro Thr Gln Pro Arg Pro Gln Pro His Pro
                85                  90                  95

Gln Pro His Pro Cys Pro Cys Gln Gln Pro His Pro Ser Pro Cys Gln
            100                 105                 110

Leu Gln Gly Thr Cys Gly Val Gly Ser Thr Pro Ile Leu Gly Gln Cys
            115                 120                 125

Val Glu Phe Leu Arg His Gln Cys Ser Pro Thr Ala Thr Pro Tyr Cys
            130                 135                 140

Ser Pro Gln Cys Gln Ser Leu Arg Gln Cys Cys Gln Gln Leu Arg
145                 150                 155                 160

Gln Val Glu Pro Gln His Arg Tyr Gln Ala Ile Phe Gly Leu Val Leu
                165                 170                 175

Gln Ser Ile Leu Gln Gln Gln Pro Gln Ser Gly Gln Val Ala Gly Leu
            180                 185                 190

Leu Ala Ala Gln Ile Ala Gln Gln Leu Thr Ala Met Cys Gly Leu Gln
        195                 200                 205

Gln Pro Thr Pro Cys Pro Tyr Ala Ala Ala Gly Gly Val Pro His
    210                 215                 220

<210> SEQ ID NO 3
<211> LENGTH: 195
<212> TYPE: DNA
<213> ORGANISM: artificial sequence
<220> FEATURE:
<223> OTHER INFORMATION: Synthetic gene

<400> SEQUENCE: 3
ggtcgtttcc acgaaaactg gccgtctggt ggcggtacct ctacttccaa agcttccacc      60
actacgactt ctagcaaaac caccactaca tcctctaaga ctaccacgac tacctccaaa     120
acctctacta cctctagctc ctctacgggc ggtggcactc acaagacctc tactcagcgt     180
ctgctggctg cataa                                                     195

<210> SEQ ID NO 4
<211> LENGTH: 68
<212> TYPE: PRT
<213> ORGANISM: artificial sequence
<220> FEATURE:
<223> OTHER INFORMATION: Synthetic triblock peptide

<400> SEQUENCE: 4

Gly Ser Ile Glu Gly Arg Phe His Glu Asn Trp Pro Ser Ala Gly Gly
1               5                   10                  15

Thr Ser Thr Ser Lys Ala Ser Thr Thr Thr Thr Ser Ser Lys Thr Thr
            20                  25                  30

Thr Thr Ser Ser Lys Thr Thr Thr Thr Thr Ser Lys Thr Ser Thr Thr
        35                  40                  45

Ser Ser Ser Ser Thr Gly Gly Ala Thr His Lys Thr Ser Thr Gln Arg
    50                  55                  60

Leu Leu Ala Ala
65

<210> SEQ ID NO 5
<211> LENGTH: 103
<212> TYPE: DNA
<213> ORGANISM: artificial sequence
<220> FEATURE:
<223> OTHER INFORMATION: oligo used to prepare TBP101

<400> SEQUENCE: 5
ggatccatcg aaggtcgttt ccacgaaaac tggccgtctg gtggcggtac ctctacttcc      60
aaagcttcca ccactacgac ttctagcaaa accaccacta cat                      103

<210> SEQ ID NO 6
<211> LENGTH: 104
<212> TYPE: DNA
<213> ORGANISM: artificial sequence
<220> FEATURE:
<223> OTHER INFORMATION: oligo used to prepare TBP101

<400> SEQUENCE: 6
cctctaagac taccacgact acctccaaaa cctctactac ctctagctcc tctacgggcg      60
gtggcactca caagacctct actcagcgtc tgctggctgc ataa                     104

<210> SEQ ID NO 7
<211> LENGTH: 69
<212> TYPE: DNA
<213> ORGANISM: artificial sequence
<220> FEATURE:
<223> OTHER INFORMATION: oligo used to prepare TBP101

<400> SEQUENCE: 7
ttatgcagcc agcagacgct gagtagaggt cttgtgagtg ccaccgcccg tagaggagct    60
agaggtagt                                                            69

<210> SEQ ID NO 8
<211> LENGTH: 69
<212> TYPE: DNA
<213> ORGANISM: artificial sequence
<220> FEATURE:
<223> OTHER INFORMATION: oligo used to prepare TBP101

<400> SEQUENCE: 8
agaggttttg gaggtagtcg tggtagtctt agaggatgta gtggtggttt tgctagaagt    60
cgtagtggt                                                            69

<210> SEQ ID NO 9
<211> LENGTH: 69
<212> TYPE: DNA
<213> ORGANISM: artificial sequence
<220> FEATURE:
<223> OTHER INFORMATION: oligo used to prepare TBP101

<400> SEQUENCE: 9
ggaagctttg gaagtagagg taccgccacc agacggccag ttttcgtgga aacgaccttc    60
gatggatcc                                                            69

<210> SEQ ID NO 10
<211> LENGTH: 22
<212> TYPE: DNA
<213> ORGANISM: artificial sequence
<220> FEATURE:
<223> OTHER INFORMATION: Primer

<400> SEQUENCE: 10
caccggatcc atcgaaggtc gt                                             22

<210> SEQ ID NO 11
<211> LENGTH: 21
<212> TYPE: DNA
<213> ORGANISM: artificial sequence
<220> FEATURE:
<223> OTHER INFORMATION: Primer

<400> SEQUENCE: 11
tcattatgca gccagcagcg c                                              21

<210> SEQ ID NO 12
<211> LENGTH: 2580
<212> TYPE: DNA
<213> ORGANISM: artificial sequence
<220> FEATURE:
<223> OTHER INFORMATION: Plasmid

<400> SEQUENCE: 12
ctttcctgcg ttatcccctg attctgtgga taaccgtatt accgcctttg agtgagctga    60
taccgctcgc cgcagccgaa cgaccgagcg cagcgagtca gtgagcgagg aagcggaaga   120

```
gcgcccaata cgcaaaccgc ctctccccgc gcgttggccg attcattaat gcagctggca    180
cgacaggttt cccgactgga aagcgggcag tgagcgcaac gcaattaata cgcgtaccgc    240
tagccaggaa gagtttgtag aaacgcaaaa aggccatccg tcaggatggc cttctgctta    300
gtttgatgcc tggcagttta tggcgggcgt cctgcccgcc accctccggg ccgttgcttc    360
acaacgttca atccgctcc cggcggattt gtcctactca ggagagcgtt caccgacaaa    420
caacagataa aacgaaaggc ccagtcttcc gactgagcct tcgttttat ttgatgcctg    480 gcagttccct actctcgcgt taacgctagc atggatgttt cccagtcac gacgttgtaa    540 aacgacggcc agtcttaagc tcgggcccca ataatgatt ttattttgac tgatagtgac    600
ctgttcgttg caacaaattg atgagcaatg ctttttata atgccaactt tgtacaaaaa    660
agcaggctcc gcggccgccc ccttcaccaa gggtgggcgc gccgacccag ctttcttgta    720
caaagttggc attataagaa agcattgctt atcaatttgt tgcaacgaac aggtcactat    780
cagtcaaaat aaaatcatta tttgccatcc agctgatatc ccctatagtg agtcgtatta    840
catggtcata gctgtttcct ggcagctctg gcccgtgtct caaaatctct gatgttacat    900
tgcacaagat aaaaatatat catcatgaac aataaaactg tctgcttaca taaacagtaa    960
tacaaggggt gttatgagcc atattcaacg ggaaacgtcg aggccgcgat taaattccaa   1020
catggatgct gatttatatg ggtataaatg ggctcgcgat aatgtcgggc aatcaggtgc   1080
gacaatctat cgcttgtatg ggaagcccga tgcgccagag ttgtttctga acatggcaa   1140 aggtagcgtt gccaatgatg ttacagatga gatggtcaga ctaaactggc tgacggaatt   1200
tatgcctctt ccgaccatca agcatttat ccgtactcct gatgatgcat ggttactcac   1260
cactgcgatc cccggaaaaa cagcattcca ggtattagaa gaatatcctg attcaggtga   1320
aaatattgtt gatgcgctgg cagtgttcct gcgccggttg cattcgattc ctgtttgtaa   1380
ttgtcctttt aacagcgatc gcgtatttcg tctcgctcag gcgcaatcac gaatgaataa   1440
cggtttggtt gatgcgagtg attttgatga cgagcgtaat ggctggcctg ttgaacaagt   1500
ctggaaagaa atgcataaac ttttgccatt ctcaccggat tcagtcgtca ctcatggtga   1560
tttctcactt gataaccta ttttttgacga ggggaaatta ataggttgta ttgatgttgg   1620
acgagtcgga atcgcagacc gataccagga tcttgccatc ctatggaact gcctcggtga   1680
gttttctcct tcattacaga aacggctttt tcaaaaatat ggtattgata atcctgatat   1740
gaataaattg cagtttcatt tgatgctcga tgagttttc taatcagaat tggttaattg   1800
gttgtaacac tggcagagca ttacgctgac ttgacggac ggcgcaagct catgaccaaa   1860
atcccttaac gtgagttacg cgtcgttcca ctgagcgtca daccccgtag aaaagatcaa   1920
aggatcttct tgagatcctt ttttttctgcg cgtaatctgc tgcttgcaaa caaaaaaacc   1980
accgctacca gcggtggttt gtttgccgga tcaagagcta ccaactcttt ttccgaaggt   2040
aactggcttc agcagagcgc agataccaaa tactgtcctt ctagtgtagc cgtagttagg   2100
ccaccacttc aagaactctg tagcaccgcc tacatacctc gctctgctaa tcctgttacc   2160
agtggctgct gccagtggcg ataagtcgtg tcttaccggg ttggactcaa gacgatagtt   2220
accggataag gcgcagcggt cgggctgaac ggggggttcg tgcacacagc ccagcttgga   2280
gcgaacgacc tacaccgaac tgagatacct acagcgtgag cattgagaaa gcgccacgct   2340
tcccgaaggg agaaaggcgg acaggtatcc ggtaagcggc agggtcggaa caggagagcg   2400
cacgagggag cttccagggg gaaacgcctg gtatctttat agtcctgtcg gtttcgcca   2460 cctctgactt gagcgtcgat ttttgtgatg ctcgtcaggg gggcggagcc tatggaaaaa   2520
```

-continued

```
cgccagcaac gcggccttttt tacggttcct ggccttttgc tggccttttg ctcacatgtt    2580
```

<210> SEQ ID NO 13
<211> LENGTH: 6354
<212> TYPE: DNA
<213> ORGANISM: artificial sequence
<220> FEATURE:
<223> OTHER INFORMATION: Plasmid

<400> SEQUENCE: 13

```
agatctcgat cccgcgaaat taatacgact cactataggg agaccacaac ggtttccctc      60
tagaaataat tttgtttaac tttaagaagg agatatacat atgtcgtact accatcacca    120
tcaccatcac ctcgaatcaa caagtttgta caaaaaagct gaacgagaaa cgtaaaatga    180
tataaatatc aatatattaa attagatttt gcataaaaaa cagactacat aatactgtaa    240
aacacaacat atccagtcac tatggcggcc gcattaggca ccccaggctt tacactttat    300
gcttccggct cgtataatgt gtggattttg agttaggatc cgtcgagatt ttcaggagct    360
aaggaagcta aaatggagaa aaaaatcact ggatatacca ccgttgatat atcccaatgg    420
catcgtaaag aacattttga ggcatttcag tcagttgctc aatgtaccta taaccagacc    480
gttcagctgg atattacggc cttttttaaag accgtaaaga aaaataagca caagttttat    540
ccggccttta ttcacattct tgcccgcctg atgaatgctc atccggaatt ccgtatggca    600
atgaaagacg gtgagctggt gatatgggat agtgttcacc cttgttacac cgttttccat    660
gagcaaactg aaacgttttc atcgctctgg agtgaatacc acgacgattt ccggcagttt    720
ctacacatat attcgcaaga tgtggcgtgt tacggtgaaa acctggccta tttccctaaa    780
gggtttattg agaatatgtt tttcgtctca gccaatccct gggtgagttt caccagtttt    840
gatttaaacg tggccaatat ggacaacttc ttcgcccccg ttttcaccat gggcaaatat    900
tatacgcaag cgacaaggt gctgatgccg ctggcgattc aggttcatca tgccgtctgt    960
gatggcttcc atgtcggcag aatgcttaat gaattacaac agtactgcga tgagtggcag   1020
ggcggggcgt aaagatctgg atccggctta ctaaaagcca gataacagta tgcgtatttg   1080
cgcgctgatt tttgcggtat aagaatatat actgatatgt atacccgaag tatgtcaaaa   1140
agaggtgtgc tatgaagcag cgtattacag tgacagttga cagcgacagc tatcagttgc   1200
tcaaggcata tgatgtcaa atatctccgg tctggtaagc acaaccatgc agaatgaagc   1260
ccgtcgtctg cgtgccgaac gctggaaagc ggaaaatcag aagggatgg ctgaggtcgc   1320
ccggtttatt gaaatgaacg gctcttttgc tgacgagaac agggactggt gaaatgcagt   1380
ttaaggttta cacctataaa agagagagcc gttatcgtct gtttgtggat gtacagagtg   1440
atattattga cacgcccggg cgacggatgg tgatcccct ggccagtgca cgtctgctgt   1500
cagataaagt ctcccgtgaa ctttacccgg tggtgcatat cggggatgaa agctggcgca   1560
tgatgaccac cgatatggcc agtgtgccgg tctccgttat cggggaagaa gtggctgatc   1620
tcagccaccg cgaaaatgac atcaaaaacg ccattaacct gatgttctgg ggaatataaa   1680
tgtcaggctc ccttatacac agccagtctg caggtcgacc atagtgactg gatatgttgt   1740
gttttacagt attatgtagt ctgttttttta tgcaaaatct aatttaatat attgatattt   1800
atatcatttt acgtttctcg ttcagctttc ttgtacaaag tggttgattc gaggctgcta   1860
acaaagcccg aaaggaagct gagttggctg ctgccaccgc tgagcaataa ctagcataac   1920
cccttggggc ctctaaacgg gtcttgaggg gttttttgct gaaaggagga actatatccg   1980
```

-continued

```
gatatccaca ggacgggtgt ggtcgccatg atcgcgtagt cgatagtggc tccaagtagc    2040
gaagcgagca ggactgggcg gcggccaaag cggtcggaca gtgctccgag aacgggtgcg    2100
catagaaatt gcatcaacgc atatagcgct agcagcacgc catagtgact ggcgatgctg    2160
tcggaatgga cgatatcccg caagaggccc ggcagtaccg gcataaccaa gcctatgcct    2220
acagcatcca gggtgacggt gccgaggatg acgatgagcg cattgttaga tttcatacac    2280
ggtgcctgac tgcgttagca atttaactgt gataaactac cgcattaaag cttatcgatg    2340
ataagctgtc aaacatgaga attcttgaag acgaaagggc ctcgtgatac gcctattttt    2400
ataggttaat gtcatgataa taatggtttc ttagacgtca ggtggcactt ttcggggaaa    2460
tgtgcgcgga accccatttt gtttattttt ctaaatacat tcaaatatgt atccgctcat    2520
gagacaataa ccctgataaa tgcttcaata atattgaaaa aggaagagta tgagtattca    2580
acatttccgt gtcgccctta ttcccttttt tgcggcattt tgccttcctg ttttgctca    2640 cccagaaacg ctggtgaaag taaaagatgc tgaagatcag ttgggtgcac gagtgggtta    2700
catcgaactg gatctcaaca gcggtaagat ccttgagagt tttcgccccg aagaacgttt    2760
tccaatgatg agcactttta aagttctgct atgtggcgcg gtattatccc gtgttgacgc    2820
cgggcaagag caactcggtc gccgcataca ctattctcag aatgacttgg ttgagtactc    2880
accagtcaca gaaaagcatc ttacggatgg catgacagta agagaattat gcagtgctgc    2940
cataaccatg agtgataaca ctgcggccaa cttacttctg acaacgatcg gaggaccgaa    3000
ggagctaacc gcttttttgc acaacatggg ggatcatgta actcgccttg atcgttggga    3060
accggagctg aatgaagcca taccaaacga cgagcgtgac accacgatgc ctgcagcaat    3120
ggcaacaacg ttgcgcaaac tattaactgg cgaactactt actctagctt cccggcaaca    3180
attaatagac tggatggagg cggataaagt tgcaggacca cttctgcgct cggcccttcc    3240
ggctggctgg tttattgctg ataaatctgg agccggtgag cgtgggtctc gcggtatcat    3300
tgcagcactg gggccagatg gtaagccctc ccgtatcgta gttatctaca cgacggggag    3360
tcaggcaact atggatgaac gaaatagaca gatcgctgag ataggtgcct cactgattaa    3420
gcattggtaa ctgtcagacc aagtttactc atatatactt tagattgatt taaaacttca    3480
tttttaattt aaaaggatct aggtgaagat cctttttgat aatctcatga ccaaaatccc    3540
ttaacgtgag ttttcgttcc actgagcgtc agaccccgta gaaaagatca aggatcttc    3600 ttgagatcct ttttttctgc gcgtaatctg ctgcttgcaa acaaaaaaac caccgctacc    3660
agcggtggtt tgtttgccgg atcaagagct accaactctt tttccgaagg taactggctt    3720
cagcagagcg cagataccaa atactgtcct tctagtgtag ccgtagttag gccaccactt    3780
caagaactct gtagcaccgc ctacatacct cgctctgcta atcctgttac cagtggctgc    3840
tgccagtggc gataagtcgt gtcttaccgg gttggactca agacgatagt taccggataa    3900
ggcgcagcgg tcgggctgaa cggggggttc gtgcacacag cccagcttgg agcgaacgac    3960
ctacaccgaa ctgagatacc tacagcgtga gctatgagaa agcgccacgc ttcccgaagg    4020
gagaaaggcg gacaggtatc cggtaagcgg cagggtcgga acaggagagc gcacgaggga    4080
gcttccaggg ggaaacgcct ggtatcttta tagtcctgtc gggtttcgcc acctctgact    4140
tgagcgtcga tttttgtgat gctcgtcagg gggcggagc ctatggaaaa acgccagcaa    4200
cgcggccttt ttacggttcc tggccttttg ctggcctttt gctcacatgt tctttcctgc    4260
gttatcccct gattctgtgg ataaccgtat taccgccttt gagtgagctg ataccgctcg    4320
ccgcagccga acgaccgagc gcagcgagtc agtgagcgag gaagcggaag agcgcctgat    4380
```

```
gcggtatttt ctccttacgc atctgtgcgg tatttcacac cgcatatatg gtgcactctc    4440
agtacaatct gctctgatgc cgcatagtta agccagtata cactccgcta tcgctacgtg    4500
actgggtcat ggctgcgccc cgacacccgc caacacccgc tgacgcgccc tgacgggctt    4560
gtctgctccc ggcatccgct tacagacaag ctgtgaccgt ctccgggagc tgcatgtgtc    4620
agaggttttc accgtcatca ccgaaacgcg cgaggcagct gcggtaaagc tcatcagcgt    4680
ggtcgtgaag cgattcacag atgtctgcct gttcatccgc gtccagctcg ttgagtttct    4740
ccagaagcgt taatgtctgg cttctgataa agcgggccat gttaagggcg ttttttcct     4800 gtttggtcac tgatgcctcc gtgtaagggg gatttctgtt catggggta atgataccga      4860 tgaaacgaga gaggatgctc acgatacggg ttactgatga tgaacatgcc cggttactgg    4920
aacgttgtga gggtaaacaa ctggcggtat ggatgcggcg ggaccagaga aaaatcactc    4980
agggtcaatg ccagcgcttc gttaatacag atgtaggtgt tccacagggt agccagcagc    5040
atcctgcgat gcagatccgg aacataatgg tgcagggcgc tgacttccgc gtttccagac    5100
tttacgaaac acgaaaaccg aagaccattc atgttgttgc tcaggtcgca gacgttttgc    5160
agcagcagtc gcttcacgtt cgctcgcgta tcggtgattc attctgctaa ccagtaaggc    5220
aaccccgcca gcctagccgg gtcctcaacg acaggagcac gatcatgcgc acccgtggcc    5280
aggacccaac gctgcccgag atgcgccgcg tgcggctgct ggagatggcg gacgcgatgg    5340
atatgttctg ccaagggttg gtttgcgcat tcacagttct ccgcaagaat tgattggctc    5400
caattcttgg agtggtgaat ccgttagcga ggtgccgccg gcttccattc aggtcgaggt    5460
ggcccggctc catgcaccgc gacgcaacgc ggggaggcag acaaggtata gggcggcgcc    5520
tacaatccat gccaacccgt tccatgtgct cgccgaggcg gcataaatcg ccgtgacgat    5580
cagcggtcca gtgatcgaag ttaggctggt aagagccgcg agcgatcctt gaagctgtcc    5640
ctgatggtcg tcatctacct gcctggacag catggcctgc aacgcgggca tcccgatgcc    5700
gccggaagcg agaagaatca taatgggaa ggccatccag cctcgcgtcg cgaacgccag    5760
caagacgtag cccagcgcgt cggccgccat gccggcgata atggcctgct tctcgccgaa    5820
acgtttggtg gcgggaccag tgacgaaggc ttgagcgagg gcgtgcaaga ttccgaatac    5880
cgcaagcgac aggccgatca tcgtcgcgct ccagcgaaag cggtcctcgc cgaaaatgac    5940
ccagagcgct gccggcacct gtcctacgag ttgcatgata agaagacag tcataagtgc      6000 ggcgacgata gtcatgcccc gcgcccaccg gaaggagctg actgggttga aggctctcaa    6060
gggcatcggt cgatcgacgc tctcccttat gcgactcctg cattaggaag cagcccagta    6120
gtaggttgag gccgttgagc accgccgccg caaggaatgg tgcatgcaag agatggcgc     6180 ccaacagtcc cccggccacg gggcctgcca ccatacccac gccgaaacaa gcgctcatga    6240
gcccgaagtg gcgagcccga tcttccccat cggtgatgtc ggcgatatag cgccagcaa     6300 ccgcacctgt ggcgccggtg atgccggcca cgatgcgtcc ggcgtagagg atcg          6354
```

<210> SEQ ID NO 14
<211> LENGTH: 294
<212> TYPE: DNA
<213> ORGANISM: artificial sequence
<220> FEATURE:
<223> OTHER INFORMATION: synthetic gene

<400> SEQUENCE: 14

```
atgtcgtact accatcacca tcaccatcac ctcgaatcaa caagtttgta caaaaaagca    60
```

| | |
|---|---:|
| ggctccgcgg ccgccccctt caccggatcc atcgaaggtc gtttccacga aaactggccg | 120 |
| tctgccggcg gtacctctac ttccaaagct tccaccacta cgacttctag caaaaccacc | 180 |
| actacatcct ctaagactac cacgactacc tccaaaacct ctactacctc tagctcctct | 240 |
| acgggcggcg ccactcacaa gacctctact cagcgtctgc tggctgcata atga | 294 |

<210> SEQ ID NO 15
<211> LENGTH: 96
<212> TYPE: PRT
<213> ORGANISM: artificial sequence
<220> FEATURE:
<223> OTHER INFORMATION: synthetic peptide

<400> SEQUENCE: 15

Met Ser Tyr Tyr His His His His His His Leu Glu Ser Thr Ser Leu
1               5                   10                  15

Tyr Lys Lys Ala Gly Ser Ala Ala Ala Pro Phe Thr Gly Ser Ile Glu
            20                  25                  30

Gly Arg Phe His Glu Asn Trp Pro Ser Ala Gly Gly Thr Ser Thr Ser
        35                  40                  45

Lys Ala Ser Thr Thr Thr Thr Ser Ser Lys Thr Thr Thr Thr Ser Ser
    50                  55                  60

Lys Thr Thr Thr Thr Thr Ser Lys Thr Ser Thr Ser Ser Ser Ser
65                  70                  75                  80

Thr Gly Gly Ala Thr His Lys Thr Ser Thr Gln Arg Leu Leu Ala Ala
                85                  90                  95

<210> SEQ ID NO 16
<211> LENGTH: 4945
<212> TYPE: DNA
<213> ORGANISM: artificial sequence
<220> FEATURE:
<223> OTHER INFORMATION: Plasmid

<400> SEQUENCE: 16

| | |
|---|---:|
| agatctcgat cccgcgaaat taatacgact cactataggg agaccacaac ggtttccctc | 60 |
| tagaaataat tttgtttaac tttaagaagg agatatacat atgtcgtact accatcacca | 120 |
| tcaccatcac ctcgaatcaa caagtttgta caaaaaagca ggctccgcgg ccgccccctt | 180 |
| caccggatcc atcgatccac gtttccacga aaactggccg tctgccggcg gtacctctac | 240 |
| ttccaaagct tccaccacta cgacttctag caaaaccacc actacatcct ctaagactac | 300 |
| cacgactacc tccaaaacct ctactacctc tagctcctct acgggcggcg ccactcacaa | 360 |
| gacctctact cagcgtctgc tggctgcata atgaaagggt gggcgcgccg acccagcttt | 420 |
| cttgtacaaa gtggttgatt cgaggctgct aacaaagccc gaaaggaagc tgagttggct | 480 |
| gctgccaccg ctgagcaata actagcataa ccccttgggg cctctaaacg ggtcttgagg | 540 |
| ggttttttgc tgaaaggagg aactatatcc ggatatccac aggacgggtg tggtcgccat | 600 |
| gatcgcgtag tcgatagtgg ctccaagtag cgaagcgagc aggactgggc ggcggccaaa | 660 |
| gcggtcggac agtgctccga gaacgggtgc gcatagaaat tgcatcaacg catatagcgc | 720 |
| tagcagcacg ccatagtgac tggcgatgct gtcggaatgg acgatatccc gcaagaggcc | 780 |
| cggcagtacc ggcataacca agcctatgcc tacagcatcc agggtgacgg tgccgaggat | 840 |
| gacgatgagc gcattgttag atttcataca cggtgcctga ctgcgttagc aatttaactg | 900 |
| tgataaacta ccgcattaaa gcttatcgat gataagctgt caaacatgag aattcttgaa | 960 |
| gacgaaaggg cctcgtgata cgcctatttt tataggttaa tgtcatgata taatggtttt | 1020 |

```
cttagacgtc aggtggcact tttcggggaa atgtgcgcgg aaccccctatt tgtttatttt    1080 tctaaataca ttcaaatatg tatccgctca tgagacaata accctgataa atgcttcaat    1140
aatattgaaa aaggaagagt atgagtattc aacatttccg tgtcgccctt attccctttt    1200
ttgcggcatt ttgccttcct gttttttgctc acccagaaac gctggtgaaa gtaaaagatg    1260
ctgaagatca gttgggtgca cgagtgggtt acatcgaact ggatctcaac agcggtaaga    1320
tccttgagag ttttcgcccc gaagaacgtt ttccaatgat gagcactttt aaagttctgc    1380
tatgtggcgc ggtattatcc cgtgttgacg ccgggcaaga gcaactcggt cgccgcatac    1440
actattctca gaatgacttg gttgagtact caccagtcac agaaaagcat cttacggatg    1500
gcatgacagt aagagaatta tgcagtgctg ccataaccat gagtgataac actgcggcca    1560
acttacttct gacaacgatc ggaggaccga aggagctaac cgcttttttg cacaacatgg    1620
gggatcatgt aactcgcctt gatcgttggg aaccggagct gaatgaagcc ataccaaacg    1680
acgagcgtga caccacgatg cctgcagcaa tggcaacaac gttgcgcaaa ctattaactg    1740
gcgaactact tactctagct tcccggcaac aattaataga ctggatggag gcggataaag    1800
ttgcaggacc acttctgcgc tcggcccttc cggctggctg gtttattgct gataaatctg    1860
gagccggtga gcgtgggtct cgcggtatca ttgcagcact ggggccagat ggtaagccct    1920
cccgtatcgt agttatctac acgacgggga gtcaggcaac tatggatgaa cgaaatagac    1980
agatcgctga gataggtgcc tcactgatta agcattggta actgtcagac caagtttact    2040
catatatact ttagattgat ttaaaacttc attttttaatt taaaaggatc taggtgaaga    2100
tcctttttga taatctcatg accaaaatcc cttaacgtga gttttcgttc cactgagcgt    2160
cagaccccgt agaaaagatc aaaggatctt cttgagatcc ttttttttctg cgcgtaatct    2220 gctgcttgca acaaaaaaa ccaccgctac cagcggtggt ttgtttgccg atcaagagc    2280 taccaactct ttttccgaag gtaactggct tcagcagagc gcagatacca atactgtcc    2340 ttctagtgta gccgtagtta ggccaccact tcaagaactc tgtagcaccg cctacatacc    2400
tcgctctgct aatcctgtta ccagtggctg ctgccagtgg cgataagtcg tgtcttaccg    2460
ggttggactc aagacgatag ttaccggata aggcgcagcg gtcgggctga acggggggtt    2520
cgtgcacaca gcccagcttg gagcgaacga cctacaccga actgagatac ctacagcgtg    2580
agctatgaga aagcgccacg cttcccgaag ggagaaaggc ggacaggtat ccggtaagcg    2640
gcagggtcgg aacaggagag cgcacgaggg agcttccagg gggaaacgcc tggtatcttt    2700
atagtcctgt cgggtttcgc cacctctgac ttgagcgtcg atttttgtga tgctcgtcag    2760
gggggcggag cctatggaaa aacgccagca acgcggcctt tttacggttc ctggccttt    2820 gctggccttt tgctcacatg ttctttcctg cgttatcccc tgattctgtg ataaccgta    2880 ttaccgcctt tgagtgagct gataccgctc gccgcagccg aacgaccgag cgcagcgagt    2940
cagtgagcga ggaagcggaa gagcgcctga tgcggtattt tctccttacg catctgtgcg    3000
gtatttcaca ccgcatatat ggtgcactct cagtacaatc tgctctgatg ccgcatagtt    3060
aagccagtat acactccgct atcgctacgt gactgggtca tggctgcgcc ccgacacccg    3120
ccaacacccg ctgacgcgcc ctgacgggct tgtctgctcc cggcatccgc ttacagacaa    3180
gctgtgaccg tctccgggag ctgcatgtgt cagaggtttt caccgtcatc accgaaacgc    3240
gcgaggcagc tgcggtaaag ctcatcagcg tggtcgtgaa gcgattcaca gatgtctgcc    3300
tgttcatccg cgtccagctc gttgagtttc tccagaagcg ttaatgtctg gcttctgata    3360
```

-continued

```
aagcgggcca tgttaagggc ggttttttcc tgtttggtca ctgatgcctc cgtgtaaggg    3420
ggatttctgt tcatgggggt aatgataccg atgaaacgag agaggatgct cacgatacgg    3480
gttactgatg atgaacatgc ccggttactg aacgttgtg agggtaaaca actggcggta     3540
tggatgcggc gggaccagag aaaaatcact cagggtcaat gccagcgctt cgttaataca    3600
gatgtaggtg ttccacaggg tagccagcag catcctgcga tgcagatccg aacataatg     3660 gtgcagggcg ctgacttccg cgtttccaga ctttacgaaa cacggaaacc gaagaccatt    3720
catgttgttg ctcaggtcgc agacgttttg cagcagcagt cgcttcacgt tcgctcgcgt    3780
atcggtgatt cattctgcta accagtaagg caaccccgcc agcctagccg ggtcctcaac    3840
gacaggagca cgatcatgcg cacccgtggc caggacccaa cgctgcccga tgcgccgc     3900 gtgcggctgc tggagatggc ggacgcgatg gatatgttct gccaagggtt ggtttgcgca    3960
ttcacagttc tccgcaagaa ttgattggct ccaattcttg gagtggtgaa tccgttagcg    4020
aggtgccgcc ggcttccatt caggtcgagg tggcccggct ccatgcaccg cgacgcaacg    4080
cggggaggca gacaaggtat agggcggcgc ctacaatcca tgccaacccg ttccatgtgc    4140
tcgccgaggc ggcataaatc gccgtgacga tcagcggtcc agtgatcgaa gttaggctgg    4200
taagagccgc gagcgatcct tgaagctgtc cctgatggtc gtcatctacc tgcctggaca    4260
gcatggcctg caacgcgggc atcccgatgc cgccggaagc gagaagaatc ataatgggga    4320
aggccatcca gcctcgcgtc gcgaacgcca gcaagacgta gcccagcgcg tcggccgcca    4380
tgccggcgat aatggcctgc ttctcgccga aacgtttggt ggcgggacca gtgacgaagg    4440
cttgagcgag ggcgtgcaag attccgaata ccgcaagcga caggccgatc atcgtcgcgc    4500
tccagcgaaa gcggtcctcg ccgaaaatga cccagagcgc tgccggcacc tgtcctacga    4560
gttgcatgat aaagaagaca gtcataagtg cggcgacgat agtcatgccc gcgcccacc    4620 ggaaggagct gactgggttg aaggctctca agggcatcgg tcgatcgacg ctctccctta    4680
tgcgactcct gcattaggaa gcagcccagt agtaggttga ggccgttgag caccgccgcc    4740
gcaaggaatg gtgcatgcaa ggagatggcg cccaacagtc cccggccac ggggcctgcc     4800 accataccca cgccgaaaca agcgctcatg agcccgaagt ggcgagcccg atcttcccca    4860
tcggtgatgt cggcgatata ggcgccagca accgcacctg tggcgccggt gatgccggcc    4920
acgatgcgtc cggcgtagag gatcg                                         4945
```

<210> SEQ ID NO 17
<211> LENGTH: 45
<212> TYPE: DNA
<213> ORGANISM: artificial sequence
<220> FEATURE:
<223> OTHER INFORMATION: synthetic oligonucleotide

<400> SEQUENCE: 17
ccccttcacc ggatccatcg atccacgttt ccacgaaaac tggcc             45

<210> SEQ ID NO 18
<211> LENGTH: 45
<212> TYPE: DNA
<213> ORGANISM: artificial sequence
<220> FEATURE:
<223> OTHER INFORMATION: synthetic oligonucleotide

<400> SEQUENCE: 18
ggccagtttt cgtggaaacg tggatcgatg gatccggtga agggg             45

<210> SEQ ID NO 19
<211> LENGTH: 294
<212> TYPE: DNA
<213> ORGANISM: artificial sequence
<220> FEATURE:
<223> OTHER INFORMATION: synthetic gene

<400> SEQUENCE: 19

```
atgtcgtact accatcacca tcaccatcac ctcgaatcaa caagtttgta caaaaaagca    60
ggctccgcgg ccgccccctt caccggatcc atcgatccac gtttccacga aaactggccg   120
tctgccggcg gtacctctac ttccaaagct tccaccacta cgacttctag caaaaccacc   180
actacatcct ctaagactac cacgactacc tccaaaacct ctactacctc tagctcctct   240
acgggcggcg ccactcacaa gacctctact cagcgtctgc tggctgcata atga         294
```

<210> SEQ ID NO 20
<211> LENGTH: 96
<212> TYPE: PRT
<213> ORGANISM: artificial sequence
<220> FEATURE:
<223> OTHER INFORMATION: synthetic peptide

<400> SEQUENCE: 20

```
Met Ser Tyr Tyr His His His His His His Leu Glu Ser Thr Ser Leu
1               5                   10                  15

Tyr Lys Lys Ala Gly Ser Ala Ala Ala Pro Phe Thr Gly Ser Ile Asp
            20                  25                  30

Pro Arg Phe His Glu Asn Trp Pro Ser Ala Gly Gly Thr Ser Thr Ser
        35                  40                  45

Lys Ala Ser Thr Thr Thr Thr Ser Ser Lys Thr Thr Thr Thr Ser Ser
    50                  55                  60

Lys Thr Thr Thr Thr Thr Ser Lys Thr Ser Thr Thr Ser Ser Ser Ser
65                  70                  75                  80

Thr Gly Gly Ala Thr His Lys Thr Ser Thr Gln Arg Leu Leu Ala Ala
            85                  90                  95
```

<210> SEQ ID NO 21
<211> LENGTH: 47
<212> TYPE: DNA
<213> ORGANISM: artificial sequence
<220> FEATURE:
<223> OTHER INFORMATION: synthetic oligonucleotide

<400> SEQUENCE: 21

```
tatgcgtgtg ctgctggtgg cgctggcgct gctggcgctg gcggcgg              47
```

<210> SEQ ID NO 22
<211> LENGTH: 49
<212> TYPE: DNA
<213> ORGANISM: artificial sequence
<220> FEATURE:
<223> OTHER INFORMATION: synthetic oligonucleotide

<400> SEQUENCE: 22

```
gatcccgccg ccagcgccag cagcgccagc gccaccagca gcacacgca             49
```

<210> SEQ ID NO 23
<211> LENGTH: 50
<212> TYPE: DNA
<213> ORGANISM: artificial sequence
<220> FEATURE:
<223> OTHER INFORMATION: synthetic oligonucleotide

```
<400> SEQUENCE: 23
tatgagcgcg accagcaccc acaccagcgg tggttgcggt tgccagccgg         50

<210> SEQ ID NO 24
<211> LENGTH: 52
<212> TYPE: DNA
<213> ORGANISM: artificial sequence
<220> FEATURE:
<223> OTHER INFORMATION: synthetic oligonucleotide

<400> SEQUENCE: 24
gatcccggct ggcaaccgca accaccgctg gtgtgggtgc tggtcgcgct ca      52

<210> SEQ ID NO 25
<211> LENGTH: 50
<212> TYPE: DNA
<213> ORGANISM: artificial sequence
<220> FEATURE:
<223> OTHER INFORMATION: synthetic oligonucleotide

<400> SEQUENCE: 25
tatgccgccg ccggtgcacc tgccgccgcc ggtgcacctg ccgccgccgg         50

<210> SEQ ID NO 26
<211> LENGTH: 52
<212> TYPE: DNA
<213> ORGANISM: artificial sequence
<220> FEATURE:
<223> OTHER INFORMATION: synthetic oligonucleotide

<400> SEQUENCE: 26
gatcccggcg gcggcaggtg caccggcggc ggcaggtgca ccggcggcgg ca      52

<210> SEQ ID NO 27
<211> LENGTH: 50
<212> TYPE: DNA
<213> ORGANISM: artificial sequence
<220> FEATURE:
<223> OTHER INFORMATION: synthetic oligonucleotide

<400> SEQUENCE: 27
tatggtgcac ctgccgccgc cggtgcacct gccgccgccg gtgcacctgg         50

<210> SEQ ID NO 28
<211> LENGTH: 52
<212> TYPE: DNA
<213> ORGANISM: artificial sequence
<220> FEATURE:
<223> OTHER INFORMATION: synthetic oligonucleotide

<400> SEQUENCE: 28
gatcccaggt gcaccggcgg cggcaggtgc accggcggcg gcaggtgcac ca      52

<210> SEQ ID NO 29
<211> LENGTH: 50
<212> TYPE: DNA
<213> ORGANISM: artificial sequence
<220> FEATURE:
<223> OTHER INFORMATION: synthetic oligonucleotide

<400> SEQUENCE: 29
tatgccgccg ccggtgcacc tgccgccgcc ggtgcacgtg ccgccgccgg         50

<210> SEQ ID NO 30
<211> LENGTH: 52
```

<210> SEQ ID NO 30
<211> LENGTH: 52
<212> TYPE: DNA
<213> ORGANISM: artificial sequence
<220> FEATURE:
<223> OTHER INFORMATION: synthetic oligonucleotide

<400> SEQUENCE: 30
gatcccggcg gcggcacgtg caccggcggc ggcaggtgca ccggcggcgg ca        52

<210> SEQ ID NO 31
<211> LENGTH: 50
<212> TYPE: DNA
<213> ORGANISM: artificial sequence
<220> FEATURE:
<223> OTHER INFORMATION: synthetic oligonucleotide

<400> SEQUENCE: 31
tatggtgcac ctgccgccgc cgccgtgcca ctacccgacc cagccgccgg           50

<210> SEQ ID NO 32
<211> LENGTH: 52
<212> TYPE: DNA
<213> ORGANISM: artificial sequence
<220> FEATURE:
<223> OTHER INFORMATION: synthetic oligonucleotide

<400> SEQUENCE: 32
gatcccggcg gctgggtcgg gtagtggcac ggcggcggcg gcaggtgcac ca        52

<210> SEQ ID NO 33
<211> LENGTH: 50
<212> TYPE: DNA
<213> ORGANISM: artificial sequence
<220> FEATURE:
<223> OTHER INFORMATION: synthetic oligonucleotide

<400> SEQUENCE: 33
tatgcgtccg cagccgcacc cgcagccgca cccgtgcccg tgccagcagg           50

<210> SEQ ID NO 34
<211> LENGTH: 52
<212> TYPE: DNA
<213> ORGANISM: artificial sequence
<220> FEATURE:
<223> OTHER INFORMATION: synthetic oligonucleotide

<400> SEQUENCE: 34
gatccctgct ggcacgggca cgggtgcggc tgcgggtgcg gctgcggacg ca        52

<210> SEQ ID NO 35
<211> LENGTH: 50
<212> TYPE: DNA
<213> ORGANISM: artificial sequence
<220> FEATURE:
<223> OTHER INFORMATION: synthetic oligonucleotide

<400> SEQUENCE: 35
tatgccgcac ccgagcccgt gccagctgca ggggacctgc ggtgtgggtg           50

<210> SEQ ID NO 36
<211> LENGTH: 52
<212> TYPE: DNA
<213> ORGANISM: artificial sequence
<220> FEATURE:
<223> OTHER INFORMATION: synthetic oligonucleotide

<400> SEQUENCE: 36

-continued gatccaccca caccgcaggt ccctgcagc tggcacgggc tcgggtgcgg ca    52

<210> SEQ ID NO 37
<211> LENGTH: 50
<212> TYPE: DNA
<213> ORGANISM: artificial sequence
<220> FEATURE:
<223> OTHER INFORMATION: synthetic oligonucleotide

<400> SEQUENCE: 37
tatgagcacc ccgatcctgg gtcagtgcgt ggaattcctg cgtcaccagg    50

<210> SEQ ID NO 38
<211> LENGTH: 52
<212> TYPE: DNA
<213> ORGANISM: artificial sequence
<220> FEATURE:
<223> OTHER INFORMATION: synthetic oligonucleotide

<400> SEQUENCE: 38
gatccctggt gacgcaggaa ttccacgcac tgacccagga tcggggtgct ca    52

<210> SEQ ID NO 39
<211> LENGTH: 50
<212> TYPE: DNA
<213> ORGANISM: artificial sequence
<220> FEATURE:
<223> OTHER INFORMATION: synthetic oligonucleotide

<400> SEQUENCE: 39
tatgtgcagc ccgaccgcga ccccgtactg cagcccgcag tgccagagcg    50

<210> SEQ ID NO 40
<211> LENGTH: 52
<212> TYPE: DNA
<213> ORGANISM: artificial sequence
<220> FEATURE:
<223> OTHER INFORMATION: synthetic oligonucleotide

<400> SEQUENCE: 40
gatccgctct ggcactgcgg gctgcagtac ggggtcgcgg tcgggctgca ca    52

<210> SEQ ID NO 41
<211> LENGTH: 50
<212> TYPE: DNA
<213> ORGANISM: artificial sequence
<220> FEATURE:
<223> OTHER INFORMATION: synthetic oligonucleotide

<400> SEQUENCE: 41
tatgctgcgt cagcagtgct gccagcagct gcgtcaggtg gaaccgcagg    50

<210> SEQ ID NO 42
<211> LENGTH: 52
<212> TYPE: DNA
<213> ORGANISM: artificial sequence
<220> FEATURE:
<223> OTHER INFORMATION: synthetic oligonucleotide

<400> SEQUENCE: 42
gatccctgcg gttccacctg acgcagctgc tggcagcact gctgacgcag ca    52

<210> SEQ ID NO 43
<211> LENGTH: 50
<212> TYPE: DNA
<213> ORGANISM: artificial sequence
<220> FEATURE:
<223> OTHER INFORMATION: synthetic oligonucleotide

<400> SEQUENCE: 43
tatgcaccgt taccaggcga tcttcggtct ggtgctgcag agcatcctgg        50

<210> SEQ ID NO 44
<211> LENGTH: 52
<212> TYPE: DNA
<213> ORGANISM: artificial sequence
<220> FEATURE:
<223> OTHER INFORMATION: synthetic oligonucleotide

<400> SEQUENCE: 44
gatcccagga tgctctgcag caccagaccg aagatcgcct ggtaacggtg ca     52

<210> SEQ ID NO 45
<211> LENGTH: 50
<212> TYPE: DNA
<213> ORGANISM: artificial sequence
<220> FEATURE:
<223> OTHER INFORMATION: synthetic oligonucleotide

<400> SEQUENCE: 45
tatgcagcag cagccgcaga gcggtcaggt ggcgggtctg ctggcggcgg        50

<210> SEQ ID NO 46
<211> LENGTH: 52
<212> TYPE: DNA
<213> ORGANISM: artificial sequence
<220> FEATURE:
<223> OTHER INFORMATION: synthetic oligonucleotide

<400> SEQUENCE: 46
gatcccgccg ccagcagacc cgccacctga ccgctctgcg gctgctgctg ca     52

<210> SEQ ID NO 47
<211> LENGTH: 50
<212> TYPE: DNA
<213> ORGANISM: artificial sequence
<220> FEATURE:
<223> OTHER INFORMATION: synthetic oligonucleotide

<400> SEQUENCE: 47
tatgcagatc gcgcagcagc tgaccgcgat gtgcggtctg cagcagccgg        50

<210> SEQ ID NO 48
<211> LENGTH: 52
<212> TYPE: DNA
<213> ORGANISM: artificial sequence
<220> FEATURE:
<223> OTHER INFORMATION: synthetic oligonucleotide

<400> SEQUENCE: 48
gatcccggct gctgcagacc gcacatcgcg gtcagctgct gcgcgatctg ca     52

<210> SEQ ID NO 49
<211> LENGTH: 44
<212> TYPE: DNA
<213> ORGANISM: artificial sequence
<220> FEATURE:
<223> OTHER INFORMATION: synthetic oligonucleotide

<400> SEQUENCE: 49
tatgaccccg tgcccgtacg cggcggcggg tggtgtgccg cacg              44

<210> SEQ ID NO 50
<211> LENGTH: 46
<212> TYPE: DNA
<213> ORGANISM: artificial sequence
<220> FEATURE:
<223> OTHER INFORMATION: synthetic oligonucleotide

<400> SEQUENCE: 50
gatccgtgcg gcacaccacc cgccgccgcg tacgggcacg gggtca         46

<210> SEQ ID NO 51
<211> LENGTH: 50
<212> TYPE: DNA
<213> ORGANISM: artificial sequence
<220> FEATURE:
<223> OTHER INFORMATION: synthetic oligonucleotide

<400> SEQUENCE: 51
tatggtggcg ctggcgctgc tggcgctggc ggcgagcgcg accagcaccg         50

<210> SEQ ID NO 52
<211> LENGTH: 52
<212> TYPE: DNA
<213> ORGANISM: artificial sequence
<220> FEATURE:
<223> OTHER INFORMATION: synthetic oligonucleotide

<400> SEQUENCE: 52
gatccggtgc tggtcgcgct cgccgccagc gccagcagcg ccagcgccac ca         52

<210> SEQ ID NO 53
<211> LENGTH: 50
<212> TYPE: DNA
<213> ORGANISM: artificial sequence
<220> FEATURE:
<223> OTHER INFORMATION: synthetic oligonucleotide

<400> SEQUENCE: 53
tatgcacacc agcggtggtt gcggttgcca gccgccgccg ccggtgcacg         50

<210> SEQ ID NO 54
<211> LENGTH: 52
<212> TYPE: DNA
<213> ORGANISM: artificial sequence
<220> FEATURE:
<223> OTHER INFORMATION: synthetic oligonucleotide

<400> SEQUENCE: 54
gatccgtgca ccggcggcgg cggctggcaa ccgcaaccac cgctggtgtg ca         52

<210> SEQ ID NO 55
<211> LENGTH: 50
<212> TYPE: DNA
<213> ORGANISM: artificial sequence
<220> FEATURE:
<223> OTHER INFORMATION: synthetic oligonucleotide

<400> SEQUENCE: 55
tatgctgccg ccgccggtgc acctgccgcc gccggtgcac ctgccgccgg         50

<210> SEQ ID NO 56
<211> LENGTH: 52
<212> TYPE: DNA
<213> ORGANISM: artificial sequence
<220> FEATURE:
<223> OTHER INFORMATION: synthetic oligonucleotide

```
<400> SEQUENCE: 56
gatcccggcg gcaggtgcac cggcggcggc aggtgcaccg gcggcggcag ca         52

<210> SEQ ID NO 57
<211> LENGTH: 50
<212> TYPE: DNA
<213> ORGANISM: artificial sequence
<220> FEATURE:
<223> OTHER INFORMATION: synthetic oligonucleotide

<400> SEQUENCE: 57
tatgccggtg cacctgccgc cgccggtgca cctgccgccg ccggtgcacg            50

<210> SEQ ID NO 58
<211> LENGTH: 52
<212> TYPE: DNA
<213> ORGANISM: artificial sequence
<220> FEATURE:
<223> OTHER INFORMATION: synthetic oligonucleotide

<400> SEQUENCE: 58
gatccgtgca ccggcggcgg caggtgcacc ggcggcggca ggtgcaccgg ca         52

<210> SEQ ID NO 59
<211> LENGTH: 50
<212> TYPE: DNA
<213> ORGANISM: artificial sequence
<220> FEATURE:
<223> OTHER INFORMATION: synthetic oligonucleotide

<400> SEQUENCE: 59
tatgctgccg ccgccggtgc acgtgccgcc gccggtgcac ctgccgccgg            50

<210> SEQ ID NO 60
<211> LENGTH: 52
<212> TYPE: DNA
<213> ORGANISM: artificial sequence
<220> FEATURE:
<223> OTHER INFORMATION: synthetic oligonucleotide

<400> SEQUENCE: 60
gatcccggcg gcaggtgcac cggcggcggc acgtgcaccg gcggcggcag ca         52

<210> SEQ ID NO 61
<211> LENGTH: 50
<212> TYPE: DNA
<213> ORGANISM: artificial sequence
<220> FEATURE:
<223> OTHER INFORMATION: synthetic oligonucleotide

<400> SEQUENCE: 61
tatgccgccg tgccactacc cgacccagcc gccgcgtccg cagccgcacg            50

<210> SEQ ID NO 62
<211> LENGTH: 52
<212> TYPE: DNA
<213> ORGANISM: artificial sequence
<220> FEATURE:
<223> OTHER INFORMATION: synthetic oligonucleotide

<400> SEQUENCE: 62
gatccgtgcg gctgcggacg cggcggctgg gtcgggtagt ggcacggcgg ca         52

<210> SEQ ID NO 63
```

<210> SEQ ID NO 63
<211> LENGTH: 50
<212> TYPE: DNA
<213> ORGANISM: artificial sequence
<220> FEATURE:
<223> OTHER INFORMATION: synthetic oligonucleotide

<400> SEQUENCE: 63
tatgccgcag ccgcacccgt gcccgtgcca gcagccgcac ccgagccgg         50

<210> SEQ ID NO 64
<211> LENGTH: 52
<212> TYPE: DNA
<213> ORGANISM: artificial sequence
<220> FEATURE:
<223> OTHER INFORMATION: synthetic oligonucleotide

<400> SEQUENCE: 64
gatcccgggc tcgggtgcgg ctgctggcac gggcacgggt gcggctgcgg ca       52

<210> SEQ ID NO 65
<211> LENGTH: 50
<212> TYPE: DNA
<213> ORGANISM: artificial sequence
<220> FEATURE:
<223> OTHER INFORMATION: synthetic oligonucleotide

<400> SEQUENCE: 65
tatgtgccag ctgcagggga cctgcggtgt gggtagcacc ccgatcctgg         50

<210> SEQ ID NO 66
<211> LENGTH: 52
<212> TYPE: DNA
<213> ORGANISM: artificial sequence
<220> FEATURE:
<223> OTHER INFORMATION: synthetic oligonucleotide

<400> SEQUENCE: 66
gatcccagga tcggggtgct acccacaccg caggtccct gcagctggca ca       52

<210> SEQ ID NO 67
<211> LENGTH: 50
<212> TYPE: DNA
<213> ORGANISM: artificial sequence
<220> FEATURE:
<223> OTHER INFORMATION: synthetic oligonucleotide

<400> SEQUENCE: 67
tatgggtcag tgcgtggaat tcctgcgtca ccagtgcagc ccgaccgcgg         50

<210> SEQ ID NO 68
<211> LENGTH: 52
<212> TYPE: DNA
<213> ORGANISM: artificial sequence
<220> FEATURE:
<223> OTHER INFORMATION: synthetic oligonucleotide

<400> SEQUENCE: 68
gatcccgcgg tcgggctgca ctggtgacgc aggaattcca cgcactgacc ca       52

<210> SEQ ID NO 69
<211> LENGTH: 50
<212> TYPE: DNA
<213> ORGANISM: artificial sequence
<220> FEATURE:
<223> OTHER INFORMATION: synthetic oligonucleotide

<400> SEQUENCE: 69

-continued tatgaccccg tactgcagcc cgcagtgcca gagcctgcgt cagcagtgcg    50

<210> SEQ ID NO 70
<211> LENGTH: 52
<212> TYPE: DNA
<213> ORGANISM: artificial sequence
<220> FEATURE:
<223> OTHER INFORMATION: synthetic oligonucleotide

<400> SEQUENCE: 70
gatccgcact gctgacgcag gctctggcac tgcgggctgc agtacggggt ca    52

<210> SEQ ID NO 71
<211> LENGTH: 50
<212> TYPE: DNA
<213> ORGANISM: artificial sequence
<220> FEATURE:
<223> OTHER INFORMATION: synthetic oligonucleotide

<400> SEQUENCE: 71
tatgtgccag cagctgcgtc aggtggaacc gcagcaccgt taccaggcgg    50

<210> SEQ ID NO 72
<211> LENGTH: 52
<212> TYPE: DNA
<213> ORGANISM: artificial sequence
<220> FEATURE:
<223> OTHER INFORMATION: synthetic oligonucleotide

<400> SEQUENCE: 72
gatcccgcct ggtaacggtg ctgcggttcc acctgacgca gctgctggca ca    52

<210> SEQ ID NO 73
<211> LENGTH: 50
<212> TYPE: DNA
<213> ORGANISM: artificial sequence
<220> FEATURE:
<223> OTHER INFORMATION: synthetic oligonucleotide

<400> SEQUENCE: 73
tatgatcttc ggtctggtgc tgcagagcat cctgcagcag cagccgcagg    50

<210> SEQ ID NO 74
<211> LENGTH: 52
<212> TYPE: DNA
<213> ORGANISM: artificial sequence
<220> FEATURE:
<223> OTHER INFORMATION: synthetic oligonucleotide

<400> SEQUENCE: 74
gatccctgcg gctgctgctg caggatgctc tgcagcacca gaccgaagat ca    52

<210> SEQ ID NO 75
<211> LENGTH: 50
<212> TYPE: DNA
<213> ORGANISM: artificial sequence
<220> FEATURE:
<223> OTHER INFORMATION: synthetic oligonucleotide

<400> SEQUENCE: 75
tatgagcggt caggtggcgg gtctgctggc ggcgcagatc gcgcagcagg    50

<210> SEQ ID NO 76
<211> LENGTH: 52
<212> TYPE: DNA

```
<213> ORGANISM: artificial sequence
<220> FEATURE:
<223> OTHER INFORMATION: synthetic oligonucleotide

<400> SEQUENCE: 76
gatccctgct gcgcgatctg cgccgccagc agacccgcca cctgaccgct ca          52

<210> SEQ ID NO 77
<211> LENGTH: 50
<212> TYPE: DNA
<213> ORGANISM: artificial sequence
<220> FEATURE:
<223> OTHER INFORMATION: synthetic oligonucleotide

<400> SEQUENCE: 77
tatgctgacc gcgatgtgcg gtctgcagca gccgaccccg tgcccgtacg             50

<210> SEQ ID NO 78
<211> LENGTH: 52
<212> TYPE: DNA
<213> ORGANISM: artificial sequence
<220> FEATURE:
<223> OTHER INFORMATION: synthetic oligonucleotide

<400> SEQUENCE: 78
gatccgtacg ggcacggggt cggctgctgc agaccgcaca tcgcggtcag ca          52

<210> SEQ ID NO 79
<211> LENGTH: 50
<212> TYPE: DNA
<213> ORGANISM: artificial sequence
<220> FEATURE:
<223> OTHER INFORMATION: synthetic oligonucleotide

<400> SEQUENCE: 79
tatgctggcg ctggcggcga gcgcgaccag cacccacacc agcggtggtg             50

<210> SEQ ID NO 80
<211> LENGTH: 52
<212> TYPE: DNA
<213> ORGANISM: artificial sequence
<220> FEATURE:
<223> OTHER INFORMATION: synthetic oligonucleotide

<400> SEQUENCE: 80
gatccaccac cgctggtgtg ggtgctggtc gcgctcgccg ccagcgccag ca          52

<210> SEQ ID NO 81
<211> LENGTH: 50
<212> TYPE: DNA
<213> ORGANISM: artificial sequence
<220> FEATURE:
<223> OTHER INFORMATION: synthetic oligonucleotide

<400> SEQUENCE: 81
tatgtgcggt tgccagccgc cgccgccggt gcacctgccg ccgccggtgg             50

<210> SEQ ID NO 82
<211> LENGTH: 52
<212> TYPE: DNA
<213> ORGANISM: artificial sequence
<220> FEATURE:
<223> OTHER INFORMATION: synthetic oligonucleotide

<400> SEQUENCE: 82
gatcccaccg gcggcggcag gtgcaccggc ggcggcggct ggcaaccgca ca          52
```

```
<210> SEQ ID NO 83
<211> LENGTH: 50
<212> TYPE: DNA
<213> ORGANISM: artificial sequence
<220> FEATURE:
<223> OTHER INFORMATION: synthetic oligonucleotide

<400> SEQUENCE: 83
tatgcacctg ccgccgccgg tgcacctgcc gccgccggtg cacctgccgg              50

<210> SEQ ID NO 84
<211> LENGTH: 52
<212> TYPE: DNA
<213> ORGANISM: artificial sequence
<220> FEATURE:
<223> OTHER INFORMATION: synthetic oligonucleotide

<400> SEQUENCE: 84
gatcccggca ggtgcaccgg cggcggcagg tgcaccggcg gcggcaggtg ca           52

<210> SEQ ID NO 85
<211> LENGTH: 50
<212> TYPE: DNA
<213> ORGANISM: artificial sequence
<220> FEATURE:
<223> OTHER INFORMATION: synthetic oligonucleotide

<400> SEQUENCE: 85
tatgccgccg gtgcacctgc cgccgccggt gcacctgccg ccgccggtgg              50

<210> SEQ ID NO 86
<211> LENGTH: 52
<212> TYPE: DNA
<213> ORGANISM: artificial sequence
<220> FEATURE:
<223> OTHER INFORMATION: synthetic oligonucleotide

<400> SEQUENCE: 86
gatcccaccg gcggcggcag gtgcaccggc ggcggcaggt gcaccggcgg ca           52

<210> SEQ ID NO 87
<211> LENGTH: 50
<212> TYPE: DNA
<213> ORGANISM: artificial sequence
<220> FEATURE:
<223> OTHER INFORMATION: synthetic oligonucleotide

<400> SEQUENCE: 87
tatgcacgtg ccgccgccgg tgcacctgcc gccgccgccg tgccactacg              50

<210> SEQ ID NO 88
<211> LENGTH: 52
<212> TYPE: DNA
<213> ORGANISM: artificial sequence
<220> FEATURE:
<223> OTHER INFORMATION: synthetic oligonucleotide

<400> SEQUENCE: 88
gatccgtagt ggcacggcgg cggcggcagg tgcaccggcg gcggcacgtg ca           52

<210> SEQ ID NO 89
<211> LENGTH: 50
<212> TYPE: DNA
<213> ORGANISM: artificial sequence
<220> FEATURE:
```

```
<223> OTHER INFORMATION: synthetic oligonucleotide

<400> SEQUENCE: 89
tatgccgacc cagccgccgc gtccgcagcc gcacccgcag ccgcacccgg          50

<210> SEQ ID NO 90
<211> LENGTH: 52
<212> TYPE: DNA
<213> ORGANISM: artificial sequence
<220> FEATURE:
<223> OTHER INFORMATION: synthetic oligonucleotide

<400> SEQUENCE: 90
gatcccgggt gcggctgcgg gtgcggctgc ggacgcggcg gctgggtcgg ca       52

<210> SEQ ID NO 91
<211> LENGTH: 50
<212> TYPE: DNA
<213> ORGANISM: artificial sequence
<220> FEATURE:
<223> OTHER INFORMATION: synthetic oligonucleotide

<400> SEQUENCE: 91
tatgtgcccg tgccagcagc cgcacccgag cccgtgccag ctgcaggggg          50

<210> SEQ ID NO 92
<211> LENGTH: 52
<212> TYPE: DNA
<213> ORGANISM: artificial sequence
<220> FEATURE:
<223> OTHER INFORMATION: synthetic oligonucleotide

<400> SEQUENCE: 92
gatcccccct gcagctggca cgggctcggg tgcggctgct ggcacgggca ca       52

<210> SEQ ID NO 93
<211> LENGTH: 50
<212> TYPE: DNA
<213> ORGANISM: artificial sequence
<220> FEATURE:
<223> OTHER INFORMATION: synthetic oligonucleotide

<400> SEQUENCE: 93
tatgacctgc ggtgtgggta gcaccccgat cctgggtcag tgcgtggaag          50

<210> SEQ ID NO 94
<211> LENGTH: 52
<212> TYPE: DNA
<213> ORGANISM: artificial sequence
<220> FEATURE:
<223> OTHER INFORMATION: synthetic oligonucleotide

<400> SEQUENCE: 94
gatccttcca cgcactgacc caggatcggg gtgctaccca caccgcaggt ca       52

<210> SEQ ID NO 95
<211> LENGTH: 50
<212> TYPE: DNA
<213> ORGANISM: artificial sequence
<220> FEATURE:
<223> OTHER INFORMATION: synthetic oligonucleotide

<400> SEQUENCE: 95
tatgttcctg cgtcaccagt gcagcccgac cgcgaccccg tactgcagcg          50
```

<210> SEQ ID NO 96
<211> LENGTH: 52
<212> TYPE: DNA
<213> ORGANISM: artificial sequence
<220> FEATURE:
<223> OTHER INFORMATION: synthetic oligonucleotide

<400> SEQUENCE: 96
gatccgctgc agtacggggt cgcggtcggg ctgcactggt gacgcaggaa ca    52

<210> SEQ ID NO 97
<211> LENGTH: 50
<212> TYPE: DNA
<213> ORGANISM: artificial sequence
<220> FEATURE:
<223> OTHER INFORMATION: synthetic oligonucleotide

<400> SEQUENCE: 97
tatgccgcag tgccagagcc tgcgtcagca gtgctgccag cagctgcgtg    50

<210> SEQ ID NO 98
<211> LENGTH: 52
<212> TYPE: DNA
<213> ORGANISM: artificial sequence
<220> FEATURE:
<223> OTHER INFORMATION: synthetic oligonucleotide

<400> SEQUENCE: 98
gatccacgca gctgctggca gcactgctga cgcaggctct ggcactgcgg ca    52

<210> SEQ ID NO 99
<211> LENGTH: 50
<212> TYPE: DNA
<213> ORGANISM: artificial sequence
<220> FEATURE:
<223> OTHER INFORMATION: synthetic oligonucleotide

<400> SEQUENCE: 99
tatgcaggtg gaaccgcagc accgttacca ggcgatcttc ggtctggtgg    50

<210> SEQ ID NO 100
<211> LENGTH: 52
<212> TYPE: DNA
<213> ORGANISM: artificial sequence
<220> FEATURE:
<223> OTHER INFORMATION: synthetic oligonucleotide

<400> SEQUENCE: 100
gatcccacca gaccgaagat cgcctggtaa cggtgctgcg gttccacctg ca    52

<210> SEQ ID NO 101
<211> LENGTH: 50
<212> TYPE: DNA
<213> ORGANISM: artificial sequence
<220> FEATURE:
<223> OTHER INFORMATION: synthetic oligonucleotide

<400> SEQUENCE: 101
tatgctgcag agcatcctgc agcagcagcc gcagagcggt caggtggcgg    50

<210> SEQ ID NO 102
<211> LENGTH: 52
<212> TYPE: DNA
<213> ORGANISM: artificial sequence
<220> FEATURE:
<223> OTHER INFORMATION: synthetic oligonucleotide

<400> SEQUENCE: 102
gatcccgcca cctgaccgct ctgcggctgc tgctgcagga tgctctgcag ca    52

<210> SEQ ID NO 103
<211> LENGTH: 50
<212> TYPE: DNA
<213> ORGANISM: artificial sequence
<220> FEATURE:
<223> OTHER INFORMATION: synthetic oligonucleotide

<400> SEQUENCE: 103
tatgggtctg ctggcggcgc agatcgcgca gcagctgacc gcgatgtgcg    50

<210> SEQ ID NO 104
<211> LENGTH: 52
<212> TYPE: DNA
<213> ORGANISM: artificial sequence
<220> FEATURE:
<223> OTHER INFORMATION: synthetic oligonucleotide

<400> SEQUENCE: 104
gatccgcaca tcgcggtcag ctgctgcgcg atctgcgccg ccagcagacc ca    52

<210> SEQ ID NO 105
<211> LENGTH: 50
<212> TYPE: DNA
<213> ORGANISM: artificial sequence
<220> FEATURE:
<223> OTHER INFORMATION: synthetic oligonucleotide

<400> SEQUENCE: 105
tatgggtctg cagcagccga ccccgtgccc gtacgcggcg gcgggtggtg    50

<210> SEQ ID NO 106
<211> LENGTH: 52
<212> TYPE: DNA
<213> ORGANISM: artificial sequence
<220> FEATURE:
<223> OTHER INFORMATION: synthetic oligonucleotide

<400> SEQUENCE: 106
gatccaccac ccgccgccgc gtacgggcac ggggtcggct gctgcagacc ca    52

<210> SEQ ID NO 107
<211> LENGTH: 80
<212> TYPE: DNA
<213> ORGANISM: artificial sequence
<220> FEATURE:
<223> OTHER INFORMATION: synthetic oligonucleotide

<400> SEQUENCE: 107
tatgccgacc cagccgccgc gtccgcagcc gcacccgcag ccgcacccgt gcccgtgcca    60
gcagccgcac ccgagcccgg    80

<210> SEQ ID NO 108
<211> LENGTH: 82
<212> TYPE: DNA
<213> ORGANISM: artificial sequence
<220> FEATURE:
<223> OTHER INFORMATION: synthetic oligonucleotide

<400> SEQUENCE: 108
gatcccgggc tcgggtgcgg ctgctggcac gggcacgggt gcggctgcgg gtgcggctgc    60
ggacgcggcg gctgggtcgg ca    82

<210> SEQ ID NO 109
<211> LENGTH: 65
<212> TYPE: DNA
<213> ORGANISM: artificial sequence
<220> FEATURE:
<223> OTHER INFORMATION: synthetic oligonucleotide

<400> SEQUENCE: 109
tatgcgtccg cagccgcacc cgcagccgca cccgtgcccg tgccagcagc cgcacccgag    60
cccgg    65

<210> SEQ ID NO 110
<211> LENGTH: 67
<212> TYPE: DNA
<213> ORGANISM: artificial sequence
<220> FEATURE:
<223> OTHER INFORMATION: synthetic oligonucleotide

<400> SEQUENCE: 110
gatcccgggc tcgggtgcgg ctgctggcac gggcacgggt gcggctgcgg gtgcggctgc    60
ggacgca    67

<210> SEQ ID NO 111
<211> LENGTH: 15
<212> TYPE: PRT
<213> ORGANISM: Zea mays

<400> SEQUENCE: 111

Met Arg Val Leu Leu Val Ala Leu Ala Leu Leu Ala Leu Ala Ala
1               5                   10                  15

<210> SEQ ID NO 112
<211> LENGTH: 15
<212> TYPE: PRT
<213> ORGANISM: Zea mays

<400> SEQUENCE: 112

Ser Ala Thr Ser Thr His Thr Ser Gly Gly Cys Gly Cys Gln Pro
1               5                   10                  15

<210> SEQ ID NO 113
<211> LENGTH: 15
<212> TYPE: PRT
<213> ORGANISM: Zea mays

<400> SEQUENCE: 113

Pro Pro Pro Val His Leu Pro Pro Val His Leu Pro Pro
1               5                   10                  15

<210> SEQ ID NO 114
<211> LENGTH: 15
<212> TYPE: PRT
<213> ORGANISM: Zea mays

<400> SEQUENCE: 114

Val His Leu Pro Pro Pro Val His Leu Pro Pro Pro Val His Leu
1               5                   10                  15

<210> SEQ ID NO 115
<211> LENGTH: 15
<212> TYPE: PRT
<213> ORGANISM: Zea mays

-continued

<400> SEQUENCE: 115

Pro Pro Pro Val His Leu Pro Pro Val His Val Pro Pro Pro
1               5                   10                  15

<210> SEQ ID NO 116
<211> LENGTH: 15
<212> TYPE: PRT
<213> ORGANISM: Zea mays

<400> SEQUENCE: 116

Val His Leu Pro Pro Pro Pro Cys His Tyr Pro Thr Gln Pro Pro
1               5                   10                  15

<210> SEQ ID NO 117
<211> LENGTH: 15
<212> TYPE: PRT
<213> ORGANISM: Zea mays

<400> SEQUENCE: 117

Arg Pro Gln Pro His Pro Gln Pro His Pro Cys Pro Cys Gln Gln
1               5                   10                  15

<210> SEQ ID NO 118
<211> LENGTH: 15
<212> TYPE: PRT
<213> ORGANISM: Zea mays

<400> SEQUENCE: 118

Pro His Pro Ser Pro Cys Gln Leu Gln Gly Thr Cys Gly Val Gly
1               5                   10                  15

<210> SEQ ID NO 119
<211> LENGTH: 15
<212> TYPE: PRT
<213> ORGANISM: Zea mays

<400> SEQUENCE: 119

Ser Thr Pro Ile Leu Gly Gln Cys Val Glu Phe Leu Arg His Gln
1               5                   10                  15

<210> SEQ ID NO 120
<211> LENGTH: 15
<212> TYPE: PRT
<213> ORGANISM: Zea mays

<400> SEQUENCE: 120

Cys Ser Pro Thr Ala Thr Pro Tyr Cys Ser Pro Gln Cys Gln Ser
1               5                   10                  15

<210> SEQ ID NO 121
<211> LENGTH: 15
<212> TYPE: PRT
<213> ORGANISM: Zea mays

<400> SEQUENCE: 121

Leu Arg Gln Gln Cys Cys Gln Gln Leu Arg Gln Val Glu Pro Gln
1               5                   10                  15

<210> SEQ ID NO 122
<211> LENGTH: 15
<212> TYPE: PRT
<213> ORGANISM: Zea mays

<400> SEQUENCE: 122

```
His Arg Tyr Gln Ala Ile Phe Gly Leu Val Leu Gln Ser Ile Leu
1               5                   10                  15
```

<210> SEQ ID NO 123
<211> LENGTH: 15
<212> TYPE: PRT
<213> ORGANISM: Zea mays

<400> SEQUENCE: 123

```
Gln Gln Gln Pro Gln Ser Gly Gln Val Ala Gly Leu Leu Ala Ala
1               5                   10                  15
```

<210> SEQ ID NO 124
<211> LENGTH: 15
<212> TYPE: PRT
<213> ORGANISM: Zea mays

<400> SEQUENCE: 124

```
Gln Ile Ala Gln Gln Leu Thr Ala Met Cys Gly Leu Gln Gln Pro
1               5                   10                  15
```

<210> SEQ ID NO 125
<211> LENGTH: 13
<212> TYPE: PRT
<213> ORGANISM: Zea mays

<400> SEQUENCE: 125

```
Thr Pro Cys Pro Tyr Ala Ala Ala Gly Gly Val Pro His
1               5                   10
```

<210> SEQ ID NO 126
<211> LENGTH: 15
<212> TYPE: PRT
<213> ORGANISM: Zea mays

<400> SEQUENCE: 126

```
Val Ala Leu Ala Leu Leu Ala Leu Ala Ala Ser Ala Thr Ser Thr
1               5                   10                  15
```

<210> SEQ ID NO 127
<211> LENGTH: 15
<212> TYPE: PRT
<213> ORGANISM: Zea mays

<400> SEQUENCE: 127

```
His Thr Ser Gly Gly Cys Gly Cys Gln Pro Pro Pro Pro Val His
1               5                   10                  15
```

<210> SEQ ID NO 128
<211> LENGTH: 15
<212> TYPE: PRT
<213> ORGANISM: Zea mays

<400> SEQUENCE: 128

```
Leu Pro Pro Pro Val His Leu Pro Pro Val His Leu Pro Pro
1               5                   10                  15
```

<210> SEQ ID NO 129
<211> LENGTH: 15
<212> TYPE: PRT
<213> ORGANISM: Zea mays

<400> SEQUENCE: 129

```
Pro Val His Leu Pro Pro Val His Leu Pro Pro Val His
1               5                   10                  15
```

```
<210> SEQ ID NO 130
<211> LENGTH: 15
<212> TYPE: PRT
<213> ORGANISM: Zea mays

<400> SEQUENCE: 130

Leu Pro Pro Pro Val His Val Pro Pro Val His Leu Pro Pro
1               5                   10                  15

<210> SEQ ID NO 131
<211> LENGTH: 15
<212> TYPE: PRT
<213> ORGANISM: Zea mays

<400> SEQUENCE: 131

Pro Pro Cys His Tyr Pro Thr Gln Pro Pro Arg Pro Gln Pro His
1               5                   10                  15

<210> SEQ ID NO 132
<211> LENGTH: 15
<212> TYPE: PRT
<213> ORGANISM: Zea mays

<400> SEQUENCE: 132

Pro Gln Pro His Pro Cys Pro Cys Gln Gln Pro His Pro Ser Pro
1               5                   10                  15

<210> SEQ ID NO 133
<211> LENGTH: 15
<212> TYPE: PRT
<213> ORGANISM: Zea mays

<400> SEQUENCE: 133

Cys Gln Leu Gln Gly Thr Cys Gly Val Gly Ser Thr Pro Ile Leu
1               5                   10                  15

<210> SEQ ID NO 134
<211> LENGTH: 15
<212> TYPE: PRT
<213> ORGANISM: Zea mays

<400> SEQUENCE: 134

Gly Gln Cys Val Glu Phe Leu Arg His Gln Cys Ser Pro Thr Ala
1               5                   10                  15

<210> SEQ ID NO 135
<211> LENGTH: 15
<212> TYPE: PRT
<213> ORGANISM: Zea mays

<400> SEQUENCE: 135

Thr Pro Tyr Cys Ser Pro Gln Cys Gln Ser Leu Arg Gln Gln Cys
1               5                   10                  15

<210> SEQ ID NO 136
<211> LENGTH: 15
<212> TYPE: PRT
<213> ORGANISM: Zea mays

<400> SEQUENCE: 136

Cys Gln Gln Leu Arg Gln Val Glu Pro Gln His Arg Tyr Gln Ala
1               5                   10                  15
```

```
<210> SEQ ID NO 137
<211> LENGTH: 15
<212> TYPE: PRT
<213> ORGANISM: Zea mays

<400> SEQUENCE: 137

Ile Phe Gly Leu Val Leu Gln Ser Ile Leu Gln Gln Gln Pro Gln
1               5                   10                  15

<210> SEQ ID NO 138
<211> LENGTH: 15
<212> TYPE: PRT
<213> ORGANISM: Zea mays

<400> SEQUENCE: 138

Ser Gly Gln Val Ala Gly Leu Leu Ala Ala Gln Ile Ala Gln Gln
1               5                   10                  15

<210> SEQ ID NO 139
<211> LENGTH: 15
<212> TYPE: PRT
<213> ORGANISM: Zea mays

<400> SEQUENCE: 139

Leu Thr Ala Met Cys Gly Leu Gln Gln Pro Thr Pro Cys Pro Tyr
1               5                   10                  15

<210> SEQ ID NO 140
<211> LENGTH: 15
<212> TYPE: PRT
<213> ORGANISM: Zea mays

<400> SEQUENCE: 140

Leu Ala Leu Ala Ala Ser Ala Thr Ser Thr His Thr Ser Gly Gly
1               5                   10                  15

<210> SEQ ID NO 141
<211> LENGTH: 15
<212> TYPE: PRT
<213> ORGANISM: Zea mays

<400> SEQUENCE: 141

Cys Gly Cys Gln Pro Pro Pro Val His Leu Pro Pro Pro Pro Val
1               5                   10                  15

<210> SEQ ID NO 142
<211> LENGTH: 15
<212> TYPE: PRT
<213> ORGANISM: Zea mays

<400> SEQUENCE: 142

His Leu Pro Pro Pro Val His Leu Pro Pro Pro Val His Leu Pro
1               5                   10                  15

<210> SEQ ID NO 143
<211> LENGTH: 15
<212> TYPE: PRT
<213> ORGANISM: Zea mays

<400> SEQUENCE: 143

Pro Pro Val His Leu Pro Pro Pro Val His Leu Pro Pro Pro Val
1               5                   10                  15

<210> SEQ ID NO 144
<211> LENGTH: 15
```

```
<212> TYPE: PRT
<213> ORGANISM: Zea mays

<400> SEQUENCE: 144

His Val Pro Pro Val His Leu Pro Pro Pro Cys His Tyr
1               5                   10                  15

<210> SEQ ID NO 145
<211> LENGTH: 15
<212> TYPE: PRT
<213> ORGANISM: Zea mays

<400> SEQUENCE: 145

Pro Thr Gln Pro Pro Arg Pro Gln Pro His Pro Gln Pro His Pro
1               5                   10                  15

<210> SEQ ID NO 146
<211> LENGTH: 15
<212> TYPE: PRT
<213> ORGANISM: Zea mays

<400> SEQUENCE: 146

Cys Pro Cys Gln Gln Pro His Pro Ser Pro Cys Gln Leu Gln Gly
1               5                   10                  15

<210> SEQ ID NO 147
<211> LENGTH: 15
<212> TYPE: PRT
<213> ORGANISM: Zea mays

<400> SEQUENCE: 147

Thr Cys Gly Val Gly Ser Thr Pro Ile Leu Gly Gln Cys Val Glu
1               5                   10                  15

<210> SEQ ID NO 148
<211> LENGTH: 15
<212> TYPE: PRT
<213> ORGANISM: Zea mays

<400> SEQUENCE: 148

Phe Leu Arg His Gln Cys Ser Pro Thr Ala Thr Pro Tyr Cys Ser
1               5                   10                  15

<210> SEQ ID NO 149
<211> LENGTH: 15
<212> TYPE: PRT
<213> ORGANISM: Zea mays

<400> SEQUENCE: 149

Pro Gln Cys Gln Ser Leu Arg Gln Gln Cys Cys Gln Gln Leu Arg
1               5                   10                  15

<210> SEQ ID NO 150
<211> LENGTH: 15
<212> TYPE: PRT
<213> ORGANISM: Zea mays

<400> SEQUENCE: 150

Gln Val Glu Pro Gln His Arg Tyr Gln Ala Ile Phe Gly Leu Val
1               5                   10                  15

<210> SEQ ID NO 151
<211> LENGTH: 15
<212> TYPE: PRT
<213> ORGANISM: Zea mays
```

```
<400> SEQUENCE: 151

Leu Gln Ser Ile Leu Gln Gln Gln Pro Gln Ser Gly Gln Val Ala
1               5                   10                  15

<210> SEQ ID NO 152
<211> LENGTH: 15
<212> TYPE: PRT
<213> ORGANISM: Zea mays

<400> SEQUENCE: 152

Gly Leu Leu Ala Ala Gln Ile Ala Gln Gln Leu Thr Ala Met Cys
1               5                   10                  15

<210> SEQ ID NO 153
<211> LENGTH: 15
<212> TYPE: PRT
<213> ORGANISM: Zea mays

<400> SEQUENCE: 153

Gly Leu Gln Gln Pro Thr Pro Cys Pro Tyr Ala Ala Ala Gly Gly
1               5                   10                  15

<210> SEQ ID NO 154
<211> LENGTH: 25
<212> TYPE: PRT
<213> ORGANISM: Zea mays

<400> SEQUENCE: 154

Pro Thr Gln Pro Pro Arg Pro Gln Pro His Pro Gln Pro His Pro Cys
1               5                   10                  15

Pro Cys Gln Gln Pro His Pro Ser Pro
            20                  25

<210> SEQ ID NO 155
<211> LENGTH: 20
<212> TYPE: PRT
<213> ORGANISM: Zea mays

<400> SEQUENCE: 155

Arg Pro Gln Pro His Pro Gln Pro His Pro Cys Pro Cys Gln Gln Pro
1               5                   10                  15

His Pro Ser Pro
            20

<210> SEQ ID NO 156
<211> LENGTH: 255
<212> TYPE: DNA
<213> ORGANISM: artificial sequence
<220> FEATURE:
<223> OTHER INFORMATION: chimeric gene encoding fusion peptide
<220> FEATURE:
<221> NAME/KEY: CDS
<222> LOCATION: (1)..(255)

<400> SEQUENCE: 156 atg cgt gtg ctg ctg gtg gcg ctg gcg ctg ctg gcg ctg gcg gcg gga      48
Met Arg Val Leu Leu Val Ala Leu Ala Leu Leu Ala Leu Ala Ala Gly
1               5                   10                  15 tcc atc gat cca cgt ttc cac gaa aac tgg ccg tct gcc ggc ggt acc      96
Ser Ile Asp Pro Arg Phe His Glu Asn Trp Pro Ser Ala Gly Gly Thr
            20                  25                  30 tct act tcc aaa gct tcc acc act acg act tct agc aaa acc acc act     144
Ser Thr Ser Lys Ala Ser Thr Thr Thr Thr Ser Ser Lys Thr Thr Thr
```

```
aca tcc tct aag act acc acg act acc tcc aaa acc tct act acc tct      192
Thr Ser Ser Lys Thr Thr Thr Thr Thr Ser Lys Thr Ser Thr Thr Ser
    50                  55                  60 agc tcc tct acg ggc ggc gcc act cac aag acc tct act cag cgt ctg      240
Ser Ser Ser Thr Gly Gly Ala Thr His Lys Thr Ser Thr Gln Arg Leu
65                  70                  75                  80 ctg gct gca taa tga                                                  255
Leu Ala Ala <210> SEQ ID NO 157
<211> LENGTH: 83
<212> TYPE: PRT
<213> ORGANISM: artificial sequence
<220> FEATURE:
<223> OTHER INFORMATION: Synthetic Construct

<400> SEQUENCE: 157

Met Arg Val Leu Leu Val Ala Leu Ala Leu Leu Ala Leu Ala Ala Gly
1               5                   10                  15

Ser Ile Asp Pro Arg Phe His Glu Asn Trp Pro Ser Ala Gly Gly Thr
            20                  25                  30

Ser Thr Ser Lys Ala Ser Thr Thr Thr Thr Ser Ser Lys Thr Thr Thr
        35                  40                  45

Thr Ser Ser Lys Thr Thr Thr Thr Thr Ser Lys Thr Ser Thr Thr Ser
    50                  55                  60

Ser Ser Ser Thr Gly Gly Ala Thr His Lys Thr Ser Thr Gln Arg Leu
65                  70                  75                  80

Leu Ala Ala

<210> SEQ ID NO 158
<211> LENGTH: 258
<212> TYPE: DNA
<213> ORGANISM: artificial sequence
<220> FEATURE:
<223> OTHER INFORMATION: chimeric gene encoding fusion peptide
<220> FEATURE:
<221> NAME/KEY: CDS
<222> LOCATION: (1)..(258)

<400> SEQUENCE: 158 atg agc gcg acc agc acc cac acc agc ggt ggt tgc ggt tgc cag ccg       48
Met Ser Ala Thr Ser Thr His Thr Ser Gly Gly Cys Gly Cys Gln Pro
1               5                   10                  15 gga tcc atc gat cca cgt ttc cac gaa aac tgg ccg tct gcc ggc ggt       96
Gly Ser Ile Asp Pro Arg Phe His Glu Asn Trp Pro Ser Ala Gly Gly
            20                  25                  30 acc tct act tcc aaa gct tcc acc act acg act tct agc aaa acc acc      144
Thr Ser Thr Ser Lys Ala Ser Thr Thr Thr Thr Ser Ser Lys Thr Thr
        35                  40                  45 act aca tcc tct aag act acc acg act acc tcc aaa acc tct act acc      192
Thr Thr Ser Ser Lys Thr Thr Thr Thr Thr Ser Lys Thr Ser Thr Thr
    50                  55                  60 tct agc tcc tct acg ggc ggc gcc act cac aag acc tct act cag cgt      240
Ser Ser Ser Ser Thr Gly Gly Ala Thr His Lys Thr Ser Thr Gln Arg
65                  70                  75                  80 ctg ctg gct gca taa tga                                              258
Leu Leu Ala Ala

<210> SEQ ID NO 159
<211> LENGTH: 84
```

```
<212> TYPE: PRT
<213> ORGANISM: artificial sequence
<220> FEATURE:
<223> OTHER INFORMATION: Synthetic Construct

<400> SEQUENCE: 159

Met Ser Ala Thr Ser Thr His Thr Ser Gly Gly Cys Gly Cys Gln Pro
1               5                   10                  15

Gly Ser Ile Asp Pro Arg Phe His Glu Asn Trp Pro Ser Ala Gly Gly
            20                  25                  30

Thr Ser Thr Ser Lys Ala Ser Thr Thr Thr Ser Ser Lys Thr Thr
        35                  40                  45

Thr Thr Ser Ser Lys Thr Thr Thr Thr Ser Lys Thr Ser Thr Thr
    50                  55                  60

Ser Ser Ser Ser Thr Gly Gly Ala Thr His Lys Thr Ser Thr Gln Arg
65                  70                  75                  80

Leu Leu Ala Ala

<210> SEQ ID NO 160
<211> LENGTH: 258
<212> TYPE: DNA
<213> ORGANISM: artificial sequence
<220> FEATURE:
<223> OTHER INFORMATION: chimeric gene encoding fusion peptide
<220> FEATURE:
<221> NAME/KEY: CDS
<222> LOCATION: (1)..(258)

<400> SEQUENCE: 160 atg ccg ccg ccg gtg cac ctg ccg ccg ccg gtg cac ctg ccg ccg ccg        48
Met Pro Pro Pro Val His Leu Pro Pro Pro Val His Leu Pro Pro Pro
1               5                   10                  15 gga tcc atc gat cca cgt ttc cac gaa aac tgg ccg tct gcc ggc ggt        96
Gly Ser Ile Asp Pro Arg Phe His Glu Asn Trp Pro Ser Ala Gly Gly
            20                  25                  30 acc tct act tcc aaa gct tcc acc act acg act tct agc aaa acc acc       144
Thr Ser Thr Ser Lys Ala Ser Thr Thr Thr Thr Ser Ser Lys Thr Thr
        35                  40                  45 act aca tcc tct aag act acc acg act acc tcc aaa acc tct act acc       192
Thr Thr Ser Ser Lys Thr Thr Thr Thr Ser Lys Thr Ser Thr Thr
    50                  55                  60 tct agc tcc tct acg ggc ggc gcc act cac aag acc tct act cag cgt       240
Ser Ser Ser Ser Thr Gly Gly Ala Thr His Lys Thr Ser Thr Gln Arg
65                  70                  75                  80 ctg ctg gct gca taa tga                                                258
Leu Leu Ala Ala <210> SEQ ID NO 161
<211> LENGTH: 84
<212> TYPE: PRT
<213> ORGANISM: artificial sequence
<220> FEATURE:
<223> OTHER INFORMATION: Synthetic Construct

<400> SEQUENCE: 161

Met Pro Pro Pro Val His Leu Pro Pro Pro Val His Leu Pro Pro Pro
1               5                   10                  15

Gly Ser Ile Asp Pro Arg Phe His Glu Asn Trp Pro Ser Ala Gly Gly
            20                  25                  30

Thr Ser Thr Ser Lys Ala Ser Thr Thr Thr Thr Ser Ser Lys Thr Thr
        35                  40                  45
```

```
Thr Thr Ser Ser Lys Thr Thr Thr Thr Ser Lys Thr Ser Thr Thr
         50                  55                  60

Ser Ser Ser Ser Thr Gly Gly Ala Thr His Lys Thr Ser Thr Gln Arg
 65                  70                  75                  80

Leu Leu Ala Ala

<210> SEQ ID NO 162
<211> LENGTH: 258
<212> TYPE: DNA
<213> ORGANISM: artificial sequence
<220> FEATURE:
<223> OTHER INFORMATION: chimeric gene encoding fusion peptide
<220> FEATURE:
<221> NAME/KEY: CDS
<222> LOCATION: (1)..(258)

<400> SEQUENCE: 162 atg gtg cac ctg ccg ccg gtg cac ctg ccg ccg gtg cac ctg              48
Met Val His Leu Pro Pro Val His Leu Pro Pro Val His Leu
 1               5                  10                  15 gga tcc atc gat cca cgt ttc cac gaa aac tgg ccg tct gcc ggc ggt      96
Gly Ser Ile Asp Pro Arg Phe His Glu Asn Trp Pro Ser Ala Gly Gly
             20                  25                  30 acc tct act tcc aaa gct tcc acc act acg act tct agc aaa acc acc    144
Thr Ser Thr Ser Lys Ala Ser Thr Thr Thr Thr Ser Ser Lys Thr Thr
         35                  40                  45 act aca tcc tct aag act acc acg act acc tcc aaa acc tct act acc    192
Thr Thr Ser Ser Lys Thr Thr Thr Thr Thr Ser Lys Thr Ser Thr Thr
         50                  55                  60 tct agc tcc tct acg ggc ggc gcc act cac aag acc tct act cag cgt    240
Ser Ser Ser Ser Thr Gly Gly Ala Thr His Lys Thr Ser Thr Gln Arg
 65                  70                  75                  80 ctg ctg gct gca taa tga                                             258
Leu Leu Ala Ala <210> SEQ ID NO 163
<211> LENGTH: 84
<212> TYPE: PRT
<213> ORGANISM: artificial sequence
<220> FEATURE:
<223> OTHER INFORMATION: Synthetic Construct

<400> SEQUENCE: 163

Met Val His Leu Pro Pro Val His Leu Pro Pro Val His Leu
 1               5                  10                  15

Gly Ser Ile Asp Pro Arg Phe His Glu Asn Trp Pro Ser Ala Gly Gly
             20                  25                  30

Thr Ser Thr Ser Lys Ala Ser Thr Thr Thr Ser Ser Lys Thr Thr
         35                  40                  45

Thr Thr Ser Ser Lys Thr Thr Thr Thr Thr Ser Lys Thr Ser Thr Thr
         50                  55                  60

Ser Ser Ser Ser Thr Gly Gly Ala Thr His Lys Thr Ser Thr Gln Arg
 65                  70                  75                  80

Leu Leu Ala Ala

<210> SEQ ID NO 164
<211> LENGTH: 258
<212> TYPE: DNA
<213> ORGANISM: artificial sequence
<220> FEATURE:
<223> OTHER INFORMATION: chimeric gene encoding fusion peptide
<220> FEATURE:
```

```
<221> NAME/KEY: CDS
<222> LOCATION: (1)..(258)

<400> SEQUENCE: 164 atg ccg ccg ccg gtg cac ctg ccg ccg ccg gtg cac gtg ccg ccg ccg      48
Met Pro Pro Pro Val His Leu Pro Pro Pro Val His Val Pro Pro Pro
1               5                   10                  15 gga tcc atc gat cca cgt ttc cac gaa aac tgg ccg tct gcc ggc ggt      96
Gly Ser Ile Asp Pro Arg Phe His Glu Asn Trp Pro Ser Ala Gly Gly
            20                  25                  30 acc tct act tcc aaa gct tcc acc act acg act tct agc aaa acc acc     144
Thr Ser Thr Ser Lys Ala Ser Thr Thr Thr Thr Ser Ser Lys Thr Thr
        35                  40                  45 act aca tcc tct aag act acc acg act acc tcc aaa acc tct act acc     192
Thr Thr Ser Ser Lys Thr Thr Thr Thr Thr Ser Lys Thr Ser Thr Thr
    50                  55                  60 tct agc tcc tct acg ggc ggc gcc act cac aag acc tct act cag cgt     240
Ser Ser Ser Ser Thr Gly Gly Ala Thr His Lys Thr Ser Thr Gln Arg
65                  70                  75                  80 ctg ctg gct gca taa tga                                             258
Leu Leu Ala Ala <210> SEQ ID NO 165
<211> LENGTH: 84
<212> TYPE: PRT
<213> ORGANISM: artificial sequence
<220> FEATURE:
<223> OTHER INFORMATION: Synthetic Construct

<400> SEQUENCE: 165

Met Pro Pro Pro Val His Leu Pro Pro Pro Val His Val Pro Pro Pro
1               5                   10                  15

Gly Ser Ile Asp Pro Arg Phe His Glu Asn Trp Pro Ser Ala Gly Gly
            20                  25                  30

Thr Ser Thr Ser Lys Ala Ser Thr Thr Thr Thr Ser Ser Lys Thr Thr
        35                  40                  45

Thr Thr Ser Ser Lys Thr Thr Thr Thr Thr Ser Lys Thr Ser Thr Thr
    50                  55                  60

Ser Ser Ser Ser Thr Gly Gly Ala Thr His Lys Thr Ser Thr Gln Arg
65                  70                  75                  80

Leu Leu Ala Ala

<210> SEQ ID NO 166
<211> LENGTH: 258
<212> TYPE: DNA
<213> ORGANISM: artificial sequence
<220> FEATURE:
<223> OTHER INFORMATION: chimeric gene encoding fusion peptide
<220> FEATURE:
<221> NAME/KEY: CDS
<222> LOCATION: (1)..(258)

<400> SEQUENCE: 166 atg gtg cac ctg ccg ccg ccg tgc cac tac ccg acc cag ccg ccg          48
Met Val His Leu Pro Pro Pro Cys His Tyr Pro Thr Gln Pro Pro
1               5                   10                  15 gga tcc atc gat cca cgt ttc cac gaa aac tgg ccg tct gcc ggc ggt      96
Gly Ser Ile Asp Pro Arg Phe His Glu Asn Trp Pro Ser Ala Gly Gly
            20                  25                  30 acc tct act tcc aaa gct tcc acc act acg act tct agc aaa acc acc     144
Thr Ser Thr Ser Lys Ala Ser Thr Thr Thr Thr Ser Ser Lys Thr Thr
        35                  40                  45
```

```
act aca tcc tct aag act acc acg act acc tcc aaa acc tct act acc      192
Thr Thr Ser Ser Lys Thr Thr Thr Thr Thr Ser Lys Thr Ser Thr Thr
    50                  55                  60 tct agc tcc tct acg ggc ggc gcc act cac aag acc tct act cag cgt      240
Ser Ser Ser Ser Thr Gly Gly Ala Thr His Lys Thr Ser Thr Gln Arg
65                  70                  75                  80 ctg ctg gct gca taa tga                                              258
Leu Leu Ala Ala
```

<210> SEQ ID NO 167
<211> LENGTH: 84
<212> TYPE: PRT
<213> ORGANISM: artificial sequence
<220> FEATURE:
<223> OTHER INFORMATION: Synthetic Construct

<400> SEQUENCE: 167

```
Met Val His Leu Pro Pro Pro Cys His Tyr Pro Thr Gln Pro Pro
1               5                   10                  15

Gly Ser Ile Asp Pro Arg Phe His Glu Asn Trp Pro Ser Ala Gly Gly
                20                  25                  30

Thr Ser Thr Ser Lys Ala Ser Thr Thr Thr Ser Ser Lys Thr Thr
            35                  40                  45

Thr Thr Ser Ser Lys Thr Thr Thr Thr Ser Lys Thr Ser Thr Thr
    50                  55                  60

Ser Ser Ser Ser Thr Gly Gly Ala Thr His Lys Thr Ser Thr Gln Arg
65                  70                  75                  80

Leu Leu Ala Ala
```

<210> SEQ ID NO 168
<211> LENGTH: 258
<212> TYPE: DNA
<213> ORGANISM: artificial sequence
<220> FEATURE:
<223> OTHER INFORMATION: chimeric gene encoding fusion peptide
<220> FEATURE:
<221> NAME/KEY: CDS
<222> LOCATION: (1)..(258)

<400> SEQUENCE: 168

```
atg cgt ccg cag ccg cac ccg cag ccg cac ccg tgc ccg tgc cag cag       48
Met Arg Pro Gln Pro His Pro Gln Pro His Pro Cys Pro Cys Gln Gln
1               5                   10                  15 gga tcc atc gat cca cgt ttc cac gaa aac tgg ccg tct gcc ggc ggt       96
Gly Ser Ile Asp Pro Arg Phe His Glu Asn Trp Pro Ser Ala Gly Gly
                20                  25                  30 acc tct act tcc aaa gct tcc acc act acg act tct agc aaa acc acc      144
Thr Ser Thr Ser Lys Ala Ser Thr Thr Thr Ser Ser Lys Thr Thr
            35                  40                  45 act aca tcc tct aag act acc acg act acc tcc aaa acc tct act acc      192
Thr Thr Ser Ser Lys Thr Thr Thr Thr Ser Lys Thr Ser Thr Thr
    50                  55                  60 tct agc tcc tct acg ggc ggc gcc act cac aag acc tct act cag cgt      240
Ser Ser Ser Ser Thr Gly Gly Ala Thr His Lys Thr Ser Thr Gln Arg
65                  70                  75                  80 ctg ctg gct gca taa tga                                              258
Leu Leu Ala Ala
```

<210> SEQ ID NO 169
<211> LENGTH: 84
<212> TYPE: PRT

<213> ORGANISM: artificial sequence
<220> FEATURE:
<223> OTHER INFORMATION: Synthetic Construct

<400> SEQUENCE: 169

Met Arg Pro Gln Pro His Pro Gln Pro His Pro Cys Pro Cys Gln Gln
1               5                   10                  15

Gly Ser Ile Asp Pro Arg Phe His Glu Asn Trp Pro Ser Ala Gly Gly
            20                  25                  30

Thr Ser Thr Ser Lys Ala Ser Thr Thr Thr Ser Ser Lys Thr Thr
        35                  40                  45

Thr Thr Ser Ser Lys Thr Thr Thr Thr Ser Lys Thr Ser Thr Thr
    50                  55                  60

Ser Ser Ser Ser Thr Gly Gly Ala Thr His Lys Thr Ser Thr Gln Arg
65                  70                  75                  80

Leu Leu Ala Ala

<210> SEQ ID NO 170
<211> LENGTH: 258
<212> TYPE: DNA
<213> ORGANISM: artificial sequence
<220> FEATURE:
<223> OTHER INFORMATION: chimeric gene encoding fusion peptide
<220> FEATURE:
<221> NAME/KEY: CDS
<222> LOCATION: (1)..(258)

<400> SEQUENCE: 170 atg ccg cac ccg agc ccg tgc cag ctg cag ggg acc tgc ggt gtg ggt     48
Met Pro His Pro Ser Pro Cys Gln Leu Gln Gly Thr Cys Gly Val Gly
1               5                   10                  15 gga tcc atc gat cca cgt ttc cac gaa aac tgg ccg tct gcc ggc ggt     96
Gly Ser Ile Asp Pro Arg Phe His Glu Asn Trp Pro Ser Ala Gly Gly
            20                  25                  30 acc tct act tcc aaa gct tcc acc act acg act tct agc aaa acc acc    144
Thr Ser Thr Ser Lys Ala Ser Thr Thr Thr Ser Ser Lys Thr Thr
        35                  40                  45 act aca tcc tct aag act acc acg act acc tcc aaa acc tct act acc    192
Thr Thr Ser Ser Lys Thr Thr Thr Thr Ser Lys Thr Ser Thr Thr
    50                  55                  60 tct agc tcc tct acg ggc ggc gcc act cac aag acc tct act cag cgt    240
Ser Ser Ser Ser Thr Gly Gly Ala Thr His Lys Thr Ser Thr Gln Arg
65                  70                  75                  80 ctg ctg gct gca taa tga                                            258
Leu Leu Ala Ala <210> SEQ ID NO 171
<211> LENGTH: 84
<212> TYPE: PRT
<213> ORGANISM: artificial sequence
<220> FEATURE:
<223> OTHER INFORMATION: Synthetic Construct

<400> SEQUENCE: 171

Met Pro His Pro Ser Pro Cys Gln Leu Gln Gly Thr Cys Gly Val Gly
1               5                   10                  15

Gly Ser Ile Asp Pro Arg Phe His Glu Asn Trp Pro Ser Ala Gly Gly
            20                  25                  30

Thr Ser Thr Ser Lys Ala Ser Thr Thr Thr Ser Ser Lys Thr Thr
        35                  40                  45

Thr Thr Ser Ser Lys Thr Thr Thr Thr Ser Lys Thr Ser Thr Thr

```
                    50                  55                  60
Ser Ser Ser Ser Thr Gly Gly Ala Thr His Lys Thr Ser Thr Gln Arg
 65                  70                  75                  80

Leu Leu Ala Ala
```

<210> SEQ ID NO 172
<211> LENGTH: 258
<212> TYPE: DNA
<213> ORGANISM: artificial sequence
<220> FEATURE:
<223> OTHER INFORMATION: chimeric gene encoding fusion peptide
<220> FEATURE:
<221> NAME/KEY: CDS
<222> LOCATION: (1)..(258)

<400> SEQUENCE: 172

```
atg agc acc ccg atc ctg ggt cag tgc gtg gaa ttc ctg cgt cac cag     48
Met Ser Thr Pro Ile Leu Gly Gln Cys Val Glu Phe Leu Arg His Gln
 1               5                  10                  15 gga tcc atc gat cca cgt ttc cac gaa aac tgg ccg tct gcc ggc ggt     96
Gly Ser Ile Asp Pro Arg Phe His Glu Asn Trp Pro Ser Ala Gly Gly
             20                  25                  30 acc tct act tcc aaa gct tcc acc act acg act tct agc aaa acc acc    144
Thr Ser Thr Ser Lys Ala Ser Thr Thr Thr Thr Ser Ser Lys Thr Thr
         35                  40                  45 act aca tcc tct aag act acc acg act acc tcc aaa acc tct act acc    192
Thr Thr Ser Ser Lys Thr Thr Thr Thr Thr Ser Lys Thr Ser Thr Thr
     50                  55                  60 tct agc tcc tct acg ggc ggc gcc act cac aag acc tct act cag cgt    240
Ser Ser Ser Ser Thr Gly Gly Ala Thr His Lys Thr Ser Thr Gln Arg
 65                  70                  75                  80 ctg ctg gct gca taa tga                                            258
Leu Leu Ala Ala
```

<210> SEQ ID NO 173
<211> LENGTH: 84
<212> TYPE: PRT
<213> ORGANISM: artificial sequence
<220> FEATURE:
<223> OTHER INFORMATION: Synthetic Construct

<400> SEQUENCE: 173

```
Met Ser Thr Pro Ile Leu Gly Gln Cys Val Glu Phe Leu Arg His Gln
 1               5                  10                  15

Gly Ser Ile Asp Pro Arg Phe His Glu Asn Trp Pro Ser Ala Gly Gly
             20                  25                  30

Thr Ser Thr Ser Lys Ala Ser Thr Thr Thr Ser Ser Lys Thr Thr
         35                  40                  45

Thr Thr Ser Ser Lys Thr Thr Thr Thr Thr Ser Lys Thr Ser Thr Thr
     50                  55                  60

Ser Ser Ser Ser Thr Gly Gly Ala Thr His Lys Thr Ser Thr Gln Arg
 65                  70                  75                  80

Leu Leu Ala Ala
```

<210> SEQ ID NO 174
<211> LENGTH: 258
<212> TYPE: DNA
<213> ORGANISM: artificial sequence
<220> FEATURE:
<223> OTHER INFORMATION: chimeric gene encoding fusion peptide
<220> FEATURE:
<221> NAME/KEY: CDS -continued

<222> LOCATION: (1)..(258)

<400> SEQUENCE: 174

```
atg tgc agc ccg acc gcg acc ccg tac tgc agc ccg cag tgc cag agc      48
Met Cys Ser Pro Thr Ala Thr Pro Tyr Cys Ser Pro Gln Cys Gln Ser
1               5                   10                  15 gga tcc atc gat cca cgt ttc cac gaa aac tgg ccg tct gcc ggc ggt      96
Gly Ser Ile Asp Pro Arg Phe His Glu Asn Trp Pro Ser Ala Gly Gly
            20                  25                  30 acc tct act tcc aaa gct tcc acc act acg act tct agc aaa acc acc    144
Thr Ser Thr Ser Lys Ala Ser Thr Thr Thr Thr Ser Ser Lys Thr Thr
        35                  40                  45 act aca tcc tct aag act acc acg act acc tcc aaa acc tct act acc    192
Thr Thr Ser Ser Lys Thr Thr Thr Thr Thr Ser Lys Thr Ser Thr Thr
    50                  55                  60 tct agc tcc tct acg ggc ggc gcc act cac aag acc tct act cag cgt    240
Ser Ser Ser Ser Thr Gly Gly Ala Thr His Lys Thr Ser Thr Gln Arg
65                  70                  75                  80 ctg ctg gct gca taa tga                                              258
Leu Leu Ala Ala
```

<210> SEQ ID NO 175
<211> LENGTH: 84
<212> TYPE: PRT
<213> ORGANISM: artificial sequence
<220> FEATURE:
<223> OTHER INFORMATION: Synthetic Construct

<400> SEQUENCE: 175

```
Met Cys Ser Pro Thr Ala Thr Pro Tyr Cys Ser Pro Gln Cys Gln Ser
1               5                   10                  15

Gly Ser Ile Asp Pro Arg Phe His Glu Asn Trp Pro Ser Ala Gly Gly
            20                  25                  30

Thr Ser Thr Ser Lys Ala Ser Thr Thr Thr Thr Ser Ser Lys Thr Thr
        35                  40                  45

Thr Thr Ser Ser Lys Thr Thr Thr Thr Thr Ser Lys Thr Ser Thr Thr
    50                  55                  60

Ser Ser Ser Ser Thr Gly Gly Ala Thr His Lys Thr Ser Thr Gln Arg
65                  70                  75                  80

Leu Leu Ala Ala
```

<210> SEQ ID NO 176
<211> LENGTH: 258
<212> TYPE: DNA
<213> ORGANISM: artificial sequence
<220> FEATURE:
<223> OTHER INFORMATION: chimeric gene encoding fusion peptide
<220> FEATURE:
<221> NAME/KEY: CDS
<222> LOCATION: (1)..(258)

<400> SEQUENCE: 176

```
atg ctg cgt cag cag tgc tgc cag cag ctg cgt cag gtg gaa ccg cag      48
Met Leu Arg Gln Gln Cys Cys Gln Gln Leu Arg Gln Val Glu Pro Gln
1               5                   10                  15 gga tcc atc gat cca cgt ttc cac gaa aac tgg ccg tct gcc ggc ggt      96
Gly Ser Ile Asp Pro Arg Phe His Glu Asn Trp Pro Ser Ala Gly Gly
            20                  25                  30 acc tct act tcc aaa gct tcc acc act acg act tct agc aaa acc acc    144
Thr Ser Thr Ser Lys Ala Ser Thr Thr Thr Thr Ser Ser Lys Thr Thr
        35                  40                  45
```

```
act aca tcc tct aag act acc acg act acc tcc aaa acc tct act acc      192
Thr Thr Ser Ser Lys Thr Thr Thr Thr Thr Ser Lys Thr Ser Thr Thr
     50                  55                  60 tct agc tcc tct acg ggc ggc gcc act cac aag acc tct act cag cgt      240
Ser Ser Ser Ser Thr Gly Gly Ala Thr His Lys Thr Ser Thr Gln Arg
 65                  70                  75                  80 ctg ctg gct gca taa tga                                              258
Leu Leu Ala Ala
```

<210> SEQ ID NO 177
<211> LENGTH: 84
<212> TYPE: PRT
<213> ORGANISM: artificial sequence
<220> FEATURE:
<223> OTHER INFORMATION: Synthetic Construct

<400> SEQUENCE: 177

```
Met Leu Arg Gln Gln Cys Cys Gln Gln Leu Arg Gln Val Glu Pro Gln
 1               5                  10                  15

Gly Ser Ile Asp Pro Arg Phe His Glu Asn Trp Pro Ser Ala Gly Gly
                20                  25                  30

Thr Ser Thr Ser Lys Ala Ser Thr Thr Thr Ser Ser Lys Thr Thr
             35                  40                  45

Thr Thr Ser Ser Lys Thr Thr Thr Thr Thr Ser Lys Thr Ser Thr Thr
     50                  55                  60

Ser Ser Ser Ser Thr Gly Gly Ala Thr His Lys Thr Ser Thr Gln Arg
 65                  70                  75                  80

Leu Leu Ala Ala
```

<210> SEQ ID NO 178
<211> LENGTH: 258
<212> TYPE: DNA
<213> ORGANISM: artificial sequence
<220> FEATURE:
<223> OTHER INFORMATION: chimeric gene encoding fusion peptide
<220> FEATURE:
<221> NAME/KEY: CDS
<222> LOCATION: (1)..(258)

<400> SEQUENCE: 178

```
atg cac cgt tac cag gcg atc ttc ggt ctg gtg ctg cag agc atc ctg       48
Met His Arg Tyr Gln Ala Ile Phe Gly Leu Val Leu Gln Ser Ile Leu
 1               5                  10                  15 gga tcc atc gat cca cgt ttc cac gaa aac tgg ccg tct gcc ggc ggt       96
Gly Ser Ile Asp Pro Arg Phe His Glu Asn Trp Pro Ser Ala Gly Gly
                20                  25                  30 acc tct act tcc aaa gct tcc acc act acg act tct agc aaa acc acc      144
Thr Ser Thr Ser Lys Ala Ser Thr Thr Thr Ser Ser Lys Thr Thr
             35                  40                  45 act aca tcc tct aag act acc acg act acc tcc aaa acc tct act acc      192
Thr Thr Ser Ser Lys Thr Thr Thr Thr Thr Ser Lys Thr Ser Thr Thr
     50                  55                  60 tct agc tcc tct acg ggc ggc gcc act cac aag acc tct act cag cgt      240
Ser Ser Ser Ser Thr Gly Gly Ala Thr His Lys Thr Ser Thr Gln Arg
 65                  70                  75                  80 ctg ctg gct gca taa tga                                              258
Leu Leu Ala Ala
```

<210> SEQ ID NO 179
<211> LENGTH: 84
<212> TYPE: PRT
<213> ORGANISM: artificial sequence
<220> FEATURE:
<223> OTHER INFORMATION: Synthetic Construct

<400> SEQUENCE: 179

Met His Arg Tyr Gln Ala Ile Phe Gly Leu Val Leu Gln Ser Ile Leu
1               5                   10                  15

Gly Ser Ile Asp Pro Arg Phe His Glu Asn Trp Pro Ser Ala Gly Gly
                20                  25                  30

Thr Ser Thr Ser Lys Ala Ser Thr Thr Thr Ser Ser Lys Thr Thr
            35                  40                  45

Thr Thr Ser Ser Lys Thr Thr Thr Thr Ser Lys Thr Ser Thr Thr
    50                  55                  60

Ser Ser Ser Ser Thr Gly Gly Ala Thr His Lys Thr Ser Thr Gln Arg
65                  70                  75                  80

Leu Leu Ala Ala

<210> SEQ ID NO 180
<211> LENGTH: 258
<212> TYPE: DNA
<213> ORGANISM: artificial sequence
<220> FEATURE:
<223> OTHER INFORMATION: chimeric gene encoding fusion peptide
<220> FEATURE:
<221> NAME/KEY: CDS
<222> LOCATION: (1)..(258)

<400> SEQUENCE: 180 atg cag cag cag ccg cag agc ggt cag gtg gcg ggt ctg ctg gcg gcg     48
Met Gln Gln Gln Pro Gln Ser Gly Gln Val Ala Gly Leu Leu Ala Ala
1               5                   10                  15 gga tcc atc gat cca cgt ttc cac gaa aac tgg ccg tct gcc ggc ggt     96
Gly Ser Ile Asp Pro Arg Phe His Glu Asn Trp Pro Ser Ala Gly Gly
                20                  25                  30 acc tct act tcc aaa gct tcc acc act acg act tct agc aaa acc acc    144
Thr Ser Thr Ser Lys Ala Ser Thr Thr Thr Thr Ser Ser Lys Thr Thr
            35                  40                  45 act aca tcc tct aag act acc acg act acc tcc aaa acc tct act acc    192
Thr Thr Ser Ser Lys Thr Thr Thr Thr Ser Lys Thr Ser Thr Thr
    50                  55                  60 tct agc tcc tct acg ggc ggc gcc act cac aag acc tct act cag cgt    240
Ser Ser Ser Ser Thr Gly Gly Ala Thr His Lys Thr Ser Thr Gln Arg
65                  70                  75                  80 ctg ctg gct gca taa tga                                             258
Leu Leu Ala Ala <210> SEQ ID NO 181
<211> LENGTH: 84
<212> TYPE: PRT
<213> ORGANISM: artificial sequence
<220> FEATURE:
<223> OTHER INFORMATION: Synthetic Construct

<400> SEQUENCE: 181

Met Gln Gln Gln Pro Gln Ser Gly Gln Val Ala Gly Leu Leu Ala Ala
1               5                   10                  15

Gly Ser Ile Asp Pro Arg Phe His Glu Asn Trp Pro Ser Ala Gly Gly
                20                  25                  30

Thr Ser Thr Ser Lys Ala Ser Thr Thr Thr Thr Ser Ser Lys Thr Thr
            35                  40                  45

Thr Thr Ser Ser Lys Thr Thr Thr Thr Ser Lys Thr Ser Thr Thr
    50                  55                  60

```
Ser Ser Ser Ser Thr Gly Gly Ala Thr His Lys Thr Ser Thr Gln Arg
65                  70                  75                  80

Leu Leu Ala Ala
```

<210> SEQ ID NO 182
<211> LENGTH: 258
<212> TYPE: DNA
<213> ORGANISM: artificial sequence
<220> FEATURE:
<223> OTHER INFORMATION: chimeric gene encoding fusion peptide
<220> FEATURE:
<221> NAME/KEY: CDS
<222> LOCATION: (1)..(258)

<400> SEQUENCE: 182

```
atg cag atc gcg cag cag ctg acc gcg atg tgc ggt ctg cag cag ccg      48
Met Gln Ile Ala Gln Gln Leu Thr Ala Met Cys Gly Leu Gln Gln Pro
1               5                   10                  15 gga tcc atc gat cca cgt ttc cac gaa aac tgg ccg tct gcc ggc ggt      96
Gly Ser Ile Asp Pro Arg Phe His Glu Asn Trp Pro Ser Ala Gly Gly
            20                  25                  30 acc tct act tcc aaa gct tcc acc act acg act tct agc aaa acc acc     144
Thr Ser Thr Ser Lys Ala Ser Thr Thr Thr Thr Ser Ser Lys Thr Thr
        35                  40                  45 act aca tcc tct aag act acc acg act acc tcc aaa acc tct act acc     192
Thr Thr Ser Ser Lys Thr Thr Thr Thr Thr Ser Lys Thr Ser Thr Thr
    50                  55                  60 tct agc tcc tct acg ggc ggc gcc act cac aag acc tct act cag cgt     240
Ser Ser Ser Ser Thr Gly Gly Ala Thr His Lys Thr Ser Thr Gln Arg
65                  70                  75                  80 ctg ctg gct gca taa tga                                             258
Leu Leu Ala Ala
```

<210> SEQ ID NO 183
<211> LENGTH: 84
<212> TYPE: PRT
<213> ORGANISM: artificial sequence
<220> FEATURE:
<223> OTHER INFORMATION: Synthetic Construct

<400> SEQUENCE: 183

```
Met Gln Ile Ala Gln Gln Leu Thr Ala Met Cys Gly Leu Gln Gln Pro
1               5                   10                  15

Gly Ser Ile Asp Pro Arg Phe His Glu Asn Trp Pro Ser Ala Gly Gly
            20                  25                  30

Thr Ser Thr Ser Lys Ala Ser Thr Thr Thr Thr Ser Ser Lys Thr Thr
        35                  40                  45

Thr Thr Ser Ser Lys Thr Thr Thr Thr Thr Ser Lys Thr Ser Thr Thr
    50                  55                  60

Ser Ser Ser Ser Thr Gly Gly Ala Thr His Lys Thr Ser Thr Gln Arg
65                  70                  75                  80

Leu Leu Ala Ala
```

<210> SEQ ID NO 184
<211> LENGTH: 252
<212> TYPE: DNA
<213> ORGANISM: artificial sequence
<220> FEATURE:
<223> OTHER INFORMATION: chimeric gene encoding fusion peptide
<220> FEATURE:
<221> NAME/KEY: CDS
<222> LOCATION: (1)..(252)

<400> SEQUENCE: 184

```
atg acc ccg tgc ccg tac gcg gcg gcg ggt ggt gtg ccg cac gga tcc      48
Met Thr Pro Cys Pro Tyr Ala Ala Ala Gly Gly Val Pro His Gly Ser
1               5                   10                  15 atc gat cca cgt ttc cac gaa aac tgg ccg tct gcc ggc ggt acc tct      96
Ile Asp Pro Arg Phe His Glu Asn Trp Pro Ser Ala Gly Gly Thr Ser
            20                  25                  30 act tcc aaa gct tcc acc act acg act tct agc aaa acc acc act aca     144
Thr Ser Lys Ala Ser Thr Thr Thr Thr Ser Ser Lys Thr Thr Thr Thr
        35                  40                  45 tcc tct aag act acc acg act acc tcc aaa acc tct act acc tct agc     192
Ser Ser Lys Thr Thr Thr Thr Thr Ser Lys Thr Ser Thr Thr Ser Ser
    50                  55                  60 tcc tct acg ggc ggc gcc act cac aag acc tct act cag cgt ctg ctg     240
Ser Ser Thr Gly Gly Ala Thr His Lys Thr Ser Thr Gln Arg Leu Leu
65                  70                  75                  80 gct gca taa tga                                                     252
Ala Ala
```

<210> SEQ ID NO 185
<211> LENGTH: 82
<212> TYPE: PRT
<213> ORGANISM: artificial sequence
<220> FEATURE:
<223> OTHER INFORMATION: Synthetic Construct

<400> SEQUENCE: 185

```
Met Thr Pro Cys Pro Tyr Ala Ala Ala Gly Gly Val Pro His Gly Ser
1               5                   10                  15

Ile Asp Pro Arg Phe His Glu Asn Trp Pro Ser Ala Gly Gly Thr Ser
            20                  25                  30

Thr Ser Lys Ala Ser Thr Thr Thr Thr Ser Ser Lys Thr Thr Thr Thr
        35                  40                  45

Ser Ser Lys Thr Thr Thr Thr Thr Ser Lys Thr Ser Thr Thr Ser Ser
    50                  55                  60

Ser Ser Thr Gly Gly Ala Thr His Lys Thr Ser Thr Gln Arg Leu Leu
65                  70                  75                  80

Ala Ala
```

<210> SEQ ID NO 186
<211> LENGTH: 258
<212> TYPE: DNA
<213> ORGANISM: artificial sequence
<220> FEATURE:
<223> OTHER INFORMATION: chimeric gene encoding fusion peptide
<220> FEATURE:
<221> NAME/KEY: CDS
<222> LOCATION: (1)..(258)

<400> SEQUENCE: 186

```
atg gtg gcg ctg gcg ctg ctg gcg ctg gcg gcg agc gcg acc agc acc      48
Met Val Ala Leu Ala Leu Leu Ala Leu Ala Ala Ser Ala Thr Ser Thr
1               5                   10                  15 gga tcc atc gat cca cgt ttc cac gaa aac tgg ccg tct gcc ggc ggt      96
Gly Ser Ile Asp Pro Arg Phe His Glu Asn Trp Pro Ser Ala Gly Gly
            20                  25                  30 acc tct act tcc aaa gct tcc acc act acg act tct agc aaa acc acc     144
Thr Ser Thr Ser Lys Ala Ser Thr Thr Thr Thr Ser Ser Lys Thr Thr
        35                  40                  45 act aca tcc tct aag act acc acg act acc tcc aaa acc tct act acc     192
```

```
Thr Thr Ser Ser Lys Thr Thr Thr Thr Thr Ser Lys Thr Ser Thr Thr
    50                  55                  60 tct agc tcc tct acg ggc ggc gcc act cac aag acc tct act cag cgt       240
Ser Ser Ser Ser Thr Gly Gly Ala Thr His Lys Thr Ser Thr Gln Arg
65                  70                  75                  80 ctg ctg gct gca taa tga                                                258
Leu Leu Ala Ala <210> SEQ ID NO 187
<211> LENGTH: 84
<212> TYPE: PRT
<213> ORGANISM: artificial sequence
<220> FEATURE:
<223> OTHER INFORMATION: Synthetic Construct

<400> SEQUENCE: 187

Met Val Ala Leu Ala Leu Leu Ala Leu Ala Ala Ser Ala Thr Ser Thr
1               5                   10                  15

Gly Ser Ile Asp Pro Arg Phe His Glu Asn Trp Pro Ser Ala Gly Gly
                20                  25                  30

Thr Ser Thr Ser Lys Ala Ser Thr Thr Thr Ser Ser Lys Thr Thr
            35                  40                  45

Thr Thr Ser Ser Lys Thr Thr Thr Thr Thr Ser Lys Thr Ser Thr Thr
    50                  55                  60

Ser Ser Ser Ser Thr Gly Gly Ala Thr His Lys Thr Ser Thr Gln Arg
65                  70                  75                  80

Leu Leu Ala Ala

<210> SEQ ID NO 188
<211> LENGTH: 258
<212> TYPE: DNA
<213> ORGANISM: artificial sequence
<220> FEATURE:
<223> OTHER INFORMATION: chimeric gene encoding fusion peptide
<220> FEATURE:
<221> NAME/KEY: CDS
<222> LOCATION: (1)..(258)

<400> SEQUENCE: 188 atg cac acc agc ggt ggt tgc ggt tgc cag ccg ccg ccg ccg gtg cac        48
Met His Thr Ser Gly Gly Cys Gly Cys Gln Pro Pro Pro Pro Val His
1               5                   10                  15 gga tcc atc gat cca cgt ttc cac gaa aac tgg ccg tct gcc ggc ggt        96
Gly Ser Ile Asp Pro Arg Phe His Glu Asn Trp Pro Ser Ala Gly Gly
                20                  25                  30 acc tct act tcc aaa gct tcc acc act acg act tct agc aaa acc acc       144
Thr Ser Thr Ser Lys Ala Ser Thr Thr Thr Thr Ser Ser Lys Thr Thr
            35                  40                  45 act aca tcc tct aag act acc acg act acc tcc aaa acc tct act acc       192
Thr Thr Ser Ser Lys Thr Thr Thr Thr Thr Ser Lys Thr Ser Thr Thr
    50                  55                  60 tct agc tcc tct acg ggc ggc gcc act cac aag acc tct act cag cgt       240
Ser Ser Ser Ser Thr Gly Gly Ala Thr His Lys Thr Ser Thr Gln Arg
65                  70                  75                  80 ctg ctg gct gca taa tga                                                258
Leu Leu Ala Ala <210> SEQ ID NO 189
<211> LENGTH: 84
<212> TYPE: PRT
<213> ORGANISM: artificial sequence
<220> FEATURE:
```

-continued

<223> OTHER INFORMATION: Synthetic Construct

<400> SEQUENCE: 189

Met His Thr Ser Gly Gly Cys Gly Cys Gln Pro Pro Pro Val His
1               5                   10                  15

Gly Ser Ile Asp Pro Arg Phe His Glu Asn Trp Pro Ser Ala Gly Gly
            20                  25                  30

Thr Ser Thr Ser Lys Ala Ser Thr Thr Thr Ser Ser Lys Thr Thr
        35                  40                  45

Thr Thr Ser Ser Lys Thr Thr Thr Thr Thr Ser Lys Thr Ser Thr Thr
50                  55                  60

Ser Ser Ser Ser Thr Gly Gly Ala Thr His Lys Thr Ser Thr Gln Arg
65                  70                  75                  80

Leu Leu Ala Ala

<210> SEQ ID NO 190
<211> LENGTH: 258
<212> TYPE: DNA
<213> ORGANISM: artificial sequence
<220> FEATURE:
<223> OTHER INFORMATION: chimeric gene encoding fusion peptide
<220> FEATURE:
<221> NAME/KEY: CDS
<222> LOCATION: (1)..(258)

<400> SEQUENCE: 190 atg ctg ccg ccg ccg gtg cac ctg ccg ccg ccg gtg cac ctg ccg ccg     48
Met Leu Pro Pro Pro Val His Leu Pro Pro Pro Val His Leu Pro Pro
1               5                   10                  15 gga tcc atc gat cca cgt ttc cac gaa aac tgg ccg tct gcc ggc ggt     96
Gly Ser Ile Asp Pro Arg Phe His Glu Asn Trp Pro Ser Ala Gly Gly
            20                  25                  30 acc tct act tcc aaa gct tcc acc act acg act tct agc aaa acc acc    144
Thr Ser Thr Ser Lys Ala Ser Thr Thr Thr Thr Ser Ser Lys Thr Thr
        35                  40                  45 act aca tcc tct aag act acc acg act acc tcc aaa acc tct act acc    192
Thr Thr Ser Ser Lys Thr Thr Thr Thr Thr Ser Lys Thr Ser Thr Thr
50                  55                  60 tct agc tcc tct acg ggc ggc gcc act cac aag acc tct act cag cgt    240
Ser Ser Ser Ser Thr Gly Gly Ala Thr His Lys Thr Ser Thr Gln Arg
65                  70                  75                  80 ctg ctg gct gca taa tga                                             258
Leu Leu Ala Ala <210> SEQ ID NO 191
<211> LENGTH: 84
<212> TYPE: PRT
<213> ORGANISM: artificial sequence
<220> FEATURE:
<223> OTHER INFORMATION: Synthetic Construct

<400> SEQUENCE: 191

Met Leu Pro Pro Pro Val His Leu Pro Pro Pro Val His Leu Pro Pro
1               5                   10                  15

Gly Ser Ile Asp Pro Arg Phe His Glu Asn Trp Pro Ser Ala Gly Gly
            20                  25                  30

Thr Ser Thr Ser Lys Ala Ser Thr Thr Thr Thr Ser Ser Lys Thr Thr
        35                  40                  45

Thr Thr Ser Ser Lys Thr Thr Thr Thr Thr Ser Lys Thr Ser Thr Thr
50                  55                  60

```
Ser Ser Ser Ser Thr Gly Gly Ala Thr His Lys Thr Ser Thr Gln Arg
 65                  70                  75                  80

Leu Leu Ala Ala
```

```
<210> SEQ ID NO 192
<211> LENGTH: 258
<212> TYPE: DNA
<213> ORGANISM: artificial sequence
<220> FEATURE:
<223> OTHER INFORMATION: chimeric gene encoding fusion peptide
<220> FEATURE:
<221> NAME/KEY: CDS
<222> LOCATION: (1)..(258)

<400> SEQUENCE: 192
```

```
atg ccg gtg cac ctg ccg ccg ccg gtg cac ctg ccg ccg gtg cac        48
Met Pro Val His Leu Pro Pro Pro Val His Leu Pro Pro Val His
 1               5                  10                  15 gga tcc atc gat cca cgt ttc cac gaa aac tgg ccg tct gcc ggc ggt    96
Gly Ser Ile Asp Pro Arg Phe His Glu Asn Trp Pro Ser Ala Gly Gly
             20                  25                  30 acc tct act tcc aaa gct tcc acc act acg act tct agc aaa acc acc   144
Thr Ser Thr Ser Lys Ala Ser Thr Thr Thr Thr Ser Ser Lys Thr Thr
         35                  40                  45 act aca tcc tct aag act acc acg act acc tcc aaa acc tct act acc   192
Thr Thr Ser Ser Lys Thr Thr Thr Thr Thr Ser Lys Thr Ser Thr Thr
 50                  55                  60 tct agc tcc tct acg ggc ggc gcc act cac aag acc tct act cag cgt   240
Ser Ser Ser Ser Thr Gly Gly Ala Thr His Lys Thr Ser Thr Gln Arg
 65                  70                  75                  80 ctg ctg gct gca taa tga                                           258
Leu Leu Ala Ala
```

```
<210> SEQ ID NO 193
<211> LENGTH: 84
<212> TYPE: PRT
<213> ORGANISM: artificial sequence
<220> FEATURE:
<223> OTHER INFORMATION: Synthetic Construct

<400> SEQUENCE: 193
```

```
Met Pro Val His Leu Pro Pro Pro Val His Leu Pro Pro Val His
 1               5                  10                  15

Gly Ser Ile Asp Pro Arg Phe His Glu Asn Trp Pro Ser Ala Gly Gly
             20                  25                  30

Thr Ser Thr Ser Lys Ala Ser Thr Thr Thr Thr Ser Ser Lys Thr Thr
         35                  40                  45

Thr Thr Ser Ser Lys Thr Thr Thr Thr Thr Ser Lys Thr Ser Thr Thr
 50                  55                  60

Ser Ser Ser Ser Thr Gly Gly Ala Thr His Lys Thr Ser Thr Gln Arg
 65                  70                  75                  80

Leu Leu Ala Ala
```

```
<210> SEQ ID NO 194
<211> LENGTH: 258
<212> TYPE: DNA
<213> ORGANISM: artificial sequence
<220> FEATURE:
<223> OTHER INFORMATION: chimeric gene encoding fusion peptide
<220> FEATURE:
<221> NAME/KEY: CDS
<222> LOCATION: (1)..(258)
```

-continued

<400> SEQUENCE: 194

| atg ctg ccg ccg ccg gtg cac gtg ccg ccg ccg gtg cac ctg ccg ccg | 48 |
| Met Leu Pro Pro Pro Val His Val Pro Pro Pro Val His Leu Pro Pro | |
| 1               5                   10                  15      | |

| gga tcc atc gat cca cgt ttc cac gaa aac tgg ccg tct gcc ggc ggt | 96 |
| Gly Ser Ile Asp Pro Arg Phe His Glu Asn Trp Pro Ser Ala Gly Gly | |
|             20                  25                  30          | |

| acc tct act tcc aaa gct tcc acc act acg act tct agc aaa acc acc | 144 |
| Thr Ser Thr Ser Lys Ala Ser Thr Thr Thr Thr Ser Ser Lys Thr Thr | |
|         35                  40                  45              | |

| act aca tcc tct aag act acc acg act acc tcc aaa acc tct act acc | 192 |
| Thr Thr Ser Ser Lys Thr Thr Thr Thr Thr Ser Lys Thr Ser Thr Thr | |
|     50                  55                  60                  | |

| tct agc tcc tct acg ggc ggc gcc act cac aag acc tct act cag cgt | 240 |
| Ser Ser Ser Ser Thr Gly Gly Ala Thr His Lys Thr Ser Thr Gln Arg | |
| 65                  70                  75                  80   | |

| ctg ctg gct gca taa tga | 258 |
| Leu Leu Ala Ala         | |

<210> SEQ ID NO 195
<211> LENGTH: 84
<212> TYPE: PRT
<213> ORGANISM: artificial sequence
<220> FEATURE:
<223> OTHER INFORMATION: Synthetic Construct

<400> SEQUENCE: 195

Met Leu Pro Pro Pro Val His Val Pro Pro Pro Val His Leu Pro Pro
1               5                   10                  15

Gly Ser Ile Asp Pro Arg Phe His Glu Asn Trp Pro Ser Ala Gly Gly
            20                  25                  30

Thr Ser Thr Ser Lys Ala Ser Thr Thr Thr Thr Ser Ser Lys Thr Thr
        35                  40                  45

Thr Thr Ser Ser Lys Thr Thr Thr Thr Thr Ser Lys Thr Ser Thr Thr
    50                  55                  60

Ser Ser Ser Ser Thr Gly Gly Ala Thr His Lys Thr Ser Thr Gln Arg
65                  70                  75                  80

Leu Leu Ala Ala

<210> SEQ ID NO 196
<211> LENGTH: 258
<212> TYPE: DNA
<213> ORGANISM: artificial sequence
<220> FEATURE:
<223> OTHER INFORMATION: chimeric gene encoding fusion peptide
<220> FEATURE:
<221> NAME/KEY: CDS
<222> LOCATION: (1)..(258)

<400> SEQUENCE: 196

| atg ccg ccg tgc cac tac ccg acc cag ccg ccg cgt ccg cag ccg cac | 48 |
| Met Pro Pro Cys His Tyr Pro Thr Gln Pro Pro Arg Pro Gln Pro His | |
| 1               5                   10                  15      | |

| gga tcc atc gat cca cgt ttc cac gaa aac tgg ccg tct gcc ggc ggt | 96 |
| Gly Ser Ile Asp Pro Arg Phe His Glu Asn Trp Pro Ser Ala Gly Gly | |
|             20                  25                  30          | |

| acc tct act tcc aaa gct tcc acc act acg act tct agc aaa acc acc | 144 |
| Thr Ser Thr Ser Lys Ala Ser Thr Thr Thr Thr Ser Ser Lys Thr Thr | |
|         35                  40                  45              | |

| act aca tcc tct aag act acc acg act acc tcc aaa acc tct act acc | 192 |
| Thr Thr Ser Ser Lys Thr Thr Thr Thr Thr Ser Lys Thr Ser Thr Thr | |

```
                  50                  55                  60
tct agc tcc tct acg ggc ggc gcc act cac aag acc tct act cag cgt    240
Ser Ser Ser Ser Thr Gly Gly Ala Thr His Lys Thr Ser Thr Gln Arg
 65                  70                  75                  80 ctg ctg gct gca taa tga                                            258
Leu Leu Ala Ala <210> SEQ ID NO 197
<211> LENGTH: 84
<212> TYPE: PRT
<213> ORGANISM: artificial sequence
<220> FEATURE:
<223> OTHER INFORMATION: Synthetic Construct

<400> SEQUENCE: 197

Met Pro Pro Cys His Tyr Pro Thr Gln Pro Pro Arg Pro Gln Pro His
 1               5                  10                  15

Gly Ser Ile Asp Pro Arg Phe His Glu Asn Trp Pro Ser Ala Gly Gly
                20                  25                  30

Thr Ser Thr Ser Lys Ala Ser Thr Thr Thr Ser Ser Lys Thr Thr
            35                  40                  45

Thr Thr Ser Ser Lys Thr Thr Thr Thr Ser Lys Thr Ser Thr Thr
        50                  55                  60

Ser Ser Ser Ser Thr Gly Gly Ala Thr His Lys Thr Ser Thr Gln Arg
 65                  70                  75                  80

Leu Leu Ala Ala

<210> SEQ ID NO 198
<211> LENGTH: 258
<212> TYPE: DNA
<213> ORGANISM: artificial sequence
<220> FEATURE:
<223> OTHER INFORMATION: chimeric gene encoding fusion peptide
<220> FEATURE:
<221> NAME/KEY: CDS
<222> LOCATION: (1)..(258)

<400> SEQUENCE: 198 atg ccg cag ccg cac ccg tgc ccg tgc cag cag ccg cac ccg agc ccg    48
Met Pro Gln Pro His Pro Cys Pro Cys Gln Gln Pro His Pro Ser Pro
 1               5                  10                  15 gga tcc atc gat cca cgt ttc cac gaa aac tgg ccg tct gcc ggc ggt    96
Gly Ser Ile Asp Pro Arg Phe His Glu Asn Trp Pro Ser Ala Gly Gly
                20                  25                  30 acc tct act tcc aaa gct tcc acc act acg act tct agc aaa acc acc    144
Thr Ser Thr Ser Lys Ala Ser Thr Thr Thr Ser Ser Lys Thr Thr
            35                  40                  45 act aca tcc tct aag act acc acg act acc tcc aaa acc tct act acc    192
Thr Thr Ser Ser Lys Thr Thr Thr Thr Ser Lys Thr Ser Thr Thr
        50                  55                  60 tct agc tcc tct acg ggc ggc gcc act cac aag acc tct act cag cgt    240
Ser Ser Ser Ser Thr Gly Gly Ala Thr His Lys Thr Ser Thr Gln Arg
 65                  70                  75                  80 ctg ctg gct gca taa tga                                            258
Leu Leu Ala Ala <210> SEQ ID NO 199
<211> LENGTH: 84
<212> TYPE: PRT
<213> ORGANISM: artificial sequence
<220> FEATURE:
<223> OTHER INFORMATION: Synthetic Construct
```

<400> SEQUENCE: 199

Met Pro Gln Pro His Pro Cys Pro Cys Gln Gln His Pro Ser Pro
1               5                   10                  15

Gly Ser Ile Asp Pro Arg Phe His Glu Asn Trp Pro Ser Ala Gly Gly
            20                  25                  30

Thr Ser Thr Ser Lys Ala Ser Thr Thr Thr Ser Ser Lys Thr Thr
            35                  40                  45

Thr Thr Ser Ser Lys Thr Thr Thr Thr Ser Lys Thr Ser Thr Thr
        50                  55                  60

Ser Ser Ser Ser Thr Gly Gly Ala Thr His Lys Thr Ser Thr Gln Arg
65              70                  75                  80

Leu Leu Ala Ala

<210> SEQ ID NO 200
<211> LENGTH: 258
<212> TYPE: DNA
<213> ORGANISM: artificial sequence
<220> FEATURE:
<223> OTHER INFORMATION: chimeric gene encoding fusion peptide
<220> FEATURE:
<221> NAME/KEY: CDS
<222> LOCATION: (1)..(258)

<400> SEQUENCE: 200 atg tgc cag ctg cag ggg acc tgc ggt gtg ggt agc acc ccg atc ctg     48
Met Cys Gln Leu Gln Gly Thr Cys Gly Val Gly Ser Thr Pro Ile Leu
1               5                   10                  15 gga tcc atc gat cca cgt ttc cac gaa aac tgg ccg tct gcc ggc ggt     96
Gly Ser Ile Asp Pro Arg Phe His Glu Asn Trp Pro Ser Ala Gly Gly
            20                  25                  30 acc tct act tcc aaa gct tcc acc act acg act tct agc aaa acc acc    144
Thr Ser Thr Ser Lys Ala Ser Thr Thr Thr Ser Ser Lys Thr Thr
            35                  40                  45 act aca tcc tct aag act acc acg act acc tcc aaa acc tct act acc    192
Thr Thr Ser Ser Lys Thr Thr Thr Thr Ser Lys Thr Ser Thr Thr
        50                  55                  60 tct agc tcc tct acg ggc ggc gcc act cac aag acc tct act cag cgt    240
Ser Ser Ser Ser Thr Gly Gly Ala Thr His Lys Thr Ser Thr Gln Arg
65              70                  75                  80 ctg ctg gct gca taa tga                                            258
Leu Leu Ala Ala <210> SEQ ID NO 201
<211> LENGTH: 84
<212> TYPE: PRT
<213> ORGANISM: artificial sequence
<220> FEATURE:
<223> OTHER INFORMATION: Synthetic Construct

<400> SEQUENCE: 201

Met Cys Gln Leu Gln Gly Thr Cys Gly Val Gly Ser Thr Pro Ile Leu
1               5                   10                  15

Gly Ser Ile Asp Pro Arg Phe His Glu Asn Trp Pro Ser Ala Gly Gly
            20                  25                  30

Thr Ser Thr Ser Lys Ala Ser Thr Thr Thr Ser Ser Lys Thr Thr
            35                  40                  45

Thr Thr Ser Ser Lys Thr Thr Thr Thr Ser Lys Thr Ser Thr Thr
        50                  55                  60

Ser Ser Ser Ser Thr Gly Gly Ala Thr His Lys Thr Ser Thr Gln Arg

<210> SEQ ID NO 202
<211> LENGTH: 258
<212> TYPE: DNA
<213> ORGANISM: artificial sequence
<220> FEATURE:
<223> OTHER INFORMATION: chimeric gene encoding fusion peptide
<220> FEATURE:
<221> NAME/KEY: CDS
<222> LOCATION: (1)..(258)

<400> SEQUENCE: 202

```
atg ggt cag tgc gtg gaa ttc ctg cgt cac cag tgc agc ccg acc gcg    48
Met Gly Gln Cys Val Glu Phe Leu Arg His Gln Cys Ser Pro Thr Ala
1               5                   10                  15 gga tcc atc gat cca cgt ttc cac gaa aac tgg ccg tct gcc ggc ggt    96
Gly Ser Ile Asp Pro Arg Phe His Glu Asn Trp Pro Ser Ala Gly Gly
            20                  25                  30 acc tct act tcc aaa gct tcc acc act acg act tct agc aaa acc acc   144
Thr Ser Thr Ser Lys Ala Ser Thr Thr Thr Thr Ser Ser Lys Thr Thr
        35                  40                  45 act aca tcc tct aag act acc acg act acc tcc aaa acc tct act acc   192
Thr Thr Ser Ser Lys Thr Thr Thr Thr Thr Ser Lys Thr Ser Thr Thr
    50                  55                  60 tct agc tcc tct acg ggc ggc gcc act cac aag acc tct act cag cgt   240
Ser Ser Ser Ser Thr Gly Gly Ala Thr His Lys Thr Ser Thr Gln Arg
65                  70                  75                  80 ctg ctg gct gca taa tga                                           258
Leu Leu Ala Ala
```

<210> SEQ ID NO 203
<211> LENGTH: 84
<212> TYPE: PRT
<213> ORGANISM: artificial sequence
<220> FEATURE:
<223> OTHER INFORMATION: Synthetic Construct

<400> SEQUENCE: 203

```
Met Gly Gln Cys Val Glu Phe Leu Arg His Gln Cys Ser Pro Thr Ala
1               5                   10                  15

Gly Ser Ile Asp Pro Arg Phe His Glu Asn Trp Pro Ser Ala Gly Gly
            20                  25                  30

Thr Ser Thr Ser Lys Ala Ser Thr Thr Thr Ser Ser Lys Thr Thr
        35                  40                  45

Thr Thr Ser Ser Lys Thr Thr Thr Thr Thr Ser Lys Thr Ser Thr Thr
    50                  55                  60

Ser Ser Ser Ser Thr Gly Gly Ala Thr His Lys Thr Ser Thr Gln Arg
65                  70                  75                  80

Leu Leu Ala Ala
```

<210> SEQ ID NO 204
<211> LENGTH: 258
<212> TYPE: DNA
<213> ORGANISM: artificial sequence
<220> FEATURE:
<223> OTHER INFORMATION: chimeric gene encoding fusion peptide
<220> FEATURE:
<221> NAME/KEY: CDS
<222> LOCATION: (1)..(258)

<400> SEQUENCE: 204

```
atg acc ccg tac tgc agc ccg cag tgc cag agc ctg cgt cag cag tgc    48
Met Thr Pro Tyr Cys Ser Pro Gln Cys Gln Ser Leu Arg Gln Gln Cys
1               5                   10                  15 gga tcc atc gat cca cgt ttc cac gaa aac tgg ccg tct gcc ggc ggt    96
Gly Ser Ile Asp Pro Arg Phe His Glu Asn Trp Pro Ser Ala Gly Gly
                20                  25                  30 acc tct act tcc aaa gct tcc acc act acg act tct agc aaa acc acc   144
Thr Ser Thr Ser Lys Ala Ser Thr Thr Thr Thr Ser Ser Lys Thr Thr
            35                  40                  45 act aca tcc tct aag act acc acg act acc tcc aaa acc tct act acc   192
Thr Thr Ser Ser Lys Thr Thr Thr Thr Thr Ser Lys Thr Ser Thr Thr
        50                  55                  60 tct agc tcc tct acg ggc ggc gcc act cac aag acc tct act cag cgt   240
Ser Ser Ser Ser Thr Gly Gly Ala Thr His Lys Thr Ser Thr Gln Arg
65                  70                  75                  80 ctg ctg gct gca taa tga                                           258
Leu Leu Ala Ala <210> SEQ ID NO 205
<211> LENGTH: 84
<212> TYPE: PRT
<213> ORGANISM: artificial sequence
<220> FEATURE:
<223> OTHER INFORMATION: Synthetic Construct

<400> SEQUENCE: 205

Met Thr Pro Tyr Cys Ser Pro Gln Cys Gln Ser Leu Arg Gln Gln Cys
1               5                   10                  15

Gly Ser Ile Asp Pro Arg Phe His Glu Asn Trp Pro Ser Ala Gly Gly
                20                  25                  30

Thr Ser Thr Ser Lys Ala Ser Thr Thr Thr Thr Ser Ser Lys Thr Thr
            35                  40                  45

Thr Thr Ser Ser Lys Thr Thr Thr Thr Thr Ser Lys Thr Ser Thr Thr
        50                  55                  60

Ser Ser Ser Ser Thr Gly Gly Ala Thr His Lys Thr Ser Thr Gln Arg
65                  70                  75                  80

Leu Leu Ala Ala

<210> SEQ ID NO 206
<211> LENGTH: 258
<212> TYPE: DNA
<213> ORGANISM: artificial sequence
<220> FEATURE:
<223> OTHER INFORMATION: chimeric gene encoding fusion peptide
<220> FEATURE:
<221> NAME/KEY: CDS
<222> LOCATION: (1)..(258)

<400> SEQUENCE: 206 atg tgc cag cag ctg cgt cag gtg gaa ccg cag cac cgt tac cag gcg    48
Met Cys Gln Gln Leu Arg Gln Val Glu Pro Gln His Arg Tyr Gln Ala
1               5                   10                  15 gga tcc atc gat cca cgt ttc cac gaa aac tgg ccg tct gcc ggc ggt    96
Gly Ser Ile Asp Pro Arg Phe His Glu Asn Trp Pro Ser Ala Gly Gly
                20                  25                  30 acc tct act tcc aaa gct tcc acc act acg act tct agc aaa acc acc   144
Thr Ser Thr Ser Lys Ala Ser Thr Thr Thr Thr Ser Ser Lys Thr Thr
            35                  40                  45 act aca tcc tct aag act acc acg act acc tcc aaa acc tct act acc   192
Thr Thr Ser Ser Lys Thr Thr Thr Thr Thr Ser Lys Thr Ser Thr Thr
        50                  55                  60
```

```
tct agc tcc tct acg ggc ggc gcc act cac aag acc tct act cag cgt      240
Ser Ser Ser Ser Thr Gly Gly Ala Thr His Lys Thr Ser Thr Gln Arg
 65                  70                  75                  80 ctg ctg gct gca taa tga                                              258
Leu Leu Ala Ala <210> SEQ ID NO 207
<211> LENGTH: 84
<212> TYPE: PRT
<213> ORGANISM: artificial sequence
<220> FEATURE:
<223> OTHER INFORMATION: Synthetic Construct

<400> SEQUENCE: 207

Met Cys Gln Gln Leu Arg Gln Val Glu Pro Gln His Arg Tyr Gln Ala
 1               5                  10                  15

Gly Ser Ile Asp Pro Arg Phe His Glu Asn Trp Pro Ser Ala Gly Gly
             20                  25                  30

Thr Ser Thr Ser Lys Ala Ser Thr Thr Thr Ser Ser Lys Thr Thr
         35                  40                  45

Thr Thr Ser Ser Lys Thr Thr Thr Thr Ser Lys Thr Ser Thr Thr
     50                  55                  60

Ser Ser Ser Ser Thr Gly Gly Ala Thr His Lys Thr Ser Thr Gln Arg
 65                  70                  75                  80

Leu Leu Ala Ala

<210> SEQ ID NO 208
<211> LENGTH: 258
<212> TYPE: DNA
<213> ORGANISM: artificial sequence
<220> FEATURE:
<223> OTHER INFORMATION: chimeric gene encoding fusion peptide
<220> FEATURE:
<221> NAME/KEY: CDS
<222> LOCATION: (1)..(258)

<400> SEQUENCE: 208 atg atc ttc ggt ctg gtg ctg cag agc atc ctg cag cag cag ccg cag     48
Met Ile Phe Gly Leu Val Leu Gln Ser Ile Leu Gln Gln Gln Pro Gln
 1               5                  10                  15 gga tcc atc gat cca cgt ttc cac gaa aac tgg ccg tct gcc ggc ggt     96
Gly Ser Ile Asp Pro Arg Phe His Glu Asn Trp Pro Ser Ala Gly Gly
             20                  25                  30 acc tct act tcc aaa gct tcc acc act acg act tct agc aaa acc acc    144
Thr Ser Thr Ser Lys Ala Ser Thr Thr Thr Thr Ser Ser Lys Thr Thr
         35                  40                  45 act aca tcc tct aag act acc acg act acc tcc aaa acc tct act acc    192
Thr Thr Ser Ser Lys Thr Thr Thr Thr Ser Lys Thr Ser Thr Thr
     50                  55                  60 tct agc tcc tct acg ggc ggc gcc act cac aag acc tct act cag cgt    240
Ser Ser Ser Ser Thr Gly Gly Ala Thr His Lys Thr Ser Thr Gln Arg
 65                  70                  75                  80 ctg ctg gct gca taa tga                                            258
Leu Leu Ala Ala <210> SEQ ID NO 209
<211> LENGTH: 84
<212> TYPE: PRT
<213> ORGANISM: artificial sequence
<220> FEATURE:
<223> OTHER INFORMATION: Synthetic Construct
```

<400> SEQUENCE: 209

Met Ile Phe Gly Leu Val Leu Gln Ser Ile Leu Gln Gln Pro Gln
1               5                   10                  15

Gly Ser Ile Asp Pro Arg Phe His Glu Asn Trp Pro Ser Ala Gly Gly
            20                  25                  30

Thr Ser Thr Ser Lys Ala Ser Thr Thr Thr Ser Ser Lys Thr Thr
        35                  40                  45

Thr Thr Ser Ser Lys Thr Thr Thr Thr Ser Lys Thr Ser Thr Thr
50                  55                  60

Ser Ser Ser Ser Thr Gly Gly Ala Thr His Lys Thr Ser Thr Gln Arg
65                  70                  75                  80

Leu Leu Ala Ala

<210> SEQ ID NO 210
<211> LENGTH: 258
<212> TYPE: DNA
<213> ORGANISM: artificial sequence
<220> FEATURE:
<223> OTHER INFORMATION: chimeric gene encoding fusion peptide
<220> FEATURE:
<221> NAME/KEY: CDS
<222> LOCATION: (1)..(258)

<400> SEQUENCE: 210 atg agc ggt cag gtg gcg ggt ctg ctg gcg gcg cag atc gcg cag cag     48
Met Ser Gly Gln Val Ala Gly Leu Leu Ala Ala Gln Ile Ala Gln Gln
1               5                   10                  15 gga tcc atc gat cca cgt ttc cac gaa aac tgg ccg tct gcc ggc ggt     96
Gly Ser Ile Asp Pro Arg Phe His Glu Asn Trp Pro Ser Ala Gly Gly
            20                  25                  30 acc tct act tcc aaa gct tcc acc act acg act tct agc aaa acc acc    144
Thr Ser Thr Ser Lys Ala Ser Thr Thr Thr Thr Ser Ser Lys Thr Thr
        35                  40                  45 act aca tcc tct aag act acc acg act acc tcc aaa acc tct act acc    192
Thr Thr Ser Ser Lys Thr Thr Thr Thr Ser Lys Thr Ser Thr Thr
50                  55                  60 tct agc tcc tct acg ggc ggc gcc act cac aag acc tct act cag cgt    240
Ser Ser Ser Ser Thr Gly Gly Ala Thr His Lys Thr Ser Thr Gln Arg
65                  70                  75                  80 ctg ctg gct gca taa tga                                             258
Leu Leu Ala Ala <210> SEQ ID NO 211
<211> LENGTH: 84
<212> TYPE: PRT
<213> ORGANISM: artificial sequence
<220> FEATURE:
<223> OTHER INFORMATION: Synthetic Construct

<400> SEQUENCE: 211

Met Ser Gly Gln Val Ala Gly Leu Leu Ala Ala Gln Ile Ala Gln Gln
1               5                   10                  15

Gly Ser Ile Asp Pro Arg Phe His Glu Asn Trp Pro Ser Ala Gly Gly
            20                  25                  30

Thr Ser Thr Ser Lys Ala Ser Thr Thr Thr Ser Ser Lys Thr Thr
        35                  40                  45

Thr Thr Ser Ser Lys Thr Thr Thr Thr Ser Lys Thr Ser Thr Thr
50                  55                  60

Ser Ser Ser Ser Thr Gly Gly Ala Thr His Lys Thr Ser Thr Gln Arg
65                  70                  75                  80

Leu Leu Ala Ala

<210> SEQ ID NO 212
<211> LENGTH: 258
<212> TYPE: DNA
<213> ORGANISM: artificial sequence
<220> FEATURE:
<223> OTHER INFORMATION: chimeric gene encoding fusion peptide
<220> FEATURE:
<221> NAME/KEY: CDS
<222> LOCATION: (1)..(258)

<400> SEQUENCE: 212

```
atg ctg acc gcg atg tgc ggt ctg cag cag ccg acc ccg tgc ccg tac      48
Met Leu Thr Ala Met Cys Gly Leu Gln Gln Pro Thr Pro Cys Pro Tyr
1               5                   10                  15 gga tcc atc gat cca cgt ttc cac gaa aac tgg ccg tct gcc ggc ggt      96
Gly Ser Ile Asp Pro Arg Phe His Glu Asn Trp Pro Ser Ala Gly Gly
            20                  25                  30 acc tct act tcc aaa gct tcc acc act acg act tct agc aaa acc acc     144
Thr Ser Thr Ser Lys Ala Ser Thr Thr Thr Thr Ser Ser Lys Thr Thr
        35                  40                  45 act aca tcc tct aag act acc acg act acc tcc aaa acc tct act acc     192
Thr Thr Ser Ser Lys Thr Thr Thr Thr Thr Ser Lys Thr Ser Thr Thr
    50                  55                  60 tct agc tcc tct acg ggc ggc gcc act cac aag acc tct act cag cgt     240
Ser Ser Ser Ser Thr Gly Gly Ala Thr His Lys Thr Ser Thr Gln Arg
65                  70                  75                  80 ctg ctg gct gca taa tga                                             258
Leu Leu Ala Ala
```

<210> SEQ ID NO 213
<211> LENGTH: 84
<212> TYPE: PRT
<213> ORGANISM: artificial sequence
<220> FEATURE:
<223> OTHER INFORMATION: Synthetic Construct

<400> SEQUENCE: 213

Met Leu Thr Ala Met Cys Gly Leu Gln Gln Pro Thr Pro Cys Pro Tyr
1               5                   10                  15

Gly Ser Ile Asp Pro Arg Phe His Glu Asn Trp Pro Ser Ala Gly Gly
            20                  25                  30

Thr Ser Thr Ser Lys Ala Ser Thr Thr Thr Thr Ser Ser Lys Thr Thr
        35                  40                  45

Thr Thr Ser Ser Lys Thr Thr Thr Thr Thr Ser Lys Thr Ser Thr Thr
    50                  55                  60

Ser Ser Ser Ser Thr Gly Gly Ala Thr His Lys Thr Ser Thr Gln Arg
65                  70                  75                  80

Leu Leu Ala Ala

<210> SEQ ID NO 214
<211> LENGTH: 258
<212> TYPE: DNA
<213> ORGANISM: artificial sequence
<220> FEATURE:
<223> OTHER INFORMATION: chimeric gene encoding fusion peptide
<220> FEATURE:
<221> NAME/KEY: CDS
<222> LOCATION: (1)..(258)

<400> SEQUENCE: 214

```
atg gcg ctg gcg gcg agc gcg acc agc acc cac acc agc ggt ggt       48
Met Leu Ala Leu Ala Ala Ser Ala Thr Ser Thr His Thr Ser Gly Gly
1               5                   10                  15 gga tcc atc gat cca cgt ttc cac gaa aac tgg ccg tct gcc ggc ggt    96
Gly Ser Ile Asp Pro Arg Phe His Glu Asn Trp Pro Ser Ala Gly Gly
            20                  25                  30 acc tct act tcc aaa gct tcc acc act acg act tct agc aaa acc acc   144
Thr Ser Thr Ser Lys Ala Ser Thr Thr Thr Thr Ser Ser Lys Thr Thr
        35                  40                  45 act aca tcc tct aag act acc acg act acc tcc aaa acc tct act acc   192
Thr Thr Ser Ser Lys Thr Thr Thr Thr Thr Ser Lys Thr Ser Thr Thr
50                  55                  60 tct agc tcc tct acg ggc ggc gcc act cac aag acc tct act cag cgt   240
Ser Ser Ser Ser Thr Gly Gly Ala Thr His Lys Thr Ser Thr Gln Arg
65                  70                  75                  80 ctg ctg gct gca taa tga                                            258
Leu Leu Ala Ala
```

<210> SEQ ID NO 215
<211> LENGTH: 84
<212> TYPE: PRT
<213> ORGANISM: artificial sequence
<220> FEATURE:
<223> OTHER INFORMATION: Synthetic Construct

<400> SEQUENCE: 215

```
Met Leu Ala Leu Ala Ala Ser Ala Thr Ser Thr His Thr Ser Gly Gly
1               5                   10                  15

Gly Ser Ile Asp Pro Arg Phe His Glu Asn Trp Pro Ser Ala Gly Gly
            20                  25                  30

Thr Ser Thr Ser Lys Ala Ser Thr Thr Thr Thr Ser Ser Lys Thr Thr
        35                  40                  45

Thr Thr Ser Ser Lys Thr Thr Thr Thr Thr Ser Lys Thr Ser Thr Thr
    50                  55                  60

Ser Ser Ser Ser Thr Gly Gly Ala Thr His Lys Thr Ser Thr Gln Arg
65                  70                  75                  80

Leu Leu Ala Ala
```

<210> SEQ ID NO 216
<211> LENGTH: 258
<212> TYPE: DNA
<213> ORGANISM: artificial sequence
<220> FEATURE:
<223> OTHER INFORMATION: chimeric gene encoding fusion peptide
<220> FEATURE:
<221> NAME/KEY: CDS
<222> LOCATION: (1)..(258)

<400> SEQUENCE: 216

```
atg tgc ggt tgc cag ccg ccg ccg ccg gtg cac ctg ccg ccg ccg gtg    48
Met Cys Gly Cys Gln Pro Pro Pro Pro Val His Leu Pro Pro Pro Val
1               5                   10                  15 gga tcc atc gat cca cgt ttc cac gaa aac tgg ccg tct gcc ggc ggt    96
Gly Ser Ile Asp Pro Arg Phe His Glu Asn Trp Pro Ser Ala Gly Gly
            20                  25                  30 acc tct act tcc aaa gct tcc acc act acg act tct agc aaa acc acc   144
Thr Ser Thr Ser Lys Ala Ser Thr Thr Thr Thr Ser Ser Lys Thr Thr
        35                  40                  45 act aca tcc tct aag act acc acg act acc tcc aaa acc tct act acc   192
Thr Thr Ser Ser Lys Thr Thr Thr Thr Thr Ser Lys Thr Ser Thr Thr
    50                  55                  60
```

```
tct agc tcc tct acg ggc ggc gcc act cac aag acc tct act cag cgt      240
Ser Ser Ser Ser Thr Gly Gly Ala Thr His Lys Thr Ser Thr Gln Arg
 65                  70                  75                  80 ctg ctg gct gca taa tga                                              258
Leu Leu Ala Ala <210> SEQ ID NO 217
<211> LENGTH: 84
<212> TYPE: PRT
<213> ORGANISM: artificial sequence
<220> FEATURE:
<223> OTHER INFORMATION: Synthetic Construct

<400> SEQUENCE: 217

Met Cys Gly Cys Gln Pro Pro Pro Val His Leu Pro Pro Pro Val
 1               5                  10                  15

Gly Ser Ile Asp Pro Arg Phe His Glu Asn Trp Pro Ser Ala Gly Gly
                 20                  25                  30

Thr Ser Thr Ser Lys Ala Ser Thr Thr Thr Ser Ser Lys Thr Thr
                 35                  40                  45

Thr Thr Ser Ser Lys Thr Thr Thr Thr Ser Lys Thr Ser Thr Thr
         50                  55                  60

Ser Ser Ser Ser Thr Gly Gly Ala Thr His Lys Thr Ser Thr Gln Arg
 65                  70                  75                  80

Leu Leu Ala Ala

<210> SEQ ID NO 218
<211> LENGTH: 258
<212> TYPE: DNA
<213> ORGANISM: artificial sequence
<220> FEATURE:
<223> OTHER INFORMATION: chimeric gene encoding fusion peptide
<220> FEATURE:
<221> NAME/KEY: CDS
<222> LOCATION: (1)..(258)

<400> SEQUENCE: 218 atg cac ctg ccg ccg ccg gtg cac ctg ccg ccg ccg gtg cac ctg ccg       48
Met His Leu Pro Pro Pro Val His Leu Pro Pro Pro Val His Leu Pro
 1               5                  10                  15 gga tcc atc gat cca cgt ttc cac gaa aac tgg ccg tct gcc ggc ggt       96
Gly Ser Ile Asp Pro Arg Phe His Glu Asn Trp Pro Ser Ala Gly Gly
                 20                  25                  30 acc tct act tcc aaa gct tcc acc act acg act tct agc aaa acc acc      144
Thr Ser Thr Ser Lys Ala Ser Thr Thr Thr Ser Ser Lys Thr Thr
                 35                  40                  45 act aca tcc tct aag act acc acg act acc tcc aaa acc tct act acc      192
Thr Thr Ser Ser Lys Thr Thr Thr Thr Ser Lys Thr Ser Thr Thr
         50                  55                  60 tct agc tcc tct acg ggc ggc gcc act cac aag acc tct act cag cgt      240
Ser Ser Ser Ser Thr Gly Gly Ala Thr His Lys Thr Ser Thr Gln Arg
 65                  70                  75                  80 ctg ctg gct gca taa tga                                              258
Leu Leu Ala Ala <210> SEQ ID NO 219
<211> LENGTH: 84
<212> TYPE: PRT
<213> ORGANISM: artificial sequence
<220> FEATURE:
<223> OTHER INFORMATION: Synthetic Construct

<400> SEQUENCE: 219
```

```
Met His Leu Pro Pro Val His Leu Pro Pro Val His Leu Pro
1               5                  10                  15

Gly Ser Ile Asp Pro Arg Phe His Glu Asn Trp Pro Ser Ala Gly Gly
                20                  25                  30

Thr Ser Thr Ser Lys Ala Ser Thr Thr Thr Ser Ser Lys Thr Thr
            35                  40                  45

Thr Thr Ser Ser Lys Thr Thr Thr Thr Ser Lys Thr Ser Thr Thr
        50                  55                  60

Ser Ser Ser Ser Thr Gly Gly Ala Thr His Lys Thr Ser Thr Gln Arg
65                  70                  75                  80

Leu Leu Ala Ala
```

<210> SEQ ID NO 220
<211> LENGTH: 258
<212> TYPE: DNA
<213> ORGANISM: artificial sequence
<220> FEATURE:
<223> OTHER INFORMATION: chimeric gene encoding fusion peptide
<220> FEATURE:
<221> NAME/KEY: CDS
<222> LOCATION: (1)..(258)

<400> SEQUENCE: 220

```
atg ccg ccg gtg cac ctg ccg ccg gtg cac ctg ccg ccg gtg           48
Met Pro Pro Val His Leu Pro Pro Val His Leu Pro Pro Val
1               5                  10                  15 gga tcc atc gat cca cgt ttc cac gaa aac tgg ccg tct gcc ggc ggt   96
Gly Ser Ile Asp Pro Arg Phe His Glu Asn Trp Pro Ser Ala Gly Gly
                20                  25                  30 acc tct act tcc aaa gct tcc acc act acg act tct agc aaa acc acc   144
Thr Ser Thr Ser Lys Ala Ser Thr Thr Thr Thr Ser Ser Lys Thr Thr
            35                  40                  45 act aca tcc tct aag act acc acg act acc tcc aaa acc tct act acc   192
Thr Thr Ser Ser Lys Thr Thr Thr Thr Ser Lys Thr Ser Thr Thr
        50                  55                  60 tct agc tcc tct acg ggc ggc gcc act cac aag acc tct act cag cgt   240
Ser Ser Ser Ser Thr Gly Gly Ala Thr His Lys Thr Ser Thr Gln Arg
65                  70                  75                  80 ctg ctg gct gca taa tga                                           258
Leu Leu Ala Ala
```

<210> SEQ ID NO 221
<211> LENGTH: 84
<212> TYPE: PRT
<213> ORGANISM: artificial sequence
<220> FEATURE:
<223> OTHER INFORMATION: Synthetic Construct

<400> SEQUENCE: 221

```
Met Pro Pro Val His Leu Pro Pro Val His Leu Pro Pro Val
1               5                  10                  15

Gly Ser Ile Asp Pro Arg Phe His Glu Asn Trp Pro Ser Ala Gly Gly
                20                  25                  30

Thr Ser Thr Ser Lys Ala Ser Thr Thr Thr Thr Ser Ser Lys Thr Thr
            35                  40                  45

Thr Thr Ser Ser Lys Thr Thr Thr Thr Ser Lys Thr Ser Thr Thr
        50                  55                  60

Ser Ser Ser Ser Thr Gly Gly Ala Thr His Lys Thr Ser Thr Gln Arg
65                  70                  75                  80
```

```
<210> SEQ ID NO 222
<211> LENGTH: 258
<212> TYPE: DNA
<213> ORGANISM: artificial sequence
<220> FEATURE:
<223> OTHER INFORMATION: chimeric gene encoding fusion peptide
<220> FEATURE:
<221> NAME/KEY: CDS
<222> LOCATION: (1)..(258)

<400> SEQUENCE: 222 atg cac gtg ccg ccg gtg cac ctg ccg ccg ccg tgc cac tac         48
Met His Val Pro Pro Val His Leu Pro Pro Pro Cys His Tyr
1               5                   10                  15 gga tcc atc gat cca cgt ttc cac gaa aac tgg ccg tct gcc ggc ggt    96
Gly Ser Ile Asp Pro Arg Phe His Glu Asn Trp Pro Ser Ala Gly Gly
            20                  25                  30 acc tct act tcc aaa gct tcc act act acg act tct agc aaa acc acc   144
Thr Ser Thr Ser Lys Ala Ser Thr Thr Thr Thr Ser Ser Lys Thr Thr
        35                  40                  45 act aca tcc tct aag act acc acg act acc tcc aaa acc tct act acc   192
Thr Thr Ser Ser Lys Thr Thr Thr Thr Thr Ser Lys Thr Ser Thr Thr
    50                  55                  60 tct agc tcc tct acg ggc ggc gcc act cac aag acc tct act cag cgt   240
Ser Ser Ser Ser Thr Gly Gly Ala Thr His Lys Thr Ser Thr Gln Arg
65                  70                  75                  80 ctg ctg gct gca taa tga                                           258
Leu Leu Ala Ala <210> SEQ ID NO 223
<211> LENGTH: 84
<212> TYPE: PRT
<213> ORGANISM: artificial sequence
<220> FEATURE:
<223> OTHER INFORMATION: Synthetic Construct

<400> SEQUENCE: 223

Met His Val Pro Pro Val His Leu Pro Pro Pro Cys His Tyr
1               5                   10                  15

Gly Ser Ile Asp Pro Arg Phe His Glu Asn Trp Pro Ser Ala Gly Gly
            20                  25                  30

Thr Ser Thr Ser Lys Ala Ser Thr Thr Thr Thr Ser Ser Lys Thr Thr
        35                  40                  45

Thr Thr Ser Ser Lys Thr Thr Thr Thr Thr Ser Lys Thr Ser Thr Thr
    50                  55                  60

Ser Ser Ser Ser Thr Gly Gly Ala Thr His Lys Thr Ser Thr Gln Arg
65                  70                  75                  80

Leu Leu Ala Ala

<210> SEQ ID NO 224
<211> LENGTH: 258
<212> TYPE: DNA
<213> ORGANISM: artificial sequence
<220> FEATURE:
<223> OTHER INFORMATION: chimeric gene encoding fusion peptide
<220> FEATURE:
<221> NAME/KEY: CDS
<222> LOCATION: (1)..(258)

<400> SEQUENCE: 224 atg ccg acc cag ccg ccg cgt ccg cag ccg cac ccg cag ccg cac ccg    48
```

```
Met Pro Thr Gln Pro Pro Arg Pro Gln Pro His Pro Gln Pro His Pro
1               5                   10                  15 gga tcc atc gat cca cgt ttc cac gaa aac tgg ccg tct gcc ggc ggt      96
Gly Ser Ile Asp Pro Arg Phe His Glu Asn Trp Pro Ser Ala Gly Gly
            20                  25                  30 acc tct act tcc aaa gct tcc acc act acg act tct agc aaa acc acc     144
Thr Ser Thr Ser Lys Ala Ser Thr Thr Thr Thr Ser Ser Lys Thr Thr
                35                  40                  45 act aca tcc tct aag act acc acg act acc tcc aaa acc tct act acc     192
Thr Thr Ser Ser Lys Thr Thr Thr Thr Thr Ser Lys Thr Ser Thr Thr
50                  55                  60 tct agc tcc tct acg ggc ggc gcc act cac aag acc tct act cag cgt     240
Ser Ser Ser Ser Thr Gly Gly Ala Thr His Lys Thr Ser Thr Gln Arg
65                  70                  75                  80 ctg ctg gct gca taa tga                                              258
Leu Leu Ala Ala
```

<210> SEQ ID NO 225
<211> LENGTH: 84
<212> TYPE: PRT
<213> ORGANISM: artificial sequence
<220> FEATURE:
<223> OTHER INFORMATION: Synthetic Construct

<400> SEQUENCE: 225

```
Met Pro Thr Gln Pro Pro Arg Pro Gln Pro His Pro Gln Pro His Pro
1               5                   10                  15

Gly Ser Ile Asp Pro Arg Phe His Glu Asn Trp Pro Ser Ala Gly Gly
            20                  25                  30

Thr Ser Thr Ser Lys Ala Ser Thr Thr Thr Thr Ser Ser Lys Thr Thr
                35                  40                  45

Thr Thr Ser Ser Lys Thr Thr Thr Thr Thr Ser Lys Thr Ser Thr Thr
50                  55                  60

Ser Ser Ser Ser Thr Gly Gly Ala Thr His Lys Thr Ser Thr Gln Arg
65                  70                  75                  80

Leu Leu Ala Ala
```

<210> SEQ ID NO 226
<211> LENGTH: 258
<212> TYPE: DNA
<213> ORGANISM: artificial sequence
<220> FEATURE:
<223> OTHER INFORMATION: chimeric gene encoding fusion peptide
<220> FEATURE:
<221> NAME/KEY: CDS
<222> LOCATION: (1)..(258)

<400> SEQUENCE: 226

```
atg tgc ccg tgc cag cag ccg cac ccg agc ccg tgc cag ctg cag ggg      48
Met Cys Pro Cys Gln Gln Pro His Pro Ser Pro Cys Gln Leu Gln Gly
1               5                   10                  15 gga tcc atc gat cca cgt ttc cac gaa aac tgg ccg tct gcc ggc ggt      96
Gly Ser Ile Asp Pro Arg Phe His Glu Asn Trp Pro Ser Ala Gly Gly
            20                  25                  30 acc tct act tcc aaa gct tcc acc act acg act tct agc aaa acc acc     144
Thr Ser Thr Ser Lys Ala Ser Thr Thr Thr Thr Ser Ser Lys Thr Thr
                35                  40                  45 act aca tcc tct aag act acc acg act acc tcc aaa acc tct act acc     192
Thr Thr Ser Ser Lys Thr Thr Thr Thr Thr Ser Lys Thr Ser Thr Thr
50                  55                  60 tct agc tcc tct acg ggc ggc gcc act cac aag acc tct act cag cgt     240
Ser Ser Ser Ser Thr Gly Gly Ala Thr His Lys Thr Ser Thr Gln Arg
```

```
Ser Ser Ser Ser Thr Gly Gly Ala Thr His Lys Thr Ser Thr Gln Arg
 65                  70                  75                  80 ctg ctg gct gca taa tga                                              258
Leu Leu Ala Ala
```

<210> SEQ ID NO 227
<211> LENGTH: 84
<212> TYPE: PRT
<213> ORGANISM: artificial sequence
<220> FEATURE:
<223> OTHER INFORMATION: Synthetic Construct

<400> SEQUENCE: 227

```
Met Cys Pro Cys Gln Gln Pro His Pro Ser Pro Cys Gln Leu Gln Gly
 1               5                  10                  15

Gly Ser Ile Asp Pro Arg Phe His Glu Asn Trp Pro Ser Ala Gly Gly
             20                  25                  30

Thr Ser Thr Ser Lys Ala Ser Thr Thr Thr Ser Ser Lys Thr Thr
         35                  40                  45

Thr Thr Ser Ser Lys Thr Thr Thr Thr Ser Lys Thr Ser Thr Thr
 50                  55                  60

Ser Ser Ser Ser Thr Gly Gly Ala Thr His Lys Thr Ser Thr Gln Arg
 65                  70                  75                  80

Leu Leu Ala Ala
```

<210> SEQ ID NO 228
<211> LENGTH: 258
<212> TYPE: DNA
<213> ORGANISM: artificial sequence
<220> FEATURE:
<223> OTHER INFORMATION: chimeric gene encoding fusion peptide
<220> FEATURE:
<221> NAME/KEY: CDS
<222> LOCATION: (1)..(258)

<400> SEQUENCE: 228

```
atg acc tgc ggt gtg ggt agc acc ccg atc ctg ggt cag tgc gtg gaa    48
Met Thr Cys Gly Val Gly Ser Thr Pro Ile Leu Gly Gln Cys Val Glu
 1               5                  10                  15 gga tcc atc gat cca cgt ttc cac gaa aac tgg ccg tct gcc ggc ggt    96
Gly Ser Ile Asp Pro Arg Phe His Glu Asn Trp Pro Ser Ala Gly Gly
             20                  25                  30 acc tct act tcc aaa gct tcc acc act acg act tct agc aaa acc acc   144
Thr Ser Thr Ser Lys Ala Ser Thr Thr Thr Ser Ser Lys Thr Thr
         35                  40                  45 act aca tcc tct aag act acc acg act acc tcc aaa acc tct act acc   192
Thr Thr Ser Ser Lys Thr Thr Thr Thr Ser Lys Thr Ser Thr Thr
 50                  55                  60 tct agc tcc tct acg ggc ggc gcc act cac aag acc tct act cag cgt   240
Ser Ser Ser Ser Thr Gly Gly Ala Thr His Lys Thr Ser Thr Gln Arg
 65                  70                  75                  80 ctg ctg gct gca taa tga                                            258
Leu Leu Ala Ala
```

<210> SEQ ID NO 229
<211> LENGTH: 84
<212> TYPE: PRT
<213> ORGANISM: artificial sequence
<220> FEATURE:
<223> OTHER INFORMATION: Synthetic Construct

<400> SEQUENCE: 229

```
Met Thr Cys Gly Val Gly Ser Thr Pro Ile Leu Gly Gln Cys Val Glu
1               5                   10                  15

Gly Ser Ile Asp Pro Arg Phe His Glu Asn Trp Pro Ser Ala Gly Gly
            20                  25                  30

Thr Ser Thr Ser Lys Ala Ser Thr Thr Thr Ser Lys Thr Thr
                35                  40                  45

Thr Thr Ser Ser Lys Thr Thr Thr Thr Thr Ser Lys Thr Ser Thr Thr
    50                  55                  60

Ser Ser Ser Ser Thr Gly Gly Ala Thr His Lys Thr Ser Thr Gln Arg
65              70                  75                  80

Leu Leu Ala Ala
```

<210> SEQ ID NO 230
<211> LENGTH: 258
<212> TYPE: DNA
<213> ORGANISM: artificial sequence
<220> FEATURE:
<223> OTHER INFORMATION: chimeric gene encoding fusion peptide
<220> FEATURE:
<221> NAME/KEY: CDS
<222> LOCATION: (1)..(258)

<400> SEQUENCE: 230

```
atg ttc ctg cgt cac cag tgc agc ccg acc gcg acc ccg tac tgc agc        48
Met Phe Leu Arg His Gln Cys Ser Pro Thr Ala Thr Pro Tyr Cys Ser
1               5                   10                  15 gga tcc atc gat cca cgt ttc cac gaa aac tgg ccg tct gcc ggc ggt        96
Gly Ser Ile Asp Pro Arg Phe His Glu Asn Trp Pro Ser Ala Gly Gly
            20                  25                  30 acc tct act tcc aaa gct tcc acc act acg act tct agc aaa acc acc       144
Thr Ser Thr Ser Lys Ala Ser Thr Thr Thr Thr Ser Ser Lys Thr Thr
                35                  40                  45 act aca tcc tct aag act acc acg act acc tcc aaa acc tct act acc       192
Thr Thr Ser Ser Lys Thr Thr Thr Thr Thr Ser Lys Thr Ser Thr Thr
    50                  55                  60 tct agc tcc tct acg ggc ggc gcc act cac aag acc tct act cag cgt       240
Ser Ser Ser Ser Thr Gly Gly Ala Thr His Lys Thr Ser Thr Gln Arg
65              70                  75                  80 ctg ctg gct gca taa tga                                                258
Leu Leu Ala Ala
```

<210> SEQ ID NO 231
<211> LENGTH: 84
<212> TYPE: PRT
<213> ORGANISM: artificial sequence
<220> FEATURE:
<223> OTHER INFORMATION: Synthetic Construct

<400> SEQUENCE: 231

```
Met Phe Leu Arg His Gln Cys Ser Pro Thr Ala Thr Pro Tyr Cys Ser
1               5                   10                  15

Gly Ser Ile Asp Pro Arg Phe His Glu Asn Trp Pro Ser Ala Gly Gly
            20                  25                  30

Thr Ser Thr Ser Lys Ala Ser Thr Thr Thr Ser Ser Lys Thr Thr
                35                  40                  45

Thr Thr Ser Ser Lys Thr Thr Thr Thr Ser Lys Thr Ser Thr Thr
    50                  55                  60

Ser Ser Ser Ser Thr Gly Gly Ala Thr His Lys Thr Ser Thr Gln Arg
65              70                  75                  80

Leu Leu Ala Ala
```

<210> SEQ ID NO 232
<211> LENGTH: 258
<212> TYPE: DNA
<213> ORGANISM: artificial sequence
<220> FEATURE:
<223> OTHER INFORMATION: chimeric gene encoding fusion peptide
<220> FEATURE:
<221> NAME/KEY: CDS
<222> LOCATION: (1)..(258)

<400> SEQUENCE: 232

```
atg ccg cag tgc cag agc ctg cgt cag cag tgc tgc cag cag ctg cgt        48
Met Pro Gln Cys Gln Ser Leu Arg Gln Gln Cys Cys Gln Gln Leu Arg
1               5                   10                  15 gga tcc atc gat cca cgt ttc cac gaa aac tgg ccg tct gcc ggc ggt        96
Gly Ser Ile Asp Pro Arg Phe His Glu Asn Trp Pro Ser Ala Gly Gly
            20                  25                  30 acc tct act tcc aaa gct tcc acc act acg act tct agc aaa acc acc       144
Thr Ser Thr Ser Lys Ala Ser Thr Thr Thr Thr Ser Ser Lys Thr Thr
        35                  40                  45 act aca tcc tct aag act acc acg act acc tcc aaa acc tct act acc       192
Thr Thr Ser Ser Lys Thr Thr Thr Thr Thr Ser Lys Thr Ser Thr Thr
    50                  55                  60 tct agc tcc tct acg ggc ggc gcc act cac aag acc tct act cag cgt       240
Ser Ser Ser Ser Thr Gly Gly Ala Thr His Lys Thr Ser Thr Gln Arg
65                  70                  75                  80 ctg ctg gct gca taa tga                                               258
Leu Leu Ala Ala
```

<210> SEQ ID NO 233
<211> LENGTH: 84
<212> TYPE: PRT
<213> ORGANISM: artificial sequence
<220> FEATURE:
<223> OTHER INFORMATION: Synthetic Construct

<400> SEQUENCE: 233

```
Met Pro Gln Cys Gln Ser Leu Arg Gln Gln Cys Cys Gln Gln Leu Arg
1               5                   10                  15

Gly Ser Ile Asp Pro Arg Phe His Glu Asn Trp Pro Ser Ala Gly Gly
            20                  25                  30

Thr Ser Thr Ser Lys Ala Ser Thr Thr Thr Thr Ser Ser Lys Thr Thr
        35                  40                  45

Thr Thr Ser Ser Lys Thr Thr Thr Thr Thr Ser Lys Thr Ser Thr Thr
    50                  55                  60

Ser Ser Ser Ser Thr Gly Gly Ala Thr His Lys Thr Ser Thr Gln Arg
65                  70                  75                  80

Leu Leu Ala Ala
```

<210> SEQ ID NO 234
<211> LENGTH: 258
<212> TYPE: DNA
<213> ORGANISM: artificial sequence
<220> FEATURE:
<223> OTHER INFORMATION: chimeric gene encoding fusion peptide
<220> FEATURE:
<221> NAME/KEY: CDS
<222> LOCATION: (1)..(258)

<400> SEQUENCE: 234

```
atg cag gtg gaa ccg cag cac cgt tac cag gcg atc ttc ggt ctg gtg        48
Met Gln Val Glu Pro Gln His Arg Tyr Gln Ala Ile Phe Gly Leu Val
```

```
1               5                  10                 15
gga tcc atc gat cca cgt ttc cac gaa aac tgg ccg tct gcc ggc ggt       96
Gly Ser Ile Asp Pro Arg Phe His Glu Asn Trp Pro Ser Ala Gly Gly
            20                  25                  30 acc tct act tcc aaa gct tcc acc act acg act tct agc aaa acc acc       144
Thr Ser Thr Ser Lys Ala Ser Thr Thr Thr Thr Ser Ser Lys Thr Thr
        35                  40                  45 act aca tcc tct aag act acc acg act acc tcc aaa acc tct act acc       192
Thr Thr Ser Ser Lys Thr Thr Thr Thr Thr Ser Lys Thr Ser Thr Thr
    50                  55                  60 tct agc tcc tct acg ggc ggc gcc act cac aag acc tct act cag cgt       240
Ser Ser Ser Ser Thr Gly Gly Ala Thr His Lys Thr Ser Thr Gln Arg
65                  70                  75                  80 ctg ctg gct gca taa tga                                               258
Leu Leu Ala Ala <210> SEQ ID NO 235
<211> LENGTH: 84
<212> TYPE: PRT
<213> ORGANISM: artificial sequence
<220> FEATURE:
<223> OTHER INFORMATION: Synthetic Construct

<400> SEQUENCE: 235

Met Gln Val Glu Pro Gln His Arg Tyr Gln Ala Ile Phe Gly Leu Val
1               5                   10                  15

Gly Ser Ile Asp Pro Arg Phe His Glu Asn Trp Pro Ser Ala Gly Gly
            20                  25                  30

Thr Ser Thr Ser Lys Ala Ser Thr Thr Thr Thr Ser Ser Lys Thr Thr
        35                  40                  45

Thr Thr Ser Ser Lys Thr Thr Thr Thr Thr Ser Lys Thr Ser Thr Thr
    50                  55                  60

Ser Ser Ser Ser Thr Gly Gly Ala Thr His Lys Thr Ser Thr Gln Arg
65                  70                  75                  80

Leu Leu Ala Ala

<210> SEQ ID NO 236
<211> LENGTH: 258
<212> TYPE: DNA
<213> ORGANISM: artificial sequence
<220> FEATURE:
<223> OTHER INFORMATION: chimeric gene encoding fusion peptide
<220> FEATURE:
<221> NAME/KEY: CDS
<222> LOCATION: (1)..(258)

<400> SEQUENCE: 236 atg ctg cag agc atc ctg cag cag cag ccg cag agc ggt cag gtg gcg       48
Met Leu Gln Ser Ile Leu Gln Gln Gln Pro Gln Ser Gly Gln Val Ala
1               5                   10                  15 gga tcc atc gat cca cgt ttc cac gaa aac tgg ccg tct gcc ggc ggt       96
Gly Ser Ile Asp Pro Arg Phe His Glu Asn Trp Pro Ser Ala Gly Gly
            20                  25                  30 acc tct act tcc aaa gct tcc acc act acg act tct agc aaa acc acc       144
Thr Ser Thr Ser Lys Ala Ser Thr Thr Thr Thr Ser Ser Lys Thr Thr
        35                  40                  45 act aca tcc tct aag act acc acg act acc tcc aaa acc tct act acc       192
Thr Thr Ser Ser Lys Thr Thr Thr Thr Thr Ser Lys Thr Ser Thr Thr
    50                  55                  60 tct agc tcc tct acg ggc ggc gcc act cac aag acc tct act cag cgt       240
Ser Ser Ser Ser Thr Gly Gly Ala Thr His Lys Thr Ser Thr Gln Arg
```

```
                 65                  70                  75                  80 ctg ctg gct gca taa tga                                                          258
Leu Leu Ala Ala <210> SEQ ID NO 237
<211> LENGTH: 84
<212> TYPE: PRT
<213> ORGANISM: artificial sequence
<220> FEATURE:
<223> OTHER INFORMATION: Synthetic Construct

<400> SEQUENCE: 237

Met Leu Gln Ser Ile Leu Gln Gln Gln Pro Gln Ser Gly Gln Val Ala
1               5                   10                  15

Gly Ser Ile Asp Pro Arg Phe His Glu Asn Trp Pro Ser Ala Gly Gly
            20                  25                  30

Thr Ser Thr Ser Lys Ala Ser Thr Thr Thr Ser Ser Lys Thr Thr
        35                  40                  45

Thr Thr Ser Ser Lys Thr Thr Thr Thr Ser Lys Thr Ser Thr Thr
    50                  55                  60

Ser Ser Ser Ser Thr Gly Gly Ala Thr His Lys Thr Ser Thr Gln Arg
65                  70                  75                  80

Leu Leu Ala Ala

<210> SEQ ID NO 238
<211> LENGTH: 258
<212> TYPE: DNA
<213> ORGANISM: artificial sequence
<220> FEATURE:
<223> OTHER INFORMATION: chimeric gene encoding fusion peptide
<220> FEATURE:
<221> NAME/KEY: CDS
<222> LOCATION: (1)..(258)

<400> SEQUENCE: 238 atg ggt ctg ctg gcg gcg cag atc gcg cag cag ctg acc gcg atg tgc     48
Met Gly Leu Leu Ala Ala Gln Ile Ala Gln Gln Leu Thr Ala Met Cys
1               5                   10                  15 gga tcc atc gat cca cgt ttc cac gaa aac tgg ccg tct gcc ggc ggt     96
Gly Ser Ile Asp Pro Arg Phe His Glu Asn Trp Pro Ser Ala Gly Gly
            20                  25                  30 acc tct act tcc aaa gct tcc acc act acg act tct agc aaa acc acc    144
Thr Ser Thr Ser Lys Ala Ser Thr Thr Thr Ser Ser Lys Thr Thr
        35                  40                  45 act aca tcc tct aag act acc acg act acc tcc aaa acc tct act acc    192
Thr Thr Ser Ser Lys Thr Thr Thr Thr Ser Lys Thr Ser Thr Thr
    50                  55                  60 tct agc tcc tct acg ggc ggc gcc act cac aag acc tct act cag cgt    240
Ser Ser Ser Ser Thr Gly Gly Ala Thr His Lys Thr Ser Thr Gln Arg
65                  70                  75                  80 ctg ctg gct gca taa tga                                             258
Leu Leu Ala Ala <210> SEQ ID NO 239
<211> LENGTH: 84
<212> TYPE: PRT
<213> ORGANISM: artificial sequence
<220> FEATURE:
<223> OTHER INFORMATION: Synthetic Construct

<400> SEQUENCE: 239

Met Gly Leu Leu Ala Ala Gln Ile Ala Gln Gln Leu Thr Ala Met Cys
```

```
                              1               5                  10                     15
Gly Ser Ile Asp Pro Arg Phe His Glu Asn Trp Pro Ser Ala Gly Gly
                20                   25                    30

Thr Ser Thr Ser Lys Ala Ser Thr Thr Thr Ser Ser Lys Thr Thr
           35                   40                    45

Thr Thr Ser Ser Lys Thr Thr Thr Thr Thr Ser Lys Thr Ser Thr Thr
           50                   55                    60

Ser Ser Ser Ser Thr Gly Gly Ala Thr His Lys Thr Ser Thr Gln Arg
65                   70                    75                    80

Leu Leu Ala Ala

<210> SEQ ID NO 240
<211> LENGTH: 258
<212> TYPE: DNA
<213> ORGANISM: artificial sequence
<220> FEATURE:
<223> OTHER INFORMATION: chimeric gene encoding fusion peptide
<220> FEATURE:
<221> NAME/KEY: CDS
<222> LOCATION: (1)..(258)

<400> SEQUENCE: 240 atg ggt ctg cag cag ccg acc ccg tgc ccg tac gcg gcg gcg ggt ggt        48
Met Gly Leu Gln Gln Pro Thr Pro Cys Pro Tyr Ala Ala Ala Gly Gly
1               5                   10                    15 gga tcc atc gat cca cgt ttc cac gaa aac tgg ccg tct gcc ggc ggt        96
Gly Ser Ile Asp Pro Arg Phe His Glu Asn Trp Pro Ser Ala Gly Gly
                20                  25                    30 acc tct act tcc aaa gct tcc acc act acg act tct agc aaa acc acc       144
Thr Ser Thr Ser Lys Ala Ser Thr Thr Thr Thr Ser Ser Lys Thr Thr
            35                  40                    45 act aca tcc tct aag act acc acg act acc tcc aaa acc tct act acc       192
Thr Thr Ser Ser Lys Thr Thr Thr Thr Thr Ser Lys Thr Ser Thr Thr
            50                  55                    60 tct agc tcc tct acg ggc ggc gcc act cac aag acc tct act cag cgt       240
Ser Ser Ser Ser Thr Gly Gly Ala Thr His Lys Thr Ser Thr Gln Arg
65                  70                    75                    80 ctg ctg gct gca taa tga                                                258
Leu Leu Ala Ala <210> SEQ ID NO 241
<211> LENGTH: 84
<212> TYPE: PRT
<213> ORGANISM: artificial sequence
<220> FEATURE:
<223> OTHER INFORMATION: Synthetic Construct

<400> SEQUENCE: 241

Met Gly Leu Gln Gln Pro Thr Pro Cys Pro Tyr Ala Ala Ala Gly Gly
1               5                   10                    15

Gly Ser Ile Asp Pro Arg Phe His Glu Asn Trp Pro Ser Ala Gly Gly
                20                  25                    30

Thr Ser Thr Ser Lys Ala Ser Thr Thr Thr Ser Ser Lys Thr Thr
            35                  40                    45

Thr Thr Ser Ser Lys Thr Thr Thr Thr Thr Ser Lys Thr Ser Thr Thr
            50                  55                    60

Ser Ser Ser Ser Thr Gly Gly Ala Thr His Lys Thr Ser Thr Gln Arg
65                  70                    75                    80

Leu Leu Ala Ala
```

<210> SEQ ID NO 242
<211> LENGTH: 288
<212> TYPE: DNA
<213> ORGANISM: artificial sequence
<220> FEATURE:
<223> OTHER INFORMATION: chimeric gene encoding fusion peptide
<220> FEATURE:
<221> NAME/KEY: CDS
<222> LOCATION: (1)..(288)

<400> SEQUENCE: 242

```
atg ccg acc cag ccg ccg cgt ccg cag ccg cac ccg cag ccg cac ccg      48
Met Pro Thr Gln Pro Pro Arg Pro Gln Pro His Pro Gln Pro His Pro
1               5                   10                  15 tgc ccg tgc cag cag ccg cac ccg agc ccg gga tcc atc gat cca cgt      96
Cys Pro Cys Gln Gln Pro His Pro Ser Pro Gly Ser Ile Asp Pro Arg
                20                  25                  30 ttc cac gaa aac tgg ccg tct gcc ggc ggt acc tct act tcc aaa gct     144
Phe His Glu Asn Trp Pro Ser Ala Gly Gly Thr Ser Thr Ser Lys Ala
            35                  40                  45 tcc acc act acg act tct agc aaa acc acc act aca tcc tct aag act     192
Ser Thr Thr Thr Thr Ser Ser Lys Thr Thr Thr Thr Ser Ser Lys Thr
        50                  55                  60 acc acg act acc tcc aaa acc tct act acc tct agc tcc tct acg ggc     240
Thr Thr Thr Thr Ser Lys Thr Ser Thr Thr Ser Ser Ser Ser Thr Gly
65                  70                  75                  80 ggc gcc act cac aag acc tct act cag cgt ctg ctg gct gca taa tga     288
Gly Ala Thr His Lys Thr Ser Thr Gln Arg Leu Leu Ala Ala
                85                  90
```

<210> SEQ ID NO 243
<211> LENGTH: 94
<212> TYPE: PRT
<213> ORGANISM: artificial sequence
<220> FEATURE:
<223> OTHER INFORMATION: Synthetic Construct

<400> SEQUENCE: 243

```
Met Pro Thr Gln Pro Pro Arg Pro Gln Pro His Pro Gln Pro His Pro
1               5                   10                  15

Cys Pro Cys Gln Gln Pro His Pro Ser Pro Gly Ser Ile Asp Pro Arg
                20                  25                  30

Phe His Glu Asn Trp Pro Ser Ala Gly Gly Thr Ser Thr Ser Lys Ala
            35                  40                  45

Ser Thr Thr Thr Thr Ser Ser Lys Thr Thr Thr Thr Ser Ser Lys Thr
        50                  55                  60

Thr Thr Thr Thr Ser Lys Thr Ser Thr Thr Ser Ser Ser Ser Thr Gly
65                  70                  75                  80

Gly Ala Thr His Lys Thr Ser Thr Gln Arg Leu Leu Ala Ala
                85                  90
```

<210> SEQ ID NO 244
<211> LENGTH: 273
<212> TYPE: DNA
<213> ORGANISM: artificial sequence
<220> FEATURE:
<223> OTHER INFORMATION: chimeric gene encoding fusion peptide
<220> FEATURE:
<221> NAME/KEY: CDS
<222> LOCATION: (1)..(273)

<400> SEQUENCE: 244

```
atg cgt ccg cag ccg cac ccg cag ccg cac ccg tgc ccg tgc cag cag      48
```

```
Met Arg Pro Gln Pro His Pro Gln Pro His Pro Cys Pro Cys Gln Gln
 1               5                  10                  15 ccg cac ccg agc ccg gga tcc atc gat cca cgt ttc cac gaa aac tgg        96
Pro His Pro Ser Pro Gly Ser Ile Asp Pro Arg Phe His Glu Asn Trp
                20                  25                  30 ccg tct gcc ggc ggt acc tct act tcc aaa gct tcc act act acg act       144
Pro Ser Ala Gly Gly Thr Ser Thr Ser Lys Ala Ser Thr Thr Thr Thr
                35                  40                  45 tct agc aaa acc acc act aca tcc tct aag act acc acg act acc tcc       192
Ser Ser Lys Thr Thr Thr Thr Ser Ser Lys Thr Thr Thr Thr Thr Ser
        50                  55                  60 aaa acc tct act acc tct agc tcc tct acg ggc ggc gcc act cac aag       240
Lys Thr Ser Thr Thr Ser Ser Ser Ser Thr Gly Gly Ala Thr His Lys
65                  70                  75                  80 acc tct act cag cgt ctg ctg gct gca taa tga                           273
Thr Ser Thr Gln Arg Leu Leu Ala Ala
                85
```

<210> SEQ ID NO 245
<211> LENGTH: 89
<212> TYPE: PRT
<213> ORGANISM: artificial sequence
<220> FEATURE:
<223> OTHER INFORMATION: Synthetic Construct

<400> SEQUENCE: 245

```
Met Arg Pro Gln Pro His Pro Gln Pro His Pro Cys Pro Cys Gln Gln
 1               5                  10                  15

Pro His Pro Ser Pro Gly Ser Ile Asp Pro Arg Phe His Glu Asn Trp
                20                  25                  30

Pro Ser Ala Gly Gly Thr Ser Thr Ser Lys Ala Ser Thr Thr Thr Thr
                35                  40                  45

Ser Ser Lys Thr Thr Thr Thr Ser Ser Lys Thr Thr Thr Thr Thr Ser
        50                  55                  60

Lys Thr Ser Thr Thr Ser Ser Ser Ser Thr Gly Gly Ala Thr His Lys
65                  70                  75                  80

Thr Ser Thr Gln Arg Leu Leu Ala Ala
                85
```

<210> SEQ ID NO 246
<211> LENGTH: 11
<212> TYPE: PRT
<213> ORGANISM: artificial sequence
<220> FEATURE:
<223> OTHER INFORMATION: T7 Translation enhancer element

<400> SEQUENCE: 246

```
Met Ala Ser Met Thr Gly Gly Gln Gln Met Gly
 1               5                  10
```

<210> SEQ ID NO 247
<211> LENGTH: 41
<212> TYPE: PRT
<213> ORGANISM: artificial sequence
<220> FEATURE:
<223> OTHER INFORMATION: IBT-180 tag

<400> SEQUENCE: 247

```
Met Ala Ser Met Thr Gly Gly Gln Gln Met Gly Val His Leu Pro Pro
 1               5                  10                  15

Pro Pro Cys His Tyr Pro Thr Gln Pro Pro Arg Pro Gln Pro His Pro
                20                  25                  30
```

```
Gln Pro His Pro Cys Pro Cys Gln Gln
        35                  40

<210> SEQ ID NO 248
<211> LENGTH: 111
<212> TYPE: PRT
<213> ORGANISM: artificial sequence
<220> FEATURE:
<223> OTHER INFORMATION: IBT-181 tag

<400> SEQUENCE: 248

Met Ala Ser Met Thr Gly Gly Gln Gln Met Gly Val His Leu Pro Pro
1               5                  10                  15

Pro Pro Cys His Tyr Pro Thr Gln Pro Pro Arg Pro Gln Pro His Pro
            20                  25                  30

Gln Pro His Pro Cys Pro Cys Gln Gln Pro His Pro Ser Pro Cys Gln
        35                  40                  45

Leu Gln Gly Thr Cys Gly Val Gly Ser Thr Pro Ile Leu Gly Gln Cys
    50                  55                  60

Val Glu Phe Leu Arg His Gln Cys Ser Pro Thr Ala Thr Pro Tyr Cys
65                  70                  75                  80

Ser Pro Gln Cys Gln Ser Leu Arg Gln Gln Cys Cys Gln Gln Leu Arg
                85                  90                  95

Gln Val Glu Pro Gln His Arg Tyr Gln Ala Ile Phe Gly Leu Val
            100                 105                 110

<210> SEQ ID NO 249
<211> LENGTH: 333
<212> TYPE: DNA
<213> ORGANISM: artificial sequence
<220> FEATURE:
<223> OTHER INFORMATION: chimeric gene encoding a fusion peptide
<220> FEATURE:
<221> NAME/KEY: CDS
<222> LOCATION: (1)..(333)

<400> SEQUENCE: 249 atg gct agc atg act ggt gga cag caa atg ggt gtg cat ctg cca cct      48
Met Ala Ser Met Thr Gly Gly Gln Gln Met Gly Val His Leu Pro Pro
1               5                  10                  15 cca cct tgc cat tac cct act caa ccg cct cgt cca cag cca cac cct      96
Pro Pro Cys His Tyr Pro Thr Gln Pro Pro Arg Pro Gln Pro His Pro
            20                  25                  30 cag ccg cat ccg tgt cca tgc caa cag gga tcc atc gat cca cgt ttc     144
Gln Pro His Pro Cys Pro Cys Gln Gln Gly Ser Ile Asp Pro Arg Phe
        35                  40                  45 cac gaa aac tgg ccg tct gcc ggc ggt acc tct act tcc aaa gct tcc     192
His Glu Asn Trp Pro Ser Ala Gly Gly Thr Ser Thr Ser Lys Ala Ser
    50                  55                  60 acc act acg act tct agc aaa acc acc act aca tcc tct aag act acc     240
Thr Thr Thr Thr Ser Ser Lys Thr Thr Thr Ser Ser Lys Thr Thr
65                  70                  75                  80 acg act acc tcc aaa acc tct act acc tct agc tcc tct acg ggc ggc     288
Thr Thr Thr Ser Lys Thr Ser Thr Thr Ser Ser Ser Thr Gly Gly
                85                  90                  95 gcc act cac aag acc tct act cag cgt ctg ctg gct gca taa tga          333
Ala Thr His Lys Thr Ser Thr Gln Arg Leu Leu Ala Ala
            100                 105

<210> SEQ ID NO 250
<211> LENGTH: 109
```

```
<212> TYPE: PRT
<213> ORGANISM: artificial sequence
<220> FEATURE:
<223> OTHER INFORMATION: Synthetic Construct

<400> SEQUENCE: 250

Met Ala Ser Met Thr Gly Gly Gln Gln Met Gly Val His Leu Pro Pro
1               5                   10                  15

Pro Pro Cys His Tyr Pro Thr Gln Pro Pro Arg Pro Gln Pro His Pro
            20                  25                  30

Gln Pro His Pro Cys Pro Cys Gln Gln Gly Ser Ile Asp Pro Arg Phe
        35                  40                  45

His Glu Asn Trp Pro Ser Ala Gly Gly Thr Ser Thr Ser Lys Ala Ser
    50                  55                  60

Thr Thr Thr Thr Ser Ser Lys Thr Thr Thr Thr Ser Ser Lys Thr Thr
65                  70                  75                  80

Thr Thr Thr Ser Lys Thr Ser Thr Thr Ser Ser Ser Thr Gly Gly
                85                  90                  95

Ala Thr His Lys Thr Ser Thr Gln Arg Leu Leu Ala Ala
            100                 105

<210> SEQ ID NO 251
<211> LENGTH: 543
<212> TYPE: DNA
<213> ORGANISM: artificial sequence
<220> FEATURE:
<223> OTHER INFORMATION: chimeric gene encoding the fusion peptide
<220> FEATURE:
<221> NAME/KEY: CDS
<222> LOCATION: (1)..(543)

<400> SEQUENCE: 251 atg gct agc atg act ggt gga cag caa atg ggt gtt cac ctg ccg ccg      48
Met Ala Ser Met Thr Gly Gly Gln Gln Met Gly Val His Leu Pro Pro
1               5                   10                  15 cca cct tgt cat tat ccg acg caa cct cca cgt ccg caa ccg cat ccg      96
Pro Pro Cys His Tyr Pro Thr Gln Pro Pro Arg Pro Gln Pro His Pro
            20                  25                  30 cag ccg cac ccg tgt ccg tgc cag cag cct cac ccg tct cca tgc caa     144
Gln Pro His Pro Cys Pro Cys Gln Gln Pro His Pro Ser Pro Cys Gln
        35                  40                  45 ctg cag ggc acg tgt ggt gtg ggc tcc acg ccg att ctg ggc cag tgt     192
Leu Gln Gly Thr Cys Gly Val Gly Ser Thr Pro Ile Leu Gly Gln Cys
    50                  55                  60 gtg gag ttc ctg cgt cat cag tgc agc ccg acg gca act ccg tat tgc     240
Val Glu Phe Leu Arg His Gln Cys Ser Pro Thr Ala Thr Pro Tyr Cys
65                  70                  75                  80 tct ccg cag tgc cag tcc ctg cgc caa cag tgt tgt cag cag ctg cgt     288
Ser Pro Gln Cys Gln Ser Leu Arg Gln Gln Cys Cys Gln Gln Leu Arg
                85                  90                  95 caa gtt gag cca caa cac cgc tat caa gct att ttc ggt ctg gtt gga     336
Gln Val Glu Pro Gln His Arg Tyr Gln Ala Ile Phe Gly Leu Val Gly
            100                 105                 110 tcc atc gat cca cgt ttc cac gaa aac tgg ccg tct gcc ggc ggt acc     384
Ser Ile Asp Pro Arg Phe His Glu Asn Trp Pro Ser Ala Gly Gly Thr
        115                 120                 125 tct act tcc aaa gct tcc acc act acg act tct agc aaa acc acc act     432
Ser Thr Ser Lys Ala Ser Thr Thr Thr Thr Ser Ser Lys Thr Thr Thr
    130                 135                 140 aca tcc tct aag act acc acg act acc tcc aaa acc tct act acc tct     480
Thr Ser Ser Lys Thr Thr Thr Thr Thr Ser Lys Thr Ser Thr Thr Ser
```

```
                    145                 150                 155                 160
agc tcc tct acg ggc ggc gcc act cac aag acc tct act cag cgt ctg          528
Ser Ser Ser Thr Gly Gly Ala Thr His Lys Thr Ser Thr Gln Arg Leu
                    165                 170                 175 ctg gct gca taa tga                                                      543
Leu Ala Ala <210> SEQ ID NO 252
<211> LENGTH: 179
<212> TYPE: PRT
<213> ORGANISM: artificial sequence
<220> FEATURE:
<223> OTHER INFORMATION: Synthetic Construct

<400> SEQUENCE: 252

Met Ala Ser Met Thr Gly Gly Gln Gln Met Gly Val His Leu Pro Pro
1               5                   10                  15

Pro Pro Cys His Tyr Pro Thr Gln Pro Pro Arg Pro Gln Pro His Pro
                20                  25                  30

Gln Pro His Pro Cys Pro Cys Gln Gln Pro His Pro Ser Pro Cys Gln
            35                  40                  45

Leu Gln Gly Thr Cys Gly Val Gly Ser Thr Pro Ile Leu Gly Gln Cys
        50                  55                  60

Val Glu Phe Leu Arg His Gln Cys Ser Pro Thr Ala Thr Pro Tyr Cys
65                  70                  75                  80

Ser Pro Gln Cys Gln Ser Leu Arg Gln Gln Cys Cys Gln Gln Leu Arg
                85                  90                  95

Gln Val Glu Pro Gln His Arg Tyr Gln Ala Ile Phe Gly Leu Val Gly
                100                 105                 110

Ser Ile Asp Pro Arg Phe His Glu Asn Trp Pro Ser Ala Gly Gly Thr
            115                 120                 125

Ser Thr Ser Lys Ala Ser Thr Thr Thr Ser Ser Lys Thr Thr Thr
        130                 135                 140

Thr Ser Ser Lys Thr Thr Thr Thr Ser Lys Thr Ser Thr Thr Ser
145                 150                 155                 160

Ser Ser Ser Thr Gly Gly Ala Thr His Lys Thr Ser Thr Gln Arg Leu
                165                 170                 175

Leu Ala Ala

<210> SEQ ID NO 253
<211> LENGTH: 7
<212> TYPE: PRT
<213> ORGANISM: artificial sequence
<220> FEATURE:
<223> OTHER INFORMATION: skin binding peptide

<400> SEQUENCE: 253

Phe Thr Gln Ser Leu Pro Arg
1               5

<210> SEQ ID NO 254
<211> LENGTH: 12
<212> TYPE: PRT
<213> ORGANISM: artificial sequence
<220> FEATURE:
<223> OTHER INFORMATION: skin binding peptide

<400> SEQUENCE: 254

Thr Pro Phe His Ser Pro Glu Asn Ala Pro Gly Ser
1               5                   10
```

```
<210> SEQ ID NO 255
<211> LENGTH: 12
<212> TYPE: PRT
<213> ORGANISM: artificial sequence
<220> FEATURE:
<223> OTHER INFORMATION: skin binding peptide

<400> SEQUENCE: 255

Lys Gln Ala Thr Phe Pro Pro Asn Pro Thr Ala Tyr
1               5                   10

<210> SEQ ID NO 256
<211> LENGTH: 12
<212> TYPE: PRT
<213> ORGANISM: artificial sequence
<220> FEATURE:
<223> OTHER INFORMATION: skin binding peptide

<400> SEQUENCE: 256

His Gly His Met Val Ser Thr Ser Gln Leu Ser Ile
1               5                   10

<210> SEQ ID NO 257
<211> LENGTH: 7
<212> TYPE: PRT
<213> ORGANISM: artificial sequence
<220> FEATURE:
<223> OTHER INFORMATION: skin binding peptide

<400> SEQUENCE: 257

Leu Ser Pro Ser Arg Met Lys
1               5

<210> SEQ ID NO 258
<211> LENGTH: 7
<212> TYPE: PRT
<213> ORGANISM: artificial sequence
<220> FEATURE:
<223> OTHER INFORMATION: skin binding peptide

<400> SEQUENCE: 258

Leu Pro Ile Pro Arg Met Lys
1               5

<210> SEQ ID NO 259
<211> LENGTH: 7
<212> TYPE: PRT
<213> ORGANISM: artificial sequence
<220> FEATURE:
<223> OTHER INFORMATION: skin binding peptide

<400> SEQUENCE: 259

His Gln Arg Pro Tyr Leu Thr
1               5

<210> SEQ ID NO 260
<211> LENGTH: 7
<212> TYPE: PRT
<213> ORGANISM: artificial sequence
<220> FEATURE:
<223> OTHER INFORMATION: skin binding peptide

<400> SEQUENCE: 260

Phe Pro Pro Leu Leu Arg Leu
1               5
```

```
<210> SEQ ID NO 261
<211> LENGTH: 12
<212> TYPE: PRT
<213> ORGANISM: artificial sequence
<220> FEATURE:
<223> OTHER INFORMATION: hair binding peptide

<400> SEQUENCE: 261

Ser Val Ser Val Gly Met Lys Pro Ser Pro Arg Pro
1               5                   10

<210> SEQ ID NO 262
<211> LENGTH: 12
<212> TYPE: PRT
<213> ORGANISM: artificial sequence
<220> FEATURE:
<223> OTHER INFORMATION: hair binding peptide

<400> SEQUENCE: 262

Leu Asp Val Glu Ser Tyr Lys Gly Thr Ser Met Pro
1               5                   10

<210> SEQ ID NO 263
<211> LENGTH: 12
<212> TYPE: PRT
<213> ORGANISM: artificial sequence
<220> FEATURE:
<223> OTHER INFORMATION: hair binding peptide

<400> SEQUENCE: 263

Arg Val Pro Asn Lys Thr Val Thr Val Asp Gly Ala
1               5                   10

<210> SEQ ID NO 264
<211> LENGTH: 12
<212> TYPE: PRT
<213> ORGANISM: artificial sequence
<220> FEATURE:
<223> OTHER INFORMATION: hair binding peptide

<400> SEQUENCE: 264

Asp Arg His Lys Ser Lys Tyr Ser Ser Thr Lys Ser
1               5                   10

<210> SEQ ID NO 265
<211> LENGTH: 12
<212> TYPE: PRT
<213> ORGANISM: artificial sequence
<220> FEATURE:
<223> OTHER INFORMATION: hair binding peptide

<400> SEQUENCE: 265

Lys Asn Phe Pro Gln Gln Lys Glu Phe Pro Leu Ser
1               5                   10

<210> SEQ ID NO 266
<211> LENGTH: 12
<212> TYPE: PRT
<213> ORGANISM: artificial sequence
<220> FEATURE:
<223> OTHER INFORMATION: hair binding peptide

<400> SEQUENCE: 266

Gln Arg Asn Ser Pro Pro Ala Met Ser Arg Arg Asp
1               5                   10
```

```
<210> SEQ ID NO 267
<211> LENGTH: 12
<212> TYPE: PRT
<213> ORGANISM: artificial sequence
<220> FEATURE:
<223> OTHER INFORMATION: hair binding peptide

<400> SEQUENCE: 267

Thr Arg Lys Pro Asn Met Pro His Gly Gln Tyr Leu
1               5                   10

<210> SEQ ID NO 268
<211> LENGTH: 12
<212> TYPE: PRT
<213> ORGANISM: artificial sequence
<220> FEATURE:
<223> OTHER INFORMATION: hair binding peptide

<400> SEQUENCE: 268

Lys Pro Pro His Leu Ala Lys Leu Pro Phe Thr Thr
1               5                   10

<210> SEQ ID NO 269
<211> LENGTH: 12
<212> TYPE: PRT
<213> ORGANISM: artificial sequence
<220> FEATURE:
<223> OTHER INFORMATION: hair binding peptide

<400> SEQUENCE: 269

Asn Lys Arg Pro Pro Thr Ser His Arg Ile His Ala
1               5                   10

<210> SEQ ID NO 270
<211> LENGTH: 12
<212> TYPE: PRT
<213> ORGANISM: artificial sequence
<220> FEATURE:
<223> OTHER INFORMATION: hair binding peptide

<400> SEQUENCE: 270

Asn Leu Pro Arg Tyr Gln Pro Pro Cys Lys Pro Leu
1               5                   10

<210> SEQ ID NO 271
<211> LENGTH: 12
<212> TYPE: PRT
<213> ORGANISM: artificial sequence
<220> FEATURE:
<223> OTHER INFORMATION: hair binding peptide

<400> SEQUENCE: 271

Arg Pro Pro Trp Lys Lys Pro Ile Pro Pro Ser Glu
1               5                   10

<210> SEQ ID NO 272
<211> LENGTH: 12
<212> TYPE: PRT
<213> ORGANISM: artificial sequence
<220> FEATURE:
<223> OTHER INFORMATION: hair binding peptide

<400> SEQUENCE: 272

Arg Gln Arg Pro Lys Asp His Phe Phe Ser Arg Pro
1               5                   10

<210> SEQ ID NO 273
```

```
<211> LENGTH: 12
<212> TYPE: PRT
<213> ORGANISM: artificial sequence
<220> FEATURE:
<223> OTHER INFORMATION: hair binding peptide
<220> FEATURE:
<221> NAME/KEY: MISC_FEATURE
<222> LOCATION: (6)..(6)
<223> OTHER INFORMATION: Xaa= Thr or Pro
<220> FEATURE:
<221> NAME/KEY: MISC_FEATURE
<222> LOCATION: (12)..(12)
<223> OTHER INFORMATION: Xaa= Glu or Ala

<400> SEQUENCE: 273

Ser Val Pro Asn Lys Xaa Val Thr Val Asp Gly Xaa
1               5                   10

<210> SEQ ID NO 274
<211> LENGTH: 12
<212> TYPE: PRT
<213> ORGANISM: artificial sequence
<220> FEATURE:
<223> OTHER INFORMATION: hair binding peptide

<400> SEQUENCE: 274

Thr Thr Lys Trp Arg His Arg Ala Pro Val Ser Pro
1               5                   10

<210> SEQ ID NO 275
<211> LENGTH: 12
<212> TYPE: PRT
<213> ORGANISM: artificial sequence
<220> FEATURE:
<223> OTHER INFORMATION: hair binding peptide

<400> SEQUENCE: 275

Trp Leu Gly Lys Asn Arg Ile Lys Pro Arg Ala Ser
1               5                   10

<210> SEQ ID NO 276
<211> LENGTH: 12
<212> TYPE: PRT
<213> ORGANISM: artificial sequence
<220> FEATURE:
<223> OTHER INFORMATION: hair binding peptide

<400> SEQUENCE: 276

Ser Asn Phe Lys Thr Pro Leu Pro Leu Thr Gln Ser
1               5                   10

<210> SEQ ID NO 277
<211> LENGTH: 12
<212> TYPE: PRT
<213> ORGANISM: artificial sequence
<220> FEATURE:
<223> OTHER INFORMATION: hair binding peptide

<400> SEQUENCE: 277

Lys Glu Leu Gln Thr Arg Asn Val Val Gln Arg Glu
1               5                   10

<210> SEQ ID NO 278
<211> LENGTH: 12
<212> TYPE: PRT
<213> ORGANISM: artificial sequence
<220> FEATURE:
<223> OTHER INFORMATION: hair binding peptide
```

```
<400> SEQUENCE: 278

Gly Met Pro Ala Met His Trp Ile His Pro Phe Ala
1               5                   10

<210> SEQ ID NO 279
<211> LENGTH: 12
<212> TYPE: PRT
<213> ORGANISM: artificial sequence
<220> FEATURE:
<223> OTHER INFORMATION: hair binding peptide

<400> SEQUENCE: 279

Thr Pro Thr Ala Asn Gln Phe Thr Gln Ser Val Pro
1               5                   10

<210> SEQ ID NO 280
<211> LENGTH: 12
<212> TYPE: PRT
<213> ORGANISM: artificial sequence
<220> FEATURE:
<223> OTHER INFORMATION: hair binding peptide

<400> SEQUENCE: 280

Ala Ala Gly Leu Ser Gln Lys His Glu Arg Asn Arg
1               5                   10

<210> SEQ ID NO 281
<211> LENGTH: 12
<212> TYPE: PRT
<213> ORGANISM: artificial sequence
<220> FEATURE:
<223> OTHER INFORMATION: hair binding peptide

<400> SEQUENCE: 281

Glu Thr Val His Gln Thr Pro Leu Ser Asp Arg Pro
1               5                   10

<210> SEQ ID NO 282
<211> LENGTH: 12
<212> TYPE: PRT
<213> ORGANISM: artificial sequence
<220> FEATURE:
<223> OTHER INFORMATION: hair binding peptide

<400> SEQUENCE: 282

Leu Pro Ala Leu His Ile Gln Arg His Pro Arg Met
1               5                   10

<210> SEQ ID NO 283
<211> LENGTH: 12
<212> TYPE: PRT
<213> ORGANISM: artificial sequence
<220> FEATURE:
<223> OTHER INFORMATION: hair binding peptide

<400> SEQUENCE: 283

Gln Pro Ser His Ser Gln Ser His Asn Leu Arg Ser
1               5                   10

<210> SEQ ID NO 284
<211> LENGTH: 12
<212> TYPE: PRT
<213> ORGANISM: artificial sequence
<220> FEATURE:
<223> OTHER INFORMATION: hair binding peptide

<400> SEQUENCE: 284
```

```
Arg Gly Ser Gln Lys Ser Lys Pro Pro Arg Pro Pro
1               5                   10
```

<210> SEQ ID NO 285
<211> LENGTH: 12
<212> TYPE: PRT
<213> ORGANISM: artificial sequence
<220> FEATURE:
<223> OTHER INFORMATION: hair binding peptide

<400> SEQUENCE: 285

```
Thr His Thr Gln Lys Thr Pro Leu Leu Tyr Tyr His
1               5                   10
```

<210> SEQ ID NO 286
<211> LENGTH: 12
<212> TYPE: PRT
<213> ORGANISM: artificial sequence
<220> FEATURE:
<223> OTHER INFORMATION: hair binding peptide

<400> SEQUENCE: 286

```
Thr Lys Gly Ser Ser Gln Ala Ile Leu Lys Ser Thr
1               5                   10
```

<210> SEQ ID NO 287
<211> LENGTH: 7
<212> TYPE: PRT
<213> ORGANISM: artificial sequence
<220> FEATURE:
<223> OTHER INFORMATION: hair binding peptide

<400> SEQUENCE: 287

```
Asp Leu His Thr Val Tyr His
1               5
```

<210> SEQ ID NO 288
<211> LENGTH: 7
<212> TYPE: PRT
<213> ORGANISM: artificial sequence
<220> FEATURE:
<223> OTHER INFORMATION: hair binding peptide

<400> SEQUENCE: 288

```
His Ile Lys Pro Pro Thr Arg
1               5
```

<210> SEQ ID NO 289
<211> LENGTH: 7
<212> TYPE: PRT
<213> ORGANISM: artificial sequence
<220> FEATURE:
<223> OTHER INFORMATION: hair binding peptide

<400> SEQUENCE: 289

```
His Pro Val Trp Pro Ala Ile
1               5
```

<210> SEQ ID NO 290
<211> LENGTH: 7
<212> TYPE: PRT
<213> ORGANISM: artificial sequence
<220> FEATURE:
<223> OTHER INFORMATION: hair binding peptide

<400> SEQUENCE: 290

```
Met Pro Leu Tyr Tyr Leu Gln
1               5

<210> SEQ ID NO 291
<211> LENGTH: 26
<212> TYPE: PRT
<213> ORGANISM: artificial sequence
<220> FEATURE:
<223> OTHER INFORMATION: hair binding peptide

<400> SEQUENCE: 291

His Leu Thr Val Pro Trp Arg Gly Gly Gly Ser Ala Val Pro Phe Tyr
1               5                   10                  15

Ser His Ser Gln Ile Thr Leu Pro Asn His
            20                  25

<210> SEQ ID NO 292
<211> LENGTH: 41
<212> TYPE: PRT
<213> ORGANISM: artificial sequence
<220> FEATURE:
<223> OTHER INFORMATION: hair binding peptide

<400> SEQUENCE: 292

Gly Pro His Asp Thr Ser Ser Gly Gly Val Arg Pro Asn Leu His His
1               5                   10                  15

Thr Ser Lys Lys Glu Lys Arg Glu Asn Arg Lys Val Pro Phe Tyr Ser
            20                  25                  30

His Ser Val Thr Ser Arg Gly Asn Val
        35                  40

<210> SEQ ID NO 293
<211> LENGTH: 7
<212> TYPE: PRT
<213> ORGANISM: artificial sequence
<220> FEATURE:
<223> OTHER INFORMATION: hair binding peptide

<400> SEQUENCE: 293

Lys His Pro Thr Tyr Arg Gln
1               5

<210> SEQ ID NO 294
<211> LENGTH: 7
<212> TYPE: PRT
<213> ORGANISM: artificial sequence
<220> FEATURE:
<223> OTHER INFORMATION: hair binding peptide

<400> SEQUENCE: 294

His Pro Met Ser Ala Pro Arg
1               5

<210> SEQ ID NO 295
<211> LENGTH: 7
<212> TYPE: PRT
<213> ORGANISM: artificial sequence
<220> FEATURE:
<223> OTHER INFORMATION: hair binding peptide

<400> SEQUENCE: 295

Met Pro Lys Tyr Tyr Leu Gln
1               5

<210> SEQ ID NO 296
```

```
<211> LENGTH: 7
<212> TYPE: PRT
<213> ORGANISM: artificial sequence
<220> FEATURE:
<223> OTHER INFORMATION: hair binding peptide

<400> SEQUENCE: 296

Met His Ala His Ser Ile Ala
1               5

<210> SEQ ID NO 297
<211> LENGTH: 7
<212> TYPE: PRT
<213> ORGANISM: artificial sequence
<220> FEATURE:
<223> OTHER INFORMATION: hair binding peptide

<400> SEQUENCE: 297

Thr Ala Ala Thr Thr Ser Pro
1               5

<210> SEQ ID NO 298
<211> LENGTH: 7
<212> TYPE: PRT
<213> ORGANISM: artificial sequence
<220> FEATURE:
<223> OTHER INFORMATION: hair binding peptide

<400> SEQUENCE: 298

Leu Gly Ile Pro Gln Asn Leu
1               5

<210> SEQ ID NO 299
<211> LENGTH: 12
<212> TYPE: PRT
<213> ORGANISM: artificial sequence
<220> FEATURE:
<223> OTHER INFORMATION: hair binding peptide

<400> SEQUENCE: 299

Ala Lys Pro Ile Ser Gln His Leu Gln Arg Gly Ser
1               5                   10

<210> SEQ ID NO 300
<211> LENGTH: 12
<212> TYPE: PRT
<213> ORGANISM: artificial sequence
<220> FEATURE:
<223> OTHER INFORMATION: hair binding peptide

<400> SEQUENCE: 300

Ala Pro Pro Thr Pro Ala Ala Ala Ser Ala Thr Thr
1               5                   10

<210> SEQ ID NO 301
<211> LENGTH: 12
<212> TYPE: PRT
<213> ORGANISM: artificial sequence
<220> FEATURE:
<223> OTHER INFORMATION: hair binding peptide

<400> SEQUENCE: 301

Asp Pro Thr Glu Gly Ala Arg Arg Thr Ile Met Thr
1               5                   10

<210> SEQ ID NO 302
<211> LENGTH: 12
```

```
<212> TYPE: PRT
<213> ORGANISM: artificial sequence
<220> FEATURE:
<223> OTHER INFORMATION: hair binding peptide

<400> SEQUENCE: 302

Glu Gln Ile Ser Gly Ser Leu Val Ala Ala Pro Trp
1               5                   10

<210> SEQ ID NO 303
<211> LENGTH: 12
<212> TYPE: PRT
<213> ORGANISM: artificial sequence
<220> FEATURE:
<223> OTHER INFORMATION: hair binding peptide

<400> SEQUENCE: 303

Leu Asp Thr Ser Phe Pro Pro Val Pro Phe His Ala
1               5                   10

<210> SEQ ID NO 304
<211> LENGTH: 11
<212> TYPE: PRT
<213> ORGANISM: artificial sequence
<220> FEATURE:
<223> OTHER INFORMATION: hair binding peptide

<400> SEQUENCE: 304

Leu Pro Arg Ile Ala Asn Thr Trp Ser Pro Ser
1               5                   10

<210> SEQ ID NO 305
<211> LENGTH: 12
<212> TYPE: PRT
<213> ORGANISM: artificial sequence
<220> FEATURE:
<223> OTHER INFORMATION: hair binding peptide

<400> SEQUENCE: 305

Arg Thr Asn Ala Ala Asp His Pro Ala Ala Val Thr
1               5                   10

<210> SEQ ID NO 306
<211> LENGTH: 12
<212> TYPE: PRT
<213> ORGANISM: artificial sequence
<220> FEATURE:
<223> OTHER INFORMATION: hair binding peptide

<400> SEQUENCE: 306

Ser Leu Asn Trp Val Thr Ile Pro Gly Pro Lys Ile
1               5                   10

<210> SEQ ID NO 307
<211> LENGTH: 12
<212> TYPE: PRT
<213> ORGANISM: artificial sequence
<220> FEATURE:
<223> OTHER INFORMATION: hair binding peptide

<400> SEQUENCE: 307

Thr Asp Met Gln Ala Pro Thr Lys Ser Tyr Ser Asn
1               5                   10

<210> SEQ ID NO 308
<211> LENGTH: 12
<212> TYPE: PRT
```

```
<213> ORGANISM: artificial sequence
<220> FEATURE:
<223> OTHER INFORMATION: hair binding peptide

<400> SEQUENCE: 308

Thr Ile Met Thr Lys Ser Pro Ser Leu Ser Cys Gly
1               5                   10

<210> SEQ ID NO 309
<211> LENGTH: 12
<212> TYPE: PRT
<213> ORGANISM: artificial sequence
<220> FEATURE:
<223> OTHER INFORMATION: hair binding peptide

<400> SEQUENCE: 309

Thr Pro Ala Leu Asp Gly Leu Arg Gln Pro Leu Arg
1               5                   10

<210> SEQ ID NO 310
<211> LENGTH: 12
<212> TYPE: PRT
<213> ORGANISM: artificial sequence
<220> FEATURE:
<223> OTHER INFORMATION: hair binding peptide

<400> SEQUENCE: 310

Thr Tyr Pro Ala Ser Arg Leu Pro Leu Leu Ala Pro
1               5                   10

<210> SEQ ID NO 311
<211> LENGTH: 12
<212> TYPE: PRT
<213> ORGANISM: artificial sequence
<220> FEATURE:
<223> OTHER INFORMATION: hair binding peptide

<400> SEQUENCE: 311

Ala Lys Thr His Lys His Pro Ala Pro Ser Tyr Ser
1               5                   10

<210> SEQ ID NO 312
<211> LENGTH: 12
<212> TYPE: PRT
<213> ORGANISM: artificial sequence
<220> FEATURE:
<223> OTHER INFORMATION: hair binding peptide

<400> SEQUENCE: 312

Thr Asp Pro Thr Pro Phe Ser Ile Ser Pro Glu Arg
1               5                   10

<210> SEQ ID NO 313
<211> LENGTH: 20
<212> TYPE: PRT
<213> ORGANISM: artificial sequence
<220> FEATURE:
<223> OTHER INFORMATION: hair binding peptide

<400> SEQUENCE: 313

Cys Ala Ala Gly Cys Cys Thr Cys Ala Gly Cys Gly Ala Cys Cys Gly
1               5                   10                  15

Ala Ala Thr Ala
            20

<210> SEQ ID NO 314
```

```
<211> LENGTH: 12
<212> TYPE: PRT
<213> ORGANISM: artificial sequence
<220> FEATURE:
<223> OTHER INFORMATION: hair binding peptide

<400> SEQUENCE: 314

Trp His Asp Lys Pro Gln Asn Ser Ser Lys Ser Thr
1               5                   10

<210> SEQ ID NO 315
<211> LENGTH: 12
<212> TYPE: PRT
<213> ORGANISM: artificial sequence
<220> FEATURE:
<223> OTHER INFORMATION: hair binding peptide

<400> SEQUENCE: 315

Asn Glu Val Pro Ala Arg Asn Ala Pro Trp Leu Val
1               5                   10

<210> SEQ ID NO 316
<211> LENGTH: 13
<212> TYPE: PRT
<213> ORGANISM: artificial sequence
<220> FEATURE:
<223> OTHER INFORMATION: hair binding peptide

<400> SEQUENCE: 316

Asn Ser Pro Gly Tyr Gln Ala Asp Ser Val Ala Ile Gly
1               5                   10

<210> SEQ ID NO 317
<211> LENGTH: 12
<212> TYPE: PRT
<213> ORGANISM: artificial sequence
<220> FEATURE:
<223> OTHER INFORMATION: hair binding peptide

<400> SEQUENCE: 317

Thr Gln Asp Ser Ala Gln Lys Ser Pro Ser Pro Leu
1               5                   10

<210> SEQ ID NO 318
<211> LENGTH: 12
<212> TYPE: PRT
<213> ORGANISM: artificial sequence
<220> FEATURE:
<223> OTHER INFORMATION: hair binding peptide

<400> SEQUENCE: 318

Thr Pro Pro Glu Leu Leu His Gly Asp Pro Arg Ser
1               5                   10

<210> SEQ ID NO 319
<211> LENGTH: 12
<212> TYPE: PRT
<213> ORGANISM: artificial sequence
<220> FEATURE:
<223> OTHER INFORMATION: hair binding peptide

<400> SEQUENCE: 319

Thr Pro Pro Thr Asn Val Leu Met Leu Ala Thr Lys
1               5                   10

<210> SEQ ID NO 320
<211> LENGTH: 7
```

```
<212> TYPE: PRT
<213> ORGANISM: artificial sequence
<220> FEATURE:
<223> OTHER INFORMATION: hair binding peptide

<400> SEQUENCE: 320

Asn Thr Ser Gln Leu Ser Thr
1               5

<210> SEQ ID NO 321
<211> LENGTH: 7
<212> TYPE: PRT
<213> ORGANISM: artificial sequence
<220> FEATURE:
<223> OTHER INFORMATION: hair binding peptide

<400> SEQUENCE: 321

Asn Thr Pro Lys Glu Asn Trp
1               5

<210> SEQ ID NO 322
<211> LENGTH: 7
<212> TYPE: PRT
<213> ORGANISM: artificial sequence
<220> FEATURE:
<223> OTHER INFORMATION: hair binding peptide

<400> SEQUENCE: 322

Asn Thr Pro Ala Ser Asn Arg
1               5

<210> SEQ ID NO 323
<211> LENGTH: 7
<212> TYPE: PRT
<213> ORGANISM: artificial sequence
<220> FEATURE:
<223> OTHER INFORMATION: hair binding peptide

<400> SEQUENCE: 323

Pro Arg Gly Met Leu Ser Thr
1               5

<210> SEQ ID NO 324
<211> LENGTH: 7
<212> TYPE: PRT
<213> ORGANISM: artificial sequence
<220> FEATURE:
<223> OTHER INFORMATION: hair binding peptide

<400> SEQUENCE: 324

Pro Pro Thr Tyr Leu Ser Thr
1               5

<210> SEQ ID NO 325
<211> LENGTH: 12
<212> TYPE: PRT
<213> ORGANISM: artificial sequence
<220> FEATURE:
<223> OTHER INFORMATION: hair binding peptide

<400> SEQUENCE: 325

Thr Ile Pro Thr His Arg Gln His Asp Tyr Arg Ser
1               5                   10

<210> SEQ ID NO 326
<211> LENGTH: 7
<212> TYPE: PRT
```

```
<213> ORGANISM: artificial sequence
<220> FEATURE:
<223> OTHER INFORMATION: hair binding peptide

<400> SEQUENCE: 326

Thr Pro Pro Thr His Arg Leu
1               5

<210> SEQ ID NO 327
<211> LENGTH: 7
<212> TYPE: PRT
<213> ORGANISM: artificial sequence
<220> FEATURE:
<223> OTHER INFORMATION: hair binding peptide

<400> SEQUENCE: 327

Leu Pro Thr Met Ser Thr Pro
1               5

<210> SEQ ID NO 328
<211> LENGTH: 7
<212> TYPE: PRT
<213> ORGANISM: artificial sequence
<220> FEATURE:
<223> OTHER INFORMATION: hair binding peptide

<400> SEQUENCE: 328

Leu Gly Thr Asn Ser Thr Pro
1               5

<210> SEQ ID NO 329
<211> LENGTH: 12
<212> TYPE: PRT
<213> ORGANISM: artificial sequence
<220> FEATURE:
<223> OTHER INFORMATION: hair binding peptide

<400> SEQUENCE: 329

Thr Pro Leu Thr Gly Ser Thr Asn Leu Leu Ser Ser
1               5                   10

<210> SEQ ID NO 330
<211> LENGTH: 7
<212> TYPE: PRT
<213> ORGANISM: artificial sequence
<220> FEATURE:
<223> OTHER INFORMATION: hair binding peptide

<400> SEQUENCE: 330

Thr Pro Leu Thr Lys Glu Thr
1               5

<210> SEQ ID NO 331
<211> LENGTH: 7
<212> TYPE: PRT
<213> ORGANISM: artificial sequence
<220> FEATURE:
<223> OTHER INFORMATION: hair binding peptide

<400> SEQUENCE: 331

Gln Gln Ser His Asn Pro Pro
1               5

<210> SEQ ID NO 332
<211> LENGTH: 7
<212> TYPE: PRT
<213> ORGANISM: artificial sequence
```

```
<220> FEATURE:
<223> OTHER INFORMATION: hair binding peptide

<400> SEQUENCE: 332

Thr Gln Pro His Asn Pro Pro
1               5

<210> SEQ ID NO 333
<211> LENGTH: 12
<212> TYPE: PRT
<213> ORGANISM: artificial sequence
<220> FEATURE:
<223> OTHER INFORMATION: hair binding peptide

<400> SEQUENCE: 333

Ser Thr Asn Leu Leu Arg Thr Ser Thr Val His Pro
1               5                   10

<210> SEQ ID NO 334
<211> LENGTH: 12
<212> TYPE: PRT
<213> ORGANISM: artificial sequence
<220> FEATURE:
<223> OTHER INFORMATION: hair binding peptide

<400> SEQUENCE: 334

His Thr Gln Pro Ser Tyr Ser Ser Thr Asn Leu Phe
1               5                   10

<210> SEQ ID NO 335
<211> LENGTH: 7
<212> TYPE: PRT
<213> ORGANISM: artificial sequence
<220> FEATURE:
<223> OTHER INFORMATION: hair binding peptide

<400> SEQUENCE: 335

Ser Leu Leu Ser Ser His Ala
1               5

<210> SEQ ID NO 336
<211> LENGTH: 12
<212> TYPE: PRT
<213> ORGANISM: artificial sequence
<220> FEATURE:
<223> OTHER INFORMATION: hair binding peptide

<400> SEQUENCE: 336

Gln Gln Ser Ser Ile Ser Leu Ser Ser His Ala Val
1               5                   10

<210> SEQ ID NO 337
<211> LENGTH: 7
<212> TYPE: PRT
<213> ORGANISM: artificial sequence
<220> FEATURE:
<223> OTHER INFORMATION: hair binding peptide

<400> SEQUENCE: 337

Asn Ala Ser Pro Ser Ser Leu
1               5

<210> SEQ ID NO 338
<211> LENGTH: 7
<212> TYPE: PRT
<213> ORGANISM: artificial sequence
<220> FEATURE:
```

```
<223> OTHER INFORMATION: hair binding peptide

<400> SEQUENCE: 338

His Ser Pro Ser Ser Leu Arg
1               5

<210> SEQ ID NO 339
<211> LENGTH: 7
<212> TYPE: PRT
<213> ORGANISM: artificial sequence
<220> FEATURE:
<223> OTHER INFORMATION: hair binding peptide
<220> FEATURE:
<221> NAME/KEY: MISC_FEATURE
<222> LOCATION: (2)..(2)
<223> OTHER INFORMATION: Xaa = His, Arg, or Asn

<400> SEQUENCE: 339

Lys Xaa Ser His His Thr His
1               5

<210> SEQ ID NO 340
<211> LENGTH: 7
<212> TYPE: PRT
<213> ORGANISM: artificial sequence
<220> FEATURE:
<223> OTHER INFORMATION: hair binding peptide
<220> FEATURE:
<221> NAME/KEY: MISC_FEATURE
<222> LOCATION: (2)..(2)
<223> OTHER INFORMATION: Xaa = His, Arg, or Asn

<400> SEQUENCE: 340

Glu Xaa Ser His His Thr His
1               5

<210> SEQ ID NO 341
<211> LENGTH: 7
<212> TYPE: PRT
<213> ORGANISM: artificial sequence
<220> FEATURE:
<223> OTHER INFORMATION: hair binding peptide

<400> SEQUENCE: 341

Leu Glu Ser Thr Ser Leu Leu
1               5

<210> SEQ ID NO 342
<211> LENGTH: 7
<212> TYPE: PRT
<213> ORGANISM: artificial sequence
<220> FEATURE:
<223> OTHER INFORMATION: hair binding peptide

<400> SEQUENCE: 342

Thr Pro Leu Thr Lys Glu Thr
1               5

<210> SEQ ID NO 343
<211> LENGTH: 7
<212> TYPE: PRT
<213> ORGANISM: artificial sequence
<220> FEATURE:
<223> OTHER INFORMATION: hair binding peptide

<400> SEQUENCE: 343

Lys Gln Ser His Asn Pro Pro
1               5
```

```
<210> SEQ ID NO 344
<211> LENGTH: 9
<212> TYPE: PRT
<213> ORGANISM: artificial sequence
<220> FEATURE:
<223> OTHER INFORMATION: hair binding peptide

<400> SEQUENCE: 344

Ser Thr Leu His Lys Tyr Lys Ser Gln
1               5

<210> SEQ ID NO 345
<211> LENGTH: 12
<212> TYPE: PRT
<213> ORGANISM: artificial sequence
<220> FEATURE:
<223> OTHER INFORMATION: hair binding peptide

<400> SEQUENCE: 345

Tyr Pro Ser Phe Ser Pro Thr Tyr Arg Pro Ala Phe
1               5                   10

<210> SEQ ID NO 346
<211> LENGTH: 12
<212> TYPE: PRT
<213> ORGANISM: artificial sequence
<220> FEATURE:
<223> OTHER INFORMATION: hair binding peptide

<400> SEQUENCE: 346

Ala Leu Pro Arg Ile Ala Asn Thr Trp Ser Pro Ser
1               5                   10

<210> SEQ ID NO 347
<211> LENGTH: 8
<212> TYPE: PRT
<213> ORGANISM: artificial sequence
<220> FEATURE:
<223> OTHER INFORMATION: hair binding peptide

<400> SEQUENCE: 347

Leu Glu Ser Thr Pro Lys Met Lys
1               5

<210> SEQ ID NO 348
<211> LENGTH: 67
<212> TYPE: PRT
<213> ORGANISM: artificial sequence
<220> FEATURE:
<223> OTHER INFORMATION: hair binding peptide

<400> SEQUENCE: 348

Pro Asn Thr Ser Gln Leu Ser Thr Gly Gly Gly Arg Thr Asn Ala Ala
1               5                   10                  15

Asp His Pro Lys Cys Gly Gly Gly Asn Thr Ser Gln Leu Ser Thr Gly
            20                  25                  30

Gly Gly Arg Thr Asn Ala Ala Asp His Pro Lys Cys Gly Gly Gly Asn
        35                  40                  45

Thr Ser Gln Leu Ser Thr Gly Gly Gly Arg Thr Asn Ala Ala Asp His
    50                  55                  60

Pro Lys Cys
65
```

<210> SEQ ID NO 349
<211> LENGTH: 56
<212> TYPE: PRT
<213> ORGANISM: artificial sequence
<220> FEATURE:
<223> OTHER INFORMATION: hair binding peptide

<400> SEQUENCE: 349

Asp Pro Arg Thr Asn Ala Ala Asp His Pro Ala Ala Val Thr Gly Gly
1               5                   10                  15

Gly Cys Gly Gly Gly Arg Thr Asn Ala Ala Asp His Pro Ala Ala Val
            20                  25                  30

Thr Gly Gly Gly Cys Gly Gly Gly Arg Thr Asn Ala Ala Asp His Pro
        35                  40                  45

Ala Ala Val Thr Gly Gly Gly Cys
    50                  55

<210> SEQ ID NO 350
<211> LENGTH: 51
<212> TYPE: PRT
<213> ORGANISM: artificial sequence
<220> FEATURE:
<223> OTHER INFORMATION: hair binding peptide

<400> SEQUENCE: 350

Asp Pro Arg Thr Asn Ala Ala Asp His Pro Ala Ala Val Thr Gly Gly
1               5                   10                  15

Gly Cys Gly Gly Gly Ile Pro Trp Trp Asn Ile Arg Ala Pro Leu Asn
            20                  25                  30

Ala Gly Gly Gly Cys Gly Gly Gly Asp Leu Thr Leu Pro Phe His Gly
        35                  40                  45

Gly Gly Cys
    50

<210> SEQ ID NO 351
<211> LENGTH: 58
<212> TYPE: PRT
<213> ORGANISM: artificial sequence
<220> FEATURE:
<223> OTHER INFORMATION: hair binding peptide

<400> SEQUENCE: 351

Arg Thr Asn Ala Ala Asp His Pro Ala Ala Val Thr Gly Gly Gly Cys
1               5                   10                  15

Asp Pro Gly Gly Gly Arg Thr Asn Ala Ala Asp His Pro Ala Ala Val
            20                  25                  30

Thr Gly Gly Gly Cys Asp Pro Gly Gly Gly Arg Thr Asn Ala Ala Asp
        35                  40                  45

His Pro Ala Ala Val Thr Gly Gly Gly Cys
    50                  55

<210> SEQ ID NO 352
<211> LENGTH: 83
<212> TYPE: PRT
<213> ORGANISM: artificial sequence
<220> FEATURE:
<223> OTHER INFORMATION: hair binding peptide

<400> SEQUENCE: 352

Asp Pro Thr Pro Pro Thr Asn Val Leu Met Leu Ala Thr Lys Gly Gly
1               5                   10                  15

Gly Arg Thr Asn Ala Ala Asp His Pro Lys Cys Gly Gly Gly Thr Pro

-continued

```
            20                  25                  30

Pro Thr Asn Val Leu Met Leu Ala Thr Lys Gly Gly Gly Arg Thr Asn
        35                  40                  45

Ala Ala Asp His Pro Lys Cys Gly Gly Gly Thr Pro Pro Thr Asn Val
    50                  55                  60

Leu Met Leu Ala Thr Lys Gly Gly Gly Arg Thr Asn Ala Ala Asp His
65                  70                  75                  80

Pro Lys Cys

<210> SEQ ID NO 353
<211> LENGTH: 83
<212> TYPE: PRT
<213> ORGANISM: artificial sequence
<220> FEATURE:
<223> OTHER INFORMATION: hair binding peptide

<400> SEQUENCE: 353

Asp Pro Arg Thr Asn Ala Ala Asp His Pro Gly Gly Gly Thr Pro Pro
1               5                   10                  15

Thr Asn Val Leu Met Leu Ala Thr Lys Lys Cys Gly Gly Gly Arg Thr
            20                  25                  30

Asn Ala Ala Asp His Pro Gly Gly Gly Thr Pro Pro Thr Asn Val Leu
        35                  40                  45

Met Leu Ala Thr Lys Lys Cys Gly Gly Gly Arg Thr Asn Ala Ala Asp
    50                  55                  60

His Pro Gly Gly Gly Thr Pro Pro Thr Asn Val Leu Met Leu Ala Thr
65                  70                  75                  80

Lys Lys Cys

<210> SEQ ID NO 354
<211> LENGTH: 12
<212> TYPE: PRT
<213> ORGANISM: artificial sequence
<220> FEATURE:
<223> OTHER INFORMATION: Nail binding peptide

<400> SEQUENCE: 354

Ala Leu Pro Arg Ile Ala Asn Thr Trp Ser Pro Ser
1               5                   10

<210> SEQ ID NO 355
<211> LENGTH: 12
<212> TYPE: PRT
<213> ORGANISM: artificial sequence
<220> FEATURE:
<223> OTHER INFORMATION: Nail binding peptide

<400> SEQUENCE: 355

Tyr Pro Ser Phe Ser Pro Thr Tyr Arg Pro Ala Phe
1               5                   10

<210> SEQ ID NO 356
<211> LENGTH: 17
<212> TYPE: PRT
<213> ORGANISM: artificial sequence
<220> FEATURE:
<223> OTHER INFORMATION: antimicrobial peptide

<400> SEQUENCE: 356

Pro Lys Gly Leu Lys Lys Leu Leu Lys Gly Leu Lys Lys Leu Leu Lys
1               5                   10                  15
```

Leu

<210> SEQ ID NO 357
<211> LENGTH: 16
<212> TYPE: PRT
<213> ORGANISM: artificial sequence
<220> FEATURE:
<223> OTHER INFORMATION: antimicrobial peptide

<400> SEQUENCE: 357

Lys Gly Leu Lys Lys Leu Leu Lys Gly Leu Lys Lys Leu Leu Lys Leu
1               5                   10                  15

<210> SEQ ID NO 358
<211> LENGTH: 16
<212> TYPE: PRT
<213> ORGANISM: artificial sequence
<220> FEATURE:
<223> OTHER INFORMATION: antimicrobial peptide

<400> SEQUENCE: 358

Lys Gly Leu Lys Lys Leu Leu Lys Leu Leu Lys Lys Leu Leu Lys Leu
1               5                   10                  15

<210> SEQ ID NO 359
<211> LENGTH: 14
<212> TYPE: PRT
<213> ORGANISM: artificial sequence
<220> FEATURE:
<223> OTHER INFORMATION: antimicrobial peptide

<400> SEQUENCE: 359

Leu Lys Lys Leu Leu Lys Leu Leu Lys Lys Leu Leu Lys Leu
1               5                   10

<210> SEQ ID NO 360
<211> LENGTH: 12
<212> TYPE: PRT
<213> ORGANISM: artificial sequence
<220> FEATURE:
<223> OTHER INFORMATION: antimicrobial peptide

<400> SEQUENCE: 360

Leu Lys Lys Leu Leu Lys Leu Leu Lys Lys Leu Leu
1               5                   10

<210> SEQ ID NO 361
<211> LENGTH: 17
<212> TYPE: PRT
<213> ORGANISM: artificial sequence
<220> FEATURE:
<223> OTHER INFORMATION: antimicrobial peptide

<400> SEQUENCE: 361

Val Ala Lys Lys Leu Ala Lys Leu Ala Lys Lys Leu Ala Lys Leu Ala
1               5                   10                  15

Leu

<210> SEQ ID NO 362
<211> LENGTH: 13
<212> TYPE: PRT
<213> ORGANISM: artificial sequence
<220> FEATURE:
<223> OTHER INFORMATION: antimicrobial peptide

<400> SEQUENCE: 362

```
Phe Ala Lys Leu Leu Ala Lys Ala Leu Lys Lys Leu Leu
1               5                   10
```

<210> SEQ ID NO 363
<211> LENGTH: 16
<212> TYPE: PRT
<213> ORGANISM: artificial sequence
<220> FEATURE:
<223> OTHER INFORMATION: antimicrobial peptide

<400> SEQUENCE: 363

```
Lys Gly Leu Lys Lys Gly Leu Lys Leu Leu Lys Leu Leu Lys Leu
1               5                   10                  15
```

<210> SEQ ID NO 364
<211> LENGTH: 16
<212> TYPE: PRT
<213> ORGANISM: artificial sequence
<220> FEATURE:
<223> OTHER INFORMATION: antimicrobial peptide

<400> SEQUENCE: 364

```
Lys Gly Leu Lys Lys Leu Leu Lys Leu Gly Lys Lys Leu Leu Lys Leu
1               5                   10                  15
```

<210> SEQ ID NO 365
<211> LENGTH: 16
<212> TYPE: PRT
<213> ORGANISM: artificial sequence
<220> FEATURE:
<223> OTHER INFORMATION: antimicrobial peptide

<400> SEQUENCE: 365

```
Lys Gly Leu Lys Lys Leu Gly Lys Leu Leu Lys Lys Leu Leu Lys Leu
1               5                   10                  15
```

<210> SEQ ID NO 366
<211> LENGTH: 16
<212> TYPE: PRT
<213> ORGANISM: artificial sequence
<220> FEATURE:
<223> OTHER INFORMATION: antimicrobial peptide

<400> SEQUENCE: 366

```
Lys Gly Leu Lys Lys Leu Leu Lys Leu Leu Lys Lys Gly Leu Lys Leu
1               5                   10                  15
```

<210> SEQ ID NO 367
<211> LENGTH: 16
<212> TYPE: PRT
<213> ORGANISM: artificial sequence
<220> FEATURE:
<223> OTHER INFORMATION: antimicrobial peptide

<400> SEQUENCE: 367

```
Lys Gly Leu Lys Lys Leu Leu Lys Leu Leu Lys Lys Leu Gly Lys Leu
1               5                   10                  15
```

<210> SEQ ID NO 368
<211> LENGTH: 19
<212> TYPE: PRT
<213> ORGANISM: artificial sequence
<220> FEATURE:
<223> OTHER INFORMATION: antimicrobial peptide

<400> SEQUENCE: 368

```
Phe Ala Leu Ala Leu Lys Ala Leu Lys Lys Leu Lys Lys Ala Leu Lys
```

```
1               5                  10                  15
Lys Ala Leu

<210> SEQ ID NO 369
<211> LENGTH: 17
<212> TYPE: PRT
<213> ORGANISM: artificial sequence
<220> FEATURE:
<223> OTHER INFORMATION: antimicrobial peptide

<400> SEQUENCE: 369

Phe Ala Lys Lys Leu Ala Lys Leu Ala Lys Lys Leu Ala Lys Leu Ala
1               5                  10                  15

Leu

<210> SEQ ID NO 370
<211> LENGTH: 13
<212> TYPE: PRT
<213> ORGANISM: artificial sequence
<220> FEATURE:
<223> OTHER INFORMATION: antimicrobial peptide

<400> SEQUENCE: 370

Phe Ala Lys Leu Leu Ala Lys Leu Ala Lys Lys Leu Leu
1               5                  10

<210> SEQ ID NO 371
<211> LENGTH: 15
<212> TYPE: PRT
<213> ORGANISM: artificial sequence
<220> FEATURE:
<223> OTHER INFORMATION: antimicrobial peptide

<400> SEQUENCE: 371

Phe Ala Lys Lys Leu Ala Lys Leu Ala Leu Lys Leu Ala Lys Leu
1               5                  10                  15

<210> SEQ ID NO 372
<211> LENGTH: 10
<212> TYPE: PRT
<213> ORGANISM: artificial sequence
<220> FEATURE:
<223> OTHER INFORMATION: antimicrobial peptide

<400> SEQUENCE: 372

Phe Ala Lys Lys Leu Ala Lys Lys Leu Leu
1               5                  10

<210> SEQ ID NO 373
<211> LENGTH: 13
<212> TYPE: PRT
<213> ORGANISM: artificial sequence
<220> FEATURE:
<223> OTHER INFORMATION: antimicrobial peptide

<400> SEQUENCE: 373

Phe Ala Lys Leu Leu Ala Lys Leu Ala Lys Lys Val Leu
1               5                  10

<210> SEQ ID NO 374
<211> LENGTH: 13
<212> TYPE: PRT
<213> ORGANISM: artificial sequence
<220> FEATURE:
<223> OTHER INFORMATION: antimicrobial peptide
```

```
<400> SEQUENCE: 374

Lys Tyr Lys Lys Ala Leu Lys Lys Leu Ala Lys Leu Leu
1               5                   10

<210> SEQ ID NO 375
<211> LENGTH: 12
<212> TYPE: PRT
<213> ORGANISM: artificial sequence
<220> FEATURE:
<223> OTHER INFORMATION: antimicrobial peptide

<400> SEQUENCE: 375

Phe Ala Leu Leu Lys Ala Leu Leu Lys Lys Ala Leu
1               5                   10

<210> SEQ ID NO 376
<211> LENGTH: 14
<212> TYPE: PRT
<213> ORGANISM: artificial sequence
<220> FEATURE:
<223> OTHER INFORMATION: antimicrobial peptide

<400> SEQUENCE: 376

Lys Arg Leu Phe Lys Lys Leu Lys Phe Ser Leu Arg Lys Tyr
1               5                   10

<210> SEQ ID NO 377
<211> LENGTH: 14
<212> TYPE: PRT
<213> ORGANISM: artificial sequence
<220> FEATURE:
<223> OTHER INFORMATION: antimicrobial peptide

<400> SEQUENCE: 377

Lys Arg Leu Phe Lys Lys Leu Leu Phe Ser Leu Arg Lys Tyr
1               5                   10

<210> SEQ ID NO 378
<211> LENGTH: 14
<212> TYPE: PRT
<213> ORGANISM: artificial sequence
<220> FEATURE:
<223> OTHER INFORMATION: antimicrobial peptide

<400> SEQUENCE: 378

Leu Leu Leu Phe Leu Leu Lys Lys Arg Lys Lys Arg Lys Tyr
1               5                   10

<210> SEQ ID NO 379
<211> LENGTH: 36
<212> TYPE: PRT
<213> ORGANISM: Hyalophora cecropia

<400> SEQUENCE: 379

Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Trp Gly Gln Ala Thr
                20                  25                  30

Gln Ile Ala Lys
        35

<210> SEQ ID NO 380
<211> LENGTH: 23
<212> TYPE: PRT
<213> ORGANISM: Xenopus sp.
```

```
<400> SEQUENCE: 380

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 381
<211> LENGTH: 22
<212> TYPE: PRT
<213> ORGANISM: Xenopus sp.

<400> SEQUENCE: 381

Gly Ile Gly Lys Phe Leu Lys Lys Ala Lys Lys Phe Gly Lys Ala Phe
1               5                   10                  15

Val Lys Ile Leu Lys Lys
            20

<210> SEQ ID NO 382
<211> LENGTH: 12
<212> TYPE: PRT
<213> ORGANISM: Bos Taurus

<400> SEQUENCE: 382

Arg Leu Cys Arg Ile Val Val Ile Arg Val Cys Arg
1               5                   10

<210> SEQ ID NO 383
<211> LENGTH: 13
<212> TYPE: PRT
<213> ORGANISM: Bos sp.

<400> SEQUENCE: 383

Ile Leu Pro Trp Lys Trp Pro Trp Trp Pro Trp Arg Arg
1               5                   10

<210> SEQ ID NO 384
<211> LENGTH: 24
<212> TYPE: PRT
<213> ORGANISM: Homo sapiens

<400> SEQUENCE: 384

Asp Ser His Ala Lys Arg His His Gly Tyr Lys Arg Lys Phe His Glu
1               5                   10                  15

Lys His His Ser His Arg Gly Tyr
            20

<210> SEQ ID NO 385
<211> LENGTH: 7
<212> TYPE: PRT
<213> ORGANISM: artificial sequence
<220> FEATURE:
<223> OTHER INFORMATION: pigment binding peptide

<400> SEQUENCE: 385

Met Pro Pro Pro Leu Met Gln
1               5

<210> SEQ ID NO 386
<211> LENGTH: 7
<212> TYPE: PRT
<213> ORGANISM: artificial sequence
<220> FEATURE:
<223> OTHER INFORMATION: pigment binding peptide
```

-continued

```
<400> SEQUENCE: 386

Phe His Glu Asn Trp Pro Ser
1               5

<210> SEQ ID NO 387
<211> LENGTH: 12
<212> TYPE: PRT
<213> ORGANISM: artificial sequence
<220> FEATURE:
<223> OTHER INFORMATION: pigment binding peptide

<400> SEQUENCE: 387

Arg Thr Ala Pro Thr Thr Pro Leu Leu Leu Ser Leu
1               5                   10

<210> SEQ ID NO 388
<211> LENGTH: 12
<212> TYPE: PRT
<213> ORGANISM: artificial sequence
<220> FEATURE:
<223> OTHER INFORMATION: pigment binding peptide

<400> SEQUENCE: 388

Trp His Leu Ser Trp Ser Pro Val Pro Leu Pro Thr
1               5                   10

<210> SEQ ID NO 389
<211> LENGTH: 7
<212> TYPE: PRT
<213> ORGANISM: artificial sequence
<220> FEATURE:
<223> OTHER INFORMATION: pigment binding peptide

<400> SEQUENCE: 389

Pro His Ala Arg Leu Val Gly
1               5

<210> SEQ ID NO 390
<211> LENGTH: 7
<212> TYPE: PRT
<213> ORGANISM: artificial sequence
<220> FEATURE:
<223> OTHER INFORMATION: pigment binding peptide

<400> SEQUENCE: 390

Asn Ile Pro Tyr His His Pro
1               5

<210> SEQ ID NO 391
<211> LENGTH: 7
<212> TYPE: PRT
<213> ORGANISM: artificial sequence
<220> FEATURE:
<223> OTHER INFORMATION: pigment binding peptide

<400> SEQUENCE: 391

Thr Thr Met Pro Ala Ile Pro
1               5

<210> SEQ ID NO 392
<211> LENGTH: 7
<212> TYPE: PRT
<213> ORGANISM: artificial sequence
<220> FEATURE:
<223> OTHER INFORMATION: pigment binding peptide
```

```
<400> SEQUENCE: 392

His Asn Leu Pro Pro Arg Ser
1               5

<210> SEQ ID NO 393
<211> LENGTH: 12
<212> TYPE: PRT
<213> ORGANISM: artificial sequence
<220> FEATURE:
<223> OTHER INFORMATION: pigment binding peptide

<400> SEQUENCE: 393

Ala His Lys Thr Gln Met Gly Val Arg Gln Pro Ala
1               5                   10

<210> SEQ ID NO 394
<211> LENGTH: 12
<212> TYPE: PRT
<213> ORGANISM: artificial sequence
<220> FEATURE:
<223> OTHER INFORMATION: pigment binding peptide

<400> SEQUENCE: 394

Ala Asp Asn Val Gln Met Gly Val Ser His Thr Pro
1               5                   10

<210> SEQ ID NO 395
<211> LENGTH: 12
<212> TYPE: PRT
<213> ORGANISM: artificial sequence
<220> FEATURE:
<223> OTHER INFORMATION: pigment binding peptide

<400> SEQUENCE: 395

Ala His Asn Ala Gln Met Gly Val Ser His Pro Pro
1               5                   10

<210> SEQ ID NO 396
<211> LENGTH: 12
<212> TYPE: PRT
<213> ORGANISM: artificial sequence
<220> FEATURE:
<223> OTHER INFORMATION: pigment binding peptide

<400> SEQUENCE: 396

Ala Asp Tyr Val Gly Met Gly Val Ser His Arg Pro
1               5                   10

<210> SEQ ID NO 397
<211> LENGTH: 12
<212> TYPE: PRT
<213> ORGANISM: artificial sequence
<220> FEATURE:
<223> OTHER INFORMATION: pigment binding peptide

<400> SEQUENCE: 397

Ser Val Ser Val Gly Met Lys Pro Ser Pro Arg Pro
1               5                   10

<210> SEQ ID NO 398
<211> LENGTH: 7
<212> TYPE: PRT
<213> ORGANISM: artificial sequence
<220> FEATURE:
<223> OTHER INFORMATION: pigment binding peptide

<400> SEQUENCE: 398
```

```
Tyr Pro Asn Thr Ala Leu Val
1               5

<210> SEQ ID NO 399
<211> LENGTH: 7
<212> TYPE: PRT
<213> ORGANISM: artificial sequence
<220> FEATURE:
<223> OTHER INFORMATION: pigment binding peptide

<400> SEQUENCE: 399

Val Ala Thr Arg Ile Val Ser
1               5

<210> SEQ ID NO 400
<211> LENGTH: 12
<212> TYPE: PRT
<213> ORGANISM: artificial sequence
<220> FEATURE:
<223> OTHER INFORMATION: pigment binding peptide

<400> SEQUENCE: 400

His Ser Leu Lys Asn Ser Met Leu Thr Val Met Ala
1               5                   10

<210> SEQ ID NO 401
<211> LENGTH: 7
<212> TYPE: PRT
<213> ORGANISM: artificial sequence
<220> FEATURE:
<223> OTHER INFORMATION: pigment binding peptide

<400> SEQUENCE: 401

Asn Tyr Pro Thr Gln Ala Pro
1               5

<210> SEQ ID NO 402
<211> LENGTH: 7
<212> TYPE: PRT
<213> ORGANISM: artificial sequence
<220> FEATURE:
<223> OTHER INFORMATION: pigment binding peptide

<400> SEQUENCE: 402

Lys Cys Cys Tyr Ser Val Gly
1               5

<210> SEQ ID NO 403
<211> LENGTH: 12
<212> TYPE: PRT
<213> ORGANISM: artificial sequence
<220> FEATURE:
<223> OTHER INFORMATION: pigment binding peptide

<400> SEQUENCE: 403

Arg His Asp Leu Asn Thr Trp Leu Pro Pro Val Lys
1               5                   10

<210> SEQ ID NO 404
<211> LENGTH: 12
<212> TYPE: PRT
<213> ORGANISM: artificial sequence
<220> FEATURE:
<223> OTHER INFORMATION: pigment binding peptide

<400> SEQUENCE: 404
```

```
Glu Ile Ser Leu Pro Ala Lys Leu Pro Ser Ala Ser
1               5                   10
```

```
<210> SEQ ID NO 405
<211> LENGTH: 12
<212> TYPE: PRT
<213> ORGANISM: artificial sequence
<220> FEATURE:
<223> OTHER INFORMATION: pigment binding peptide

<400> SEQUENCE: 405

Ser Val Ser Val Gly Met Lys Pro Ser Pro Arg Pro
1               5                   10
```

```
<210> SEQ ID NO 406
<211> LENGTH: 12
<212> TYPE: PRT
<213> ORGANISM: artificial sequence
<220> FEATURE:
<223> OTHER INFORMATION: pigment binding peptide

<400> SEQUENCE: 406

Ser Asp Tyr Val Gly Met Arg Pro Ser Pro Arg His
1               5                   10
```

```
<210> SEQ ID NO 407
<211> LENGTH: 12
<212> TYPE: PRT
<213> ORGANISM: artificial sequence
<220> FEATURE:
<223> OTHER INFORMATION: pigment binding peptide

<400> SEQUENCE: 407

Ser Asp Tyr Val Gly Met Arg Leu Ser Pro Ser Gln
1               5                   10
```

```
<210> SEQ ID NO 408
<211> LENGTH: 12
<212> TYPE: PRT
<213> ORGANISM: artificial sequence
<220> FEATURE:
<223> OTHER INFORMATION: pigment binding peptide

<400> SEQUENCE: 408

Ser Val Ser Val Gly Ile Gln Pro Ser Pro Arg Pro
1               5                   10
```

```
<210> SEQ ID NO 409
<211> LENGTH: 12
<212> TYPE: PRT
<213> ORGANISM: artificial sequence
<220> FEATURE:
<223> OTHER INFORMATION: pigment binding peptide

<400> SEQUENCE: 409

Tyr Val Ser Val Gly Ile Lys Pro Ser Pro Arg Pro
1               5                   10
```

```
<210> SEQ ID NO 410
<211> LENGTH: 12
<212> TYPE: PRT
<213> ORGANISM: artificial sequence
<220> FEATURE:
<223> OTHER INFORMATION: pigment binding peptide

<400> SEQUENCE: 410

Tyr Val Cys Glu Gly Ile His Pro Cys Pro Arg Pro
```

-continued

```
<210> SEQ ID NO 411
<211> LENGTH: 7
<212> TYPE: PRT
<213> ORGANISM: artificial sequence
<220> FEATURE:
<223> OTHER INFORMATION: cellulose binding peptide

<400> SEQUENCE: 411

Val Pro Arg Val Thr Ser Ile
1               5

<210> SEQ ID NO 412
<211> LENGTH: 7
<212> TYPE: PRT
<213> ORGANISM: artificial sequence
<220> FEATURE:
<223> OTHER INFORMATION: cellulose binding peptide

<400> SEQUENCE: 412

Met Ala Asn His Asn Leu Ser
1               5

<210> SEQ ID NO 413
<211> LENGTH: 7
<212> TYPE: PRT
<213> ORGANISM: artificial sequence
<220> FEATURE:
<223> OTHER INFORMATION: cellulose binding peptide

<400> SEQUENCE: 413

Phe His Glu Asn Trp Pro Ser
1               5

<210> SEQ ID NO 414
<211> LENGTH: 12
<212> TYPE: PRT
<213> ORGANISM: artificial sequence
<220> FEATURE:
<223> OTHER INFORMATION: cellulose binding peptide

<400> SEQUENCE: 414

Thr His Lys Thr Ser Thr Gln Arg Leu Leu Ala Ala
1               5                   10

<210> SEQ ID NO 415
<211> LENGTH: 12
<212> TYPE: PRT
<213> ORGANISM: artificial sequence
<220> FEATURE:
<223> OTHER INFORMATION: cellulose binding peptide

<400> SEQUENCE: 415

Lys Cys Cys Tyr Val Asn Val Gly Ser Val Phe Ser
1               5                   10

<210> SEQ ID NO 416
<211> LENGTH: 12
<212> TYPE: PRT
<213> ORGANISM: artificial sequence
<220> FEATURE:
<223> OTHER INFORMATION: cellulose binding peptide

<400> SEQUENCE: 416

Ala His Met Gln Phe Arg Thr Ser Leu Thr Pro His
1               5                   10
```

<210> SEQ ID NO 417
<211> LENGTH: 12
<212> TYPE: PRT
<213> ORGANISM: artificial sequence
<220> FEATURE:
<223> OTHER INFORMATION: PET binding peptide

<400> SEQUENCE: 417

Gly Thr Ser Asp His Met Ile Met Pro Phe Phe Asn
1               5                   10

<210> SEQ ID NO 418
<211> LENGTH: 12
<212> TYPE: PRT
<213> ORGANISM: artificial sequence
<220> FEATURE:
<223> OTHER INFORMATION: PMMA binding peptide

<400> SEQUENCE: 418

Ile Pro Trp Trp Asn Ile Arg Ala Pro Leu Asn Ala
1               5                   10

<210> SEQ ID NO 419
<211> LENGTH: 12
<212> TYPE: PRT
<213> ORGANISM: artificial sequence
<220> FEATURE:
<223> OTHER INFORMATION: PMMA binding peptide

<400> SEQUENCE: 419

Thr Ala Val Met Asn Val Val Asn Asn Gln Leu Ser
1               5                   10

<210> SEQ ID NO 420
<211> LENGTH: 12
<212> TYPE: PRT
<213> ORGANISM: artificial sequence
<220> FEATURE:
<223> OTHER INFORMATION: PMMA binding peptide

<400> SEQUENCE: 420

Val Pro Trp Trp Ala Pro Ser Lys Leu Ser Met Gln
1               5                   10

<210> SEQ ID NO 421
<211> LENGTH: 12
<212> TYPE: PRT
<213> ORGANISM: artificial sequence
<220> FEATURE:
<223> OTHER INFORMATION: PMMA binding peptide

<400> SEQUENCE: 421

Met Val Met Ala Pro His Thr Pro Arg Ala Arg Ser
1               5                   10

<210> SEQ ID NO 422
<211> LENGTH: 12
<212> TYPE: PRT
<213> ORGANISM: artificial sequence
<220> FEATURE:
<223> OTHER INFORMATION: PMMA binding peptide

<400> SEQUENCE: 422

Thr Tyr Pro Asn Trp Ala His Leu Leu Ser His Tyr
1               5                   10

```
<210> SEQ ID NO 423
<211> LENGTH: 7
<212> TYPE: PRT
<213> ORGANISM: artificial sequence
<220> FEATURE:
<223> OTHER INFORMATION: PMMA binding peptide

<400> SEQUENCE: 423

Thr Pro Trp Trp Arg Ile Thr
1               5

<210> SEQ ID NO 424
<211> LENGTH: 7
<212> TYPE: PRT
<213> ORGANISM: artificial sequence
<220> FEATURE:
<223> OTHER INFORMATION: PMMA binding peptide

<400> SEQUENCE: 424

Asp Leu Thr Leu Pro Phe His
1               5

<210> SEQ ID NO 425
<211> LENGTH: 7
<212> TYPE: PRT
<213> ORGANISM: artificial sequence
<220> FEATURE:
<223> OTHER INFORMATION: PMMA binding peptide

<400> SEQUENCE: 425

Gly Thr Ser Ile Pro Ala Met
1               5

<210> SEQ ID NO 426
<211> LENGTH: 7
<212> TYPE: PRT
<213> ORGANISM: artificial sequence
<220> FEATURE:
<223> OTHER INFORMATION: PMMA binding peptide

<400> SEQUENCE: 426

His His Lys His Val Val Ala
1               5

<210> SEQ ID NO 427
<211> LENGTH: 7
<212> TYPE: PRT
<213> ORGANISM: artificial sequence
<220> FEATURE:
<223> OTHER INFORMATION: PMMA binding peptide

<400> SEQUENCE: 427

His His His Lys His Phe Met
1               5

<210> SEQ ID NO 428
<211> LENGTH: 7
<212> TYPE: PRT
<213> ORGANISM: artificial sequence
<220> FEATURE:
<223> OTHER INFORMATION: PMMA binding peptide

<400> SEQUENCE: 428

His His His Arg His Gln Gly
1               5
```

```
<210> SEQ ID NO 429
<211> LENGTH: 7
<212> TYPE: PRT
<213> ORGANISM: artificial sequence
<220> FEATURE:
<223> OTHER INFORMATION: PMMA binding peptide

<400> SEQUENCE: 429

His His Trp His Ala Pro Arg
1               5

<210> SEQ ID NO 430
<211> LENGTH: 7
<212> TYPE: PRT
<213> ORGANISM: artificial sequence
<220> FEATURE:
<223> OTHER INFORMATION: Nylon binding peptide

<400> SEQUENCE: 430

Lys Thr Pro Pro Thr Arg Pro
1               5

<210> SEQ ID NO 431
<211> LENGTH: 7
<212> TYPE: PRT
<213> ORGANISM: artificial sequence
<220> FEATURE:
<223> OTHER INFORMATION: Nylon binding peptide

<400> SEQUENCE: 431

Val Ile Asn Pro Asn Leu Asp
1               5

<210> SEQ ID NO 432
<211> LENGTH: 7
<212> TYPE: PRT
<213> ORGANISM: artificial sequence
<220> FEATURE:
<223> OTHER INFORMATION: Nylon binding peptide

<400> SEQUENCE: 432

Lys Val Trp Ile Val Ser Thr
1               5

<210> SEQ ID NO 433
<211> LENGTH: 7
<212> TYPE: PRT
<213> ORGANISM: artificial sequence
<220> FEATURE:
<223> OTHER INFORMATION: Nylon binding peptide

<400> SEQUENCE: 433

Ala Glu Pro Val Ala Met Leu
1               5

<210> SEQ ID NO 434
<211> LENGTH: 7
<212> TYPE: PRT
<213> ORGANISM: artificial sequence
<220> FEATURE:
<223> OTHER INFORMATION: Nylon binding peptide

<400> SEQUENCE: 434

Ala Glu Leu Val Ala Met Leu
1               5

<210> SEQ ID NO 435
```

```
<211> LENGTH: 7
<212> TYPE: PRT
<213> ORGANISM: artificial sequence
<220> FEATURE:
<223> OTHER INFORMATION: Nylon binding peptide

<400> SEQUENCE: 435

His Ser Leu Arg Leu Asp Trp
1               5

<210> SEQ ID NO 436
<211> LENGTH: 12
<212> TYPE: PRT
<213> ORGANISM: artificial sequence
<220> FEATURE:
<223> OTHER INFORMATION: PTFE binding peptide

<400> SEQUENCE: 436

Glu Ser Ser Tyr Ser Trp Ser Pro Ala Arg Leu Ser
1               5                   10

<210> SEQ ID NO 437
<211> LENGTH: 12
<212> TYPE: PRT
<213> ORGANISM: artificial sequence
<220> FEATURE:
<223> OTHER INFORMATION: PTFE binding peptide

<400> SEQUENCE: 437

Gly Pro Leu Lys Leu Leu His Ala Trp Trp Gln Pro
1               5                   10

<210> SEQ ID NO 438
<211> LENGTH: 7
<212> TYPE: PRT
<213> ORGANISM: artificial sequence
<220> FEATURE:
<223> OTHER INFORMATION: PTFE binding peptide

<400> SEQUENCE: 438

Asn Ala Leu Thr Arg Pro Val
1               5

<210> SEQ ID NO 439
<211> LENGTH: 7
<212> TYPE: PRT
<213> ORGANISM: artificial sequence
<220> FEATURE:
<223> OTHER INFORMATION: PTFE binding peptide

<400> SEQUENCE: 439

Ser Ala Pro Ser Ser Lys Asn
1               5

<210> SEQ ID NO 440
<211> LENGTH: 12
<212> TYPE: PRT
<213> ORGANISM: artificial sequence
<220> FEATURE:
<223> OTHER INFORMATION: PTFE binding peptide

<400> SEQUENCE: 440

Ser Val Ser Val Gly Met Lys Pro Ser Pro Arg Pro
1               5                   10

<210> SEQ ID NO 441
<211> LENGTH: 12
```

```
<212> TYPE: PRT
<213> ORGANISM: artificial sequence
<220> FEATURE:
<223> OTHER INFORMATION: PTFE binding peptide

<400> SEQUENCE: 441

Ser Tyr Tyr Ser Leu Pro Pro Ile Phe His Ile Pro
1               5                   10

<210> SEQ ID NO 442
<211> LENGTH: 12
<212> TYPE: PRT
<213> ORGANISM: artificial sequence
<220> FEATURE:
<223> OTHER INFORMATION: PTFE binding peptide

<400> SEQUENCE: 442

Thr Phe Thr Pro Tyr Ser Ile Thr His Ala Leu Leu
1               5                   10

<210> SEQ ID NO 443
<211> LENGTH: 12
<212> TYPE: PRT
<213> ORGANISM: artificial sequence
<220> FEATURE:
<223> OTHER INFORMATION: PTFE binding peptide

<400> SEQUENCE: 443

Thr Met Gly Phe Thr Ala Pro Arg Phe Pro His Tyr
1               5                   10

<210> SEQ ID NO 444
<211> LENGTH: 12
<212> TYPE: PRT
<213> ORGANISM: artificial sequence
<220> FEATURE:
<223> OTHER INFORMATION: PTFE binding peptide

<400> SEQUENCE: 444

Thr Asn Pro Phe Pro Pro Pro Pro Ser Ser Pro Ala
1               5                   10

<210> SEQ ID NO 445
<211> LENGTH: 5
<212> TYPE: PRT
<213> ORGANISM: artificial sequence
<220> FEATURE:
<223> OTHER INFORMATION: Caspase-3 cleavage sequence
<220> FEATURE:
<221> NAME/KEY: MISC_FEATURE
<222> LOCATION: (5)..(5)
<223> OTHER INFORMATION: Xaa = any naturally occurring amino acid except
      Pro, Glu, Asp, Gln, Lys, or Arg.

<400> SEQUENCE: 445

Asp Met Gln Asp Xaa
1               5
```

ZEIN-BASED PEPTIDE TAGS FOR THE EXPRESSION AND PURIFICATION OF BIOACTIVE PEPTIDES

CROSS-REFERENCE TO RELATED APPLICATION

This application claims priority under 35 U.S.C.§119 from U.S. Provisional Application Ser. No. 60/852,838, filed Oct. 19, 2006.

FIELD OF THE INVENTION

The invention relates to the field of protein expression and purification from microbial cells. More specifically, a family of peptide tags has been discovered that are useful in the generation of insoluble fusion proteins.

BACKGROUND OF THE INVENTION

The efficient production of bioactive proteins and peptides has become a hallmark of the biomedical and industrial biochemical industry. Bioactive peptides and proteins are used as curative agents in a variety of diseases such as diabetes (insulin), viral infections and leukemia (interferon), diseases of the immune system (interleukins), and red blood cell deficiencies (erythropoietin) to name a few. Additionally, large quantities of proteins and peptides are needed for various industrial applications including, for example, the pulp and paper and pulp industries, textiles, food industries, sugar refining, wastewater treatment, production of alcoholic beverages and as catalysts for the generation of new pharmaceuticals.

With the advent of the discovery and implementation of combinatorial peptide screening technologies such as bacterial display (Kemp, D. J.; Proc. Natl. Acad. Sci. USA 78(7): 4520-4524 (1981); yeast display (Chien et al., Proc Natl Acad Sci USA 88(21): 9578-82 (1991)), combinatorial solid phase peptide synthesis (U.S. Pat. No. 5,449,754, U.S. Pat. No. 5,480,971, U.S. Pat. No. 5,585,275, U.S. Pat. No. 5,639,603), and phage display technology (U.S. Pat. No. 5,223,409, U.S. Pat. No. 5,403,484, U.S. Pat. No. 5,571,698, U.S. Pat. No. 5,837,500) new applications for peptides having specific binding affinities have been developed. In particular, peptides are being looked to as linkers in biomedical fields for the attachment of diagnostic and pharmaceutical agents to surfaces (see Grinstaff et al, U.S. Patent Application Publication No. 2003/0185870 and Linter in U.S. Pat. No. 6,620,419), as well as in the personal care industry for the attachment of benefit agents to body surfaces such as hair and skin (see commonly owned U.S. patent application Ser. No. 10/935, 642, and Janssen et al. U.S. Patent Application Publication No. 2003/0152976), and in the printing industry for the attachment of pigments to print media (see commonly owned U.S. patent application Ser. No. 10/935,254).

In some cases commercially useful proteins and peptides may be synthetically generated or isolated from natural sources. However, these methods are often expensive, time consuming and characterized by limited production capacity. The preferred method of protein and peptide production is through the fermentation of recombinantly constructed organisms, engineered to over-express the protein or peptide of interest. Although preferable to synthesis or isolation, recombinant expression of peptides has a number of obstacles to be overcome in order to be a cost-effective means of production. For example, peptides (and in particular short peptides) produced in a cellular environment are susceptible to degradation from the action of native cellular proteases. Additionally, purification can be difficult, resulting in poor yields depending on the nature of the protein or peptide of interest.

One means to mitigate the above difficulties is the use the genetic chimera for protein and peptide expression. A chimeric protein or "fusion protein" is a polypeptide comprising at least one portion of the desired protein product fused to at least one portion comprising a peptide tag. The peptide tag may be used to assist protein folding, assist post expression purification, protect the protein from the action of degradative enzymes, and/or assist the protein in passing through the cell membrane.

In many cases it is useful to express a protein or peptide in insoluble form, particularly when the peptide of interest is rather short, normally soluble, and subject to proteolytic degradation within the host cell. Production of the peptide in insoluble form both facilitates simple recovery and protects the peptide from the undesirable proteolytic degradation. One means to produce the peptide in insoluble form is to recombinantly produce the peptide as part of an insoluble fusion protein by including in the fusion construct at least one peptide tag (i.e., an inclusion body tag) that induces inclusion body formation. Typically, the fusion protein is designed to include at least one cleavable peptide linker so that the peptide of interest can be subsequently recovered from the fusion protein. The fusion protein may be designed to include a plurality of inclusion body tags, cleavable peptide linkers, and regions encoding the peptide of interest.

Fusion proteins comprising a carrier protein tag that facilitates the expression of insoluble proteins are well known in the art. Typically, the tag portion of the chimeric or fusion protein is large, increasing the likelihood that the fusion protein will be insoluble. Example of large peptide tags typically used include, but are not limited to chloramphenicol acetyltransferase (Dykes et al., Eur. J. Biochem., 174:411 (1988), β-galactosidase (Schellenberger et al., Int. J. Peptide Protein Res., 41:326 (1993); Shen et al., Proc. Nat. Acad. Sci. USA 281:4627 (1984); and Kempe et al., Gene, 39:239 (1985)), glutathione-S-transferase (Ray et al., Bio/Technology, 11:64 (1993) and Hancock et al. (WO94/04688)), the N-terminus of L-ribulokinase (U.S. Pat. No. 5,206,154 and Lai et al., Antimicrob. Agents & Chemo., 37:1614 (1993), bacteriophage T4 gp55 protein (Gramm et al., Bio/Technology, 12:1017 (1994), bacterial ketosteroid isomerase protein (Kuliopulos et al., J. Am. Chem. Soc. 116:4599 (1994), ubiquitin (Pilon et al., Biotechnol. Prog., 13:374-79 (1997), bovine prochymosin (Haught et al., Biotechnol. Bioengineer. 57:55-61 (1998), and bactericidal/permeability-increasing protein ("BPI"; Better, M. D. and Gavit, P D., U.S. Pat. No. 6,242,219). The art is replete with specific examples of this technology, see for example U.S. Pat. No. 6,613,548, describing fusion protein of proteinaceous tag and a soluble protein and subsequent purification from cell lysate; U.S. Pat. No. 6,037,145, teaching a tag that protects the expressed chimeric protein from a specific protease; U.S. Pat. No. 5,648,244, teaching the synthesis of a fusion protein having a tag and a cleavable linker for facile purification of the desired protein; and U.S. Pat. No. 5,215,896; 5,302,526; 5,330,902; and US 2005221444, describing fusion tags containing amino acid compositions specifically designed to increase insolubility of the chimeric protein or peptide.

Although the above methods are useful for the expression of fusion proteins, they often incorporate large fusion tags that decrease the potential yield of desired peptide of interest. This is particularly problematic in situations where the desired protein or peptide is small. In such situations it is advantageous to use a small fusion tag to maximized yield.

There remains a need therefore for peptide fusion tags that facilitate the insolubility of fusion proteins where the peptide of interest is small and appreciably soluble in the host cell.

SUMMARY OF THE INVENTION

The stated problem has been solved though the discovery of a set of short inclusion body tags (IBTs) derived from a *Zea mays* zein protein that are useful for synthesizing fusion proteins for increased expression and simple purification of short peptides ("peptides of interest"), especially short peptides useful in affinity applications.

Accordingly, the present invention provides an inclusion body tag comprising at least 15 contiguous amino acids from residues 76 to 175 of SEQ ID NO: 2 with the proviso that the inclusion body tag is not SEQ ID NO: 2.

In another aspect, the invention provides a fusion peptide comprising the inclusion body tag of the invention operably linked to a peptide of interest. The inclusion body tag can be a leader or trailer sequence within the fusion protein. In a preferred aspect, the fusion peptide is engineered to include at least one cleavable peptide linker. Inclusion of a cleavable peptide linker is useful for separating the inclusion body tag and the peptide of interest. In another preferred aspect, the cleavable peptide linker comprises at least one acid cleavable aspartic acid—proline (DP) moiety.

In an additional aspect, the invention provides a method for expressing a peptide of interest in insoluble form comprising:

a) synthesizing a genetic construct encoding a fusion peptide comprising a first portion encoding the inclusion body tag of the invention operably linked to a second portion encoding a peptide of interest;

b) transforming an expression host cell with the genetic construct of (a);

c) growing the transformed host cell of (b) under conditions wherein the genetic construct is expressed and the encoded fusion peptide is in insoluble form; and d) recovering said fusion peptide in insoluble form.

In another embodiment, a method for the production of a peptide of interest is provided comprising:

a) synthesizing a genetic construct encoding a fusion peptide comprising a first portion encoding the inclusion body tag of any of claims 1-3 operably linked to a second portion encoding a peptide of interest; wherein said first portion and said second portion are separated by at least one cleavable peptide linker;

b) transforming an expression host cell with the genetic construct of (a);

c) growing the transformed host cell of (b) under conditions wherein the genetic construct is expressed and the encoded fusion peptide is in insoluble form;

d) recovering the fusion peptide in insoluble form;

e) cleaving said at least one cleavable peptide linker whereby said first portion of the fusion peptide is no longer fused to the peptide of interest; and f) recovering said peptide of interest.

In a further aspect, the invention provides a chimeric genetic construct encoding a fusion protein comprising at least one of the present inclusion body tags and at least one peptide of interest.

In yet another aspect, the invention provides expression vectors and microbial host cells comprising the present chimeric genetic constructs.

BRIEF DESCRIPTION OF THE BIOLOGICAL SEQUENCES

The following sequences comply with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPC and PCT (Rules 5.2 and 49.5(a-bis), and Section 208 and Annex C of the Administrative Instructions). The symbols and format used for nucleotide and amino acid sequence data comply with the rules set forth in 37 C.F.R.§1.822.

A Sequence Listing is provided herewith on Compact Disk. The contents of the Compact Disk containing the Sequence Listing are hereby incorporated by reference in compliance with 37 CFR 1.52(e). The Compact Disks are submitted in triplicate and are identical to one another. The disks are labeled "Copy 1—Sequence Listing", "Copy 2—Sequence Listing", and CRF. The disks contain the following file: CL3262 US NA.ST25 having the following size: 209,000 bytes and which was created Nov. 30, 2006.

SEQ ID NO: 1 is the nucleotide sequence of the opaque2 modifier (also referred to herein as "gamma zeinA") coding region from *Zea mays*.

SEQ ID NO: 2 is the amino acid sequence of the 27 kDa gamma zeinA protein (GenBank® AAP32017).

SEQ ID NO: 3 is the nucleotide sequence of the TBP1 coding sequence encoding the TBP101 peptide.

SEQ ID NO: 4 is the amino acid sequence of the TBP101 peptide.

SEQ ID NOs: 5-9 are the nucleotide sequences of oligonucleotides used to synthesize TBP1.

SEQ ID NO: 10 and 11 are the nucleotide sequences of the primers used to PCR amplify TBP1.

SEQ ID NO: 12 is the nucleotide sequence of pENTR™/D-TOPO® plasmid (Invitrogen, Carlsbad, Calif.).

SEQ ID NO: 13 is the nucleotide sequence of the pDEST plasmid (Invitrogen).

SEQ ID NO: 14 is the nucleotide sequence of the coding region encoding the INK101 fusion peptide.

SEQ ID NO: 15 is the amino acid sequence of the INK101 fusion peptide.

SEQ ID NO: 16 is the nucleotide sequence of plasmid pLX121.

SEQ ID NOs: 17 and 18 are the nucleotide sequences of primers used to introduce an acid cleavable aspartic acid-proline dipeptide linker into TBP101.

SEQ ID NO: 19 is the nucleotide sequence of the coding region encoding the INK101DP peptide.

SEQ ID NO: 20 is the amino acid sequence of the INK101DP peptide.

SEQ ID NOs: 21-110 are the nucleotide sequences of oligonucleotides used to prepare the present inclusion body tags.

SEQ ID NOs: 111-155 are the amino acid sequences of peptides evaluated as potential inclusion body tags.

SEQ ID NOs: 156-245 are the nucleotide and corresponding amino acid sequences of the fusion proteins created by fusing the present inclusion body tags to the modified TBP101 peptide.

SEQ ID NO: 246 is the amino acid sequence of the T7 translational enhancer.

SEQ ID NO: 247 is the amino acid sequence of inclusion body tag IBT-180.

SEQ ID NO: 248 is the amino acid sequence of inclusion body tag IBT-181.

SEQ ID NO: 249 is the nucleic acid sequence of the chimeric gene IBT 180-TBP101.

SEQ ID NO: 250 is the amino acid sequence of the fusion peptide IBT 180-TBP101.

SEQ ID NO: 251 is the nucleic acid sequence of the chimeric gene IBT 181-TBP101.

SEQ ID NO: 252 is the amino acid sequence of the fusion peptide IBT 181-TBP101.

SEQ ID NOs: 253-355 are examples of amino acid sequences of body surface binding peptides, SEQ ID NOs 253-260 are skin binding peptides, SEQ ID NOs 261-353 are hair binding peptides, and SEQ ID NOs: 354-355 are nail binding peptides.

SEQ ID NOs: 356-384 are examples of antimicrobial peptide sequences.

SEQ ID NOs: 385-410 are examples of pigment binding peptides, SEQ ID NOs: 385-388 bind carbon black, SEQ ID NOs: 389-397 are Cromophtal® yellow (Ciba Specialty Chemicals, Basel, Switzerland) binding peptides, SEQ ID NOs: 398-400 are Sunfast® magenta (Sun Chemical Corp., Parsippany, N.J.) binding peptides, and SEQ ID NOs: 401-410 are Sunfast® blue binding peptides.

SEQ ID NOs: 411-444 are examples of polymer binding peptides, SEQ ID NOs: 411-416 are cellulose binding peptides, SEQ ID NO: 417 is a poly(ethylene terephthalate) (PET) binding peptide, SEQ ID NOs: 418-429 are poly(methyl methacrylate) (PMMA) binding peptides, SEQ ID NOs: 430-435 are nylon binding peptides, and SEQ ID NOs: 436-444 are poly(tetrafluoro ethylene) (PTFE) binding peptides.

SEQ ID NO: 445 is the amino acid sequence of the Caspase-3 cleavage site that may be used as a cleavable peptide linker domain.

DETAILED DESCRIPTION OF THE INVENTION

The present invention describes a set of peptide tags (inclusion body tags) that may be coupled with a peptide of interest to form a fusion protein. The fusion protein, so assembled, is expressed in insoluble form and accumulated in inclusion bodies in the expressing host cell. The inclusion bodies may then be recovered and the desired protein cleaved from the inclusion body tag. In a preferred embodiment, the fusion protein comprises at least one cleavable peptide linker separating the inclusion body tag from the peptide of interest. In another preferred embodiment, the cleavable peptide linker comprises at least one acid cleavable aspartic acid—proline moiety.

The invention is useful for the expression and recovery of any bioactive peptides and proteins that are recombinantly expressed. Such proteins typically have high value in any number of applications including, but not limited to medical, biomedical, diagnostic, personal care, and affinity applications where the peptides of interest are used as linkers to various surfaces.

The following definitions are used herein and should be referred to for interpretation of the claims and the specification. Unless otherwise noted, all U.S. patents and U.S. patent applications referenced herein are incorporated by reference in their entirety.

As used herein, the term "comprising" means the presence of the stated features, integers, steps, or components as referred to in the claims, but that it does not preclude the presence or addition of one or more other features, integers, steps, components or groups thereof.

The term "invention" or "present invention" as used herein is a non-limiting term and is not intended to refer to any single embodiment of the particular invention but encompasses all possible embodiments as described in the specification and the claims.

"Open reading frame" is abbreviated ORF.

"Polymerase chain reaction" is abbreviated PCR.

As used herein, the term "isolated nucleic acid molecule" is a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

As used herein, the term "hair" as used herein refers to human hair, eyebrows, and eyelashes.

As used herein, the term "skin" as used herein refers to human skin, or substitutes for human skin, such as pig skin, Vitro-Skin® and EpiDerm™. Skin, as used herein, will refer to a body surface generally comprising a layer of epithelial cells and may additionally comprise a layer of endothelial cells.

As used herein, the term "nails" as used herein refers to human fingernails and toenails and other body surfaces comprised primarily of keratin.

As used herein, the term "pigment" refers to an insoluble, organic or inorganic colorant.

As used herein, "HBP" means hair-binding peptide. Examples of hair binding peptides have been reported (U.S. patent application Ser. No. 11/074,473 to Huang et al.; WO 0179479; U.S. Patent Application Publication No. 2002/0098524 to Murray et al.; Janssen et al., U.S. Patent Application Publication No. 2003/0152976 to Janssen et al.; WO 04048399; U.S. Provisional Application No. 60/721,329, and U.S. Provisional Patent Application No. 60/790,149).

As used herein, "SBP" means skin-binding peptide. Examples of skin binding peptides have also been reported (U.S. patent application Ser. No. 11/069,858 to Buseman-Williams; Rothe et. al., WO 2004/000257; and U.S. Provisional Patent Application No. 60/790,149).

As used herein, "NBP" means nail-binding peptide. Examples of nail binding peptides have been reported (U.S. Provisional Patent Application No. 60/790,149).

As used herein, an "antimicrobial peptide" is a peptide having the ability to kill microbial cell populations (U.S. Provisional Patent Application No. 60/790,149).

As used herein, the terms "zein 27 kDa storage protein", "zein protein", "gamma zein protein", and "opaque2 protein" will refer to the *Zea mays* protein having the amino acid sequence as set forth in SEQ ID NO:2 (GenBank® Accession No. AAP32017). The coding region encoding the zein protein having GenBank® Accession No. AAP32017 is provided as SEQ ID NO: 1.

As used herein, the term "inclusion body tag" will be abbreviated "IBT" and will refer a polypeptide that facilitates/stimulates formation of inclusion bodies when fused to a peptide of interest. The peptide of interest is typically soluble within the host cell and/or host cell lysate when not fused to an inclusion body tag. Fusion of the peptide of interest to the inclusion body tag produces an insoluble fusion protein that typically agglomerates into intracellular bodies (inclusion bodies) within the host cell. In one embodiment, the fusion protein comprises at least one portion comprising an inclusion body tag and at least one portion comprising the polypeptide of interest. In one embodiment, the protein/polypeptides of interest are separated from the inclusion body tags using cleavable peptide linker elements.

As used herein, "T7 translational enhancer element" means the N-terminal coding sequence of bacteriophage T7 gene 10 (Rosenberg, A H et al., *Gene* 56:125-135 (1987)), which provides a standardized sequence at the critical translation initiation site in the genes encoding IBT-180 and IBT-181.

As used herein, "cleavable linker elements", "peptide linkers", and "cleavable peptide linkers" will be used interchangeably and refer to cleavable peptide segments typically found between inclusion body tags and the peptide of interest. After the inclusion bodies are separated and/or partially-purified or purified from the cell lysate, the cleavable linker elements can be cleaved chemically and/or enzymatically to separate the inclusion body tag from the peptide of interest. The peptide of interest can then be isolated from the inclusion body tag, if necessary. In one embodiment, the inclusion body tag(s) and the peptide of interest exhibit different solubilities in a defined medium (typically an aqueous medium), facilitating separation of the inclusion body tag from the protein/polypeptide of interest. In a preferred embodiment, the inclusion body tag is insoluble in an aqueous solution while the protein/polypeptide of interest is appreciably soluble in an aqueous solution. The pH, temperature, and/or ionic strength of the aqueous solution can be adjusted to facilitate recovery of the peptide of interest. In a preferred embodiment, the differential solubility between the inclusion body tag and the peptide of interest occurs in an aqueous solution having a pH of 5 to 10 and a temperature range of 15 to 50° C. The cleavable peptide linker may be from 1 to about 50 amino acids, preferably from 1 to about 20 amino acids in length. An example of a cleavable peptide linker is provided by SEQ ID NO: 445 (Caspase-3 cleavage sequence). The cleavable peptide linkers may be incorporated into the fusion proteins using any number of techniques well known in the art.

As used herein, the term "dispersant" as used herein refers to a substance that stabilizes the formation of a colloidal solution of solid pigment particles in a liquid medium. As used herein, the term "triblock dispersant" to a pigment dispersant that consists of three different units or blocks, each serving a specific function. In the present examples, a synthetic peptide encoding a peptide-based triblock dispersant was used as the "peptide of interest" to evaluate the performance of the present inclusion body tags (U.S. Ser. No. 10/935,254).

As used herein, the term "operably linked" refers to the association of nucleic acid sequences on a single nucleic acid fragment so that the function of one is affected by the other. For example, a promoter is operably linked with a coding sequence when it is capable of effecting the expression of that coding sequence (i.e., that the coding sequence is under the transcriptional control of the promoter). In a further embodiment, the definition of "operably linked" may also be extended to describe the products of chimeric genes, such as fusion proteins. As such, "operably linked" will also refer to the linking of an inclusion body tag to a peptide of interest to be produced and recovered. The inclusion body tag is "operably linked" to the peptide of interest if upon expression the fusion protein is insoluble and accumulates it inclusion bodies in the expressing host cell. In a preferred embodiment, the fusion peptide will include at least one cleavable peptide linker useful in separating the inclusion body tag from the peptide of interest. In a further preferred embodiment, the cleavable linker is an acid cleavable aspartic acid—proline dipeptide (D-P) moiety (see INK101DP; SEQ ID NO: 20). The cleavable peptide linkers may be incorporated into the fusion proteins using any number of techniques well known in the art.

As used herein, the terms "fusion protein", "fusion peptide", "chimeric protein", and "chimeric peptide" will be used interchangeably and will refer to a polymer of amino acids (peptide, oligopeptide, polypeptide, or protein) comprising at least two portions, each portion comprising a distinct function. One portion of the fusion peptide will comprise at least one of the present inclusion body tags. The second portion comprises at least one peptide of interest. In a preferred embodiment, the fusion protein additionally includes at least one cleavable peptide linker that facilitates cleavage (chemical and/or enzymatic) and separation of the inclusion body tag(s) and the peptide(s) of interest.

Means to prepare the present peptides (inclusion body tags, cleavable peptide linkers, peptides of interest, and fusion peptides) are well known in the art (see, for example, Stewart et al., *Solid Phase Peptide Synthesis*, Pierce Chemical Co., Rockford, Ill., 1984; Bodanszky, *Principles of Peptide Synthesis*, Springer-Verlag, N.Y., 1984; and Pennington et al., *Peptide Synthesis Protocols*, Humana Press, Totowa, N.J., 1994). The various components of the fusion peptides (inclusion body tag, peptide of interest, and the cleavable linker) described herein can be combined using carbodiimide coupling agents (see for example, Hermanson, Greg T., *Bioconjugate Techniques*, Academic Press, New York (1996)), diacid chlorides, diisocyanates and other difunctional coupling reagents that are reactive to terminal amine and/or carboxylic acid groups on the peptides. However, chemical synthesis is often limited to peptides of less than about 50 amino acids length due to cost and/or impurities. In a preferred alternative embodiment, the entire peptide reagent may be prepared using the recombinant DNA and molecular cloning techniques.

As used herein, the terms "polypeptide" and "peptide" will be used interchangeably to refer to a polymer of two or more amino acids joined together by a peptide bond, wherein the peptide is of unspecified length, thus, peptides, oligopeptides, polypeptides, and proteins are included within the present definition. In one aspect, this term also includes post expression modifications of the polypeptide, for example, glycosylations, acetylations, phosphorylations and the like. Included within the definition are, for example, peptides containing one or more analogues of an amino acid or labeled amino acids and peptidomimetics.

As used herein, the terms "protein of interest", "polypeptide of interest", "peptide of interest", "targeted protein", "targeted polypeptide", "targeted peptide", "expressible protein", and "expressible polypeptide" will be used interchangeably and refer to a protein, polypeptide, or peptide that is bioactive and may be expressed by the genetic machinery of a host cell.

As used herein, the terms "bioactive" and "peptide of interest activity" are used interchangeably and refer to the activity or characteristic associated with the peptide and/or protein of interest. The bioactive peptides may be used in a variety of applications including, but not limited to curative agents for diseases (e.g., insulin, interferon, interleukins, anti-angiogenic peptides (U.S. Pat. No. 6,815,426), and polypeptides that bind to defined cellular targets such as receptors, channels, lipids, cytosolic proteins, and membrane proteins, to name a few), peptides having antimicrobial activity, peptides having an affinity for a particular material (e.g., hair binding polypeptides, skin binding polypeptides, nail binding polypeptides, cellulose binding polypeptides, polymer binding polypeptides, clay binding polypeptides, silicon binding polypeptides, carbon nanotube binding polypeptides, and peptides that have an affinity for particular animal or plant tissues) for targeted delivery of benefit agents.

As used herein, the "benefit agent" refers to a molecule that imparts a desired functionality to the complex for a defined application. The benefit agent may be peptide of interest itself or may be one or more molecules bound to (covalently or non-covalently), or associated with, the peptide of interest wherein the binding affinity of the targeted polypeptide is used to selectively target the benefit agent to the targeted material. In another embodiment, the targeted polypeptide comprises at least one region having an affinity for at least one target material (e.g., biological molecules, polymers, hair, skin, nail, other peptides, etc.) and at least one region having an affinity for the benefit agent (e.g., pharmaceutical agents, pigments, conditioners, dyes, fragrances, etc.). In another embodiment, the peptide of interest comprises a plurality of regions having an affinity for the target material and a plurality of regions having an affinity for the benefit agent. In yet another embodiment, the peptide of interest comprises at least one region having an affinity for a targeted material and a plurality of regions having an affinity for a variety of benefit agents wherein the benefit agents may be the same of different. Examples of benefits agents may include, but are not limited to conditioners for personal care products, pigments, dye, fragrances, pharmaceutical agents (e.g., targeted delivery of cancer treatment agents), diagnostic/labeling agents, ultraviolet light blocking agents (i.e., active agents in sunscreen protectants), and antimicrobial agents (e.g., antimicrobial peptides), to name a few.

As used herein, an "inclusion body" is an intracellular amorphous deposit comprising aggregated protein found in the cytoplasm of a cell. Peptides of interest that are typically soluble with the host cell and/or cell lysates can be fused to one or more of the present inclusion body tags to facilitate formation of an insoluble fusion protein. In an alternative embodiment, the peptide of interest may be partially insoluble in the host cell, but produced at relatively lows levels where significant inclusion body formation does not occur. As such, the formation of inclusion bodies will increase protein. In a further embodiment, fusion of the peptide of interest to one or more inclusion body tags (IBTs) increases the amount of protein produced in the host cell. Formation of the inclusion body facilitates simple and efficient purification of the fusion peptide from the cell lysate using techniques well known in the art such as centrifugation and filtration. The fusion protein typically includes one or more cleavable peptide linkers used to separate the protein/polypeptide of interest from the inclusion body tag(s). The cleavable peptide linker is designed so that the inclusion body tag(s) and the protein/polypeptide(s) of interest can be easily separated by cleaving the linker element. The peptide linker can be cleaved chemically (e.g., acid hydrolysis) or enzymatically (i.e., use of a protease/peptidase that preferentially recognizes an amino acid cleavage site and/or sequence within the cleavable peptide linker).

"Codon degeneracy" refers to the nature in the genetic code permitting variation of the nucleotide sequence without affecting the amino acid sequence of an encoded polypeptide. Accordingly, the instant invention relates to any nucleic acid fragment that encodes the present amino acid sequences. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

As used herein, the term "solubility" refers to the amount of a substance that can be dissolved in a unit volume of a liquid under specified conditions. In the present application, the term "solubility" is used to describe the ability of a peptide (inclusion body tag, peptide of interest, or fusion peptides) to be resuspended in a volume of solvent, such as a biological buffer. In one embodiment, the peptides targeted for production ("peptides of interest") are normally soluble in the cell and/or cell lysate under normal physiological conditions. Fusion of one or more inclusion body tags (IBTs) to the target peptide results in the formation of a fusion peptide that is insoluble under normal physiological conditions, resulting in the formation of inclusion bodies. In one embodiment, the peptide of interest is insoluble in an aqueous matrix having a pH range of 5-12, preferably 6-10; and a temperature range of 5° C. to 5° C., preferably 10° C. to 40° C. Fusion of the peptide of interest to at least one of the present inclusion body tags results in the formation of an insoluble fusion protein that agglomerates into at least one inclusion body under normal physiological conditions.

The term "amino acid" refers to the basic chemical structural unit of a protein or polypeptide. The following abbreviations are used herein to identify specific amino acids:

| Amino Acid | Three-Letter Abbreviation | One-Letter Abbreviation |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Miscellaneous (as defined by the present formulas) | Xaa | X |

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences "Chimeric gene" refers to any gene that is not a native gene, comprising regulatory and coding sequences (including coding regions engineered to encode fusion peptides) that are not found together in nature. Accordingly, a chimeric gene may comprise regulatory sequences and coding sequences that are derived from different sources, or regulatory sequences and coding sequences derived from the same source, but arranged in a manner different than that found in nature. A "foreign" gene refers to a gene not normally found in the host organism, but that is introduced into the host organism by gene transfer. Foreign genes can comprise native genes inserted into a non-native organism, or chimeric genes.

As used herein, the term "coding sequence" refers to a DNA sequence that encodes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, enhancers, ribosomal binding sites, translation leader sequences, introns, polyadenylation recognition sequences, RNA processing site, effector binding site and stem-loop structures. One of skill in the art recognizes that selection of suitable regulatory sequences will depend upon host cell and/or expression system used.

As used herein, the term "genetic construct" refers to a series of contiguous nucleic acids useful for modulating the genotype or phenotype of an organism. Non-limiting examples of genetic constructs include but are not limited to a nucleic acid molecule, an open reading frame, a gene, a plasmid, and the like.

As used herein, the term "expression ranking" means the relative yield of insoluble fusion protein estimated visually and scored on a relative scale of 0 (no insoluble fusion peptide) to 3 (highest yield of insoluble fusion peptide). As described in the present examples, the relative yield of insoluble fusion protein was estimated visually from stained polyacrylamide gels.

As used herein, the term "transformation" refers to the transfer of a nucleic acid fragment into the genome of a host organism, resulting in genetically stable inheritance. As used herein, the host cell's genome is comprised of chromosomal and extrachromosomal (e.g., plasmid) genes. Host organisms containing the transformed nucleic acid fragments are referred to as "transgenic" or "recombinant" or "transformed" organisms.

As used herein, the term "host cell" refers to cell which has been transformed or transfected, or is capable of transformation or transfection by an exogenous polynucleotide sequence.

As used herein, the terms "plasmid", "vector" and "cassette" refer to an extrachromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in a foreign host.

Standard recombinant DNA and molecular cloning techniques used herein are well known in the art and are described by Sambrook, J., Fritsch, E. F. and Maniatis, T., *Molecular Cloning: A Laboratory Manual,* Third Edition, Cold Spring Harbor Laboratory Press, Cold Spring Harbor, N.Y. (2001) (hereinafter "Maniatis"); and by Silhavy, T. J., Bennan, M. L. and Enquist, L. W., *Experiments with Gene Fusions,* Cold Spring Harbor Laboratory Cold Press Spring Harbor, N.Y. (1984); and by Ausubel, F. M. et al., *Current Protocols in Molecular Biology,* published by Greene Publishing Assoc. and Wiley-Interscience (1987).

Inclusion Body Tags

The inclusion body tags of the invention were derived from the gamma zein 27kDA storage protein (GenBank® accession No. AAP32017; SEQ ID NO: 2). This protein was selected as the starting material for preparation of a library of putative inclusion body tags. Several overlapping series of approximately 15 amino acid long peptides (one was 13 amino acids in length) were prepared and evaluated as potential inclusion body tags. The library was prepared by synthesizing and fusing short peptides identical to various portions of the zein protein to a soluble peptide of interest (the modified TBP101 peptide). Expression analysis identified a central region of the zein protein (amino acid residues 76 through 175 of SEQ ID NO: 2) suitable for the preparation of the present inclusion body tags. Short (15 or more contiguous amino acids) inclusion body tags prepared from this region were able to induce inclusion body formation (i.e. form insoluble fusion peptides) when fused to a peptide of interest (typically soluble).

Each of the present fusion tags was fused to a standard peptide of interest (a modified version of TBP101 incorporating an acid cleavable aspartic acid—proline moiety useful in separating the peptide of interest from the inclusion body tag; see Example 1). TBP101 (when not linked to an inclusion body tag) is soluble in the present test system. Each constructed was recombinantly expressed in an appropriate host cell and evaluated for insoluble fusion peptide formation.

The present inclusion body tags are peptides comprising at least 15 contiguous amino acid from amino acid residues 76 to 175 of SEQ ID NO: 2 with the proviso that the inclusion body tag is not equal to SEQ ID NO: 2 or any other full length zein protein. In one embodiment, the inclusion body tags may comprise additional amino acid residues flanking the present peptide sequences so long as the ability to form insoluble fusion peptides in not adversely affected with the proviso that the amino acid sequence of the inclusion body tag is not identical to SEQ ID NO: 2. In another embodiment, portion of the fusion protein comprising the inclusion body tag of the present invention is 15 to no more than 100 amino acid residues in length, preferably 15 to 50 amino acids in length, more preferably 15 to 25 amino acids in length, and most preferably about 15 amino acids in length.

In one embodiment, the present inclusion body tags are selected from the group consisting of SEQ ID NOs: 116, 117, 119, 121, 131, 132, 133, 135, 145, 147, 148, 149, 150, 154, 155, 247, and 248.

Inclusion body tags IBT-180 and IBT-181 each include a T7 translational enhancer element (SEQ ID NO: 246) fused to the amino terminal portion of an inclusion body tag derived the zein protein. In one aspect, any of the present inclusion body tags may optionally include the T7 translational enhancer as represented by SEQ ID NO: 246 fused to the amino terminus of an inclusion body tag comprising at least 15 contiguous amino acids from amino acid residues 76 to 175 of SEQ ID NO: 2.

In another aspect, the present invention also includes fusion peptides comprising at least one of the present inclusion body tags fused to at least one peptide of interest. In a preferred embodiment, the fusion peptide includes at least one cleavable peptide linker useful in separating the peptide of interest from the inclusion body tag(s). The cleavable peptide linker can be an enzymatic cleavage sequence or a chemically cleavable sequence. In another preferred embodiment, the cleavable peptide linker comprises at least one acid cleavable aspartic acid—proline moiety (for example, see the INK101DP peptide; SEQ ID NO: 20).

Expressible Peptides of Interest

The peptide of interest ("expressible peptide") targeted for production using the present method is one that is appreciably soluble in the host cell and/or host cell liquid lysate under normal physiological conditions. In a preferred aspect, the peptides of interest are generally short (<50 amino acids in length) and difficult to produce in sufficient amounts due to proteolytic degradation. Fusion of the peptide of interest to at least one of the present inclusion body forming tags creates a fusion peptide that is insoluble in the host cell and/or host cell lysate under normal physiological conditions. Production of the peptide of interest is typically increased when expressed and accumulated in the form of an insoluble inclusion body as the peptide is generally more protected from proteolytic degradation. Furthermore, the insoluble fusion protein can be easily separated from the host cell lysate using centrifugation or filtration.

In general, the present inclusion body tags can be used in a process to produce any peptide of interest that is (1) typically soluble in the cell and/or cell lysate under typical physiological conditions and/or (2) those that can be produced at significantly higher levels when expressed in the form of an inclusion body. In a preferred embodiment, the peptide of interest is appreciably soluble in the host cell and/or corresponding cell lysate under normal physiological and/or process conditions.

The length of the peptide of interest may vary as long as (1) the peptide is appreciably soluble in the host cell and/or cell lysate, and/or (2) the amount of the targeted peptide produced is significantly increased when expressed in the form of an insoluble fusion peptide/inclusion body (i.e. expression in the form of a fusion protein protect the peptide of interest from proteolytic degradation). Typically the peptide of interest is less than 200 amino acids in length, preferably less than 100 amino acids in length, more preferably less than 75 amino acids in length, even more preferably less than 50 amino acids in length, and most preferably less than 25 amino acids in length.

The function of the peptide of interest is not limited by the present method and may include, but is not limited to bioactive molecules such as curative agents for diseases (e.g., insulin, interferon, interleukins, peptide hormones, anti-angiogenic peptides, and peptides that bind to and affect defined cellular targets such as receptors, channels, lipids, cytosolic proteins, and membrane proteins; see U.S. Pat. No. 6,696, 089,), peptides having an affinity for a particular material (e.g., biological tissues, biological molecules, hair binding peptides (U.S. patent application Ser. No. 11/074,473; WO 0179479; U.S. Patent Application Publication No. 2002/0098524; U.S. Patent Application Publication No. 2003/0152976; WO 04048399; U.S. Provisional Patent Application No. 60/721,329; and U.S. Provisional Patent Application No. 60/790,149), skin binding peptides (U.S. patent application Ser. No. 11/069,858; WO 2004/000257; and U.S. Provisional Patent Application No. 60/790,149), nail binding peptides (U.S. Provisional Patent Application No. 60/790,149), cellulose binding peptides, polymer binding peptides (U.S. Provision Patent Application Nos. 60/750,598, 60/750,599, 60/750,726, 60/750,748, and 60/750,850), clay binding peptides, silicon binding peptides, and carbon nanotube binding peptides) for targeted delivery of at least one benefit agent (see U.S. patent application Ser. No. 10/935,642; U.S. patent application Ser. No. 11/074,473; and U.S. Provisional Patent Application No. 60/790,149).

In a preferred aspect, the peptide of interest is selected from the group of hair binding peptides (U.S. patent application Ser. No. 11/074,473; WO 0179479; U.S. Patent Application Publication No. 2002/0098524; Janssen et al., U.S. Patent Application Publication No. 2003/0152976; WO 04048399; U.S. Provisional Patent Application No. 60/721,329; and U.S. Provisional Patent Application No. 60/790,149), skin binding peptides (U.S. patent application Ser. No. 11/069, 858; WO 2004/000257; and U.S. Provisional Patent Application No. 60/790,149), nail binding peptides (U.S. Provisional Patent Application No. 60/790,149), antimicrobial peptides (U.S. Provisional Patent Application No. 60/790,149), and polymer binding peptides (U.S. Provision Patent Application Nos. 60/750,598, 60/750,599, 60/750,726, 60/750,748, and 60/750,850). In another preferred aspect, the hair binding peptide is selected from the group consisting of SEQ ID NOs: (261-353); the skin binding peptide is selected from the group consisting of SEQ ID NOs: (253-260); the nail binding peptide is selected from the group consisting of SEQ ID NOs: (354-355); the antimicrobial peptide is selected from the group consisting of SEQ ID NOs: (356-384); and the polymer binding peptide is selected from the group consisting of SEQ ID NOs: (411-444).

As used herein, the "benefit agent" refers to a molecule that imparts a desired functionality to a target material (e.g., hair, skin, etc.) for a defined application (U.S. patent application Ser. No. 10/935,642; U.S. patent application Ser. No. 11/074, 473; and U.S. Patent Application 60/790,149 for a list of typical benefit agents such as conditioners, pigments/colorants, fragrances, etc.). The benefit agent may be the peptide of interest itself or may be one or more molecules bound to (covalently or non-covalently), or associated with, the peptide of interest wherein the binding affinity of the peptide of interest is used to selectively target the benefit agent to the targeted material. In another embodiment, the peptide of interest comprises at least one region having an affinity for at least one target material (e.g., biological molecules, polymers, hair, skin, nail, other peptides, etc.) and at least one region having an affinity for the benefit agent (e.g., pharmaceutical agents, antimicrobial agents, pigments, conditioners, dyes, fragrances, etc.). In another embodiment, the peptide of interest comprises a plurality of regions having an affinity for the target material and a plurality of regions having an affinity for one or more benefit agents. In yet another embodiment, the peptide of interest comprises at least one region having an affinity for a targeted material and a plurality of regions having an affinity for a variety of benefit agents wherein the benefit agents may be the same of different. Examples of benefits agents may include, but are not limited to conditioners for personal care products, pigments, dye, fragrances, pharmaceutical agents (e.g., targeted delivery of cancer treatment agents), diagnostic/labeling agents, ultraviolet light blocking agents (i.e., active agents in sunscreen protectants), and antimicrobial agents (e.g., antimicrobial peptides), to name a few.

Cleavable Peptide Linkers

The use of cleavable peptide linkers is well known in the art. Fusion peptides comprising the present inclusion body tags will typically include at least one cleavable sequence separating the inclusion body tag from the polypeptide of interest. The cleavable sequence facilitates separation of the inclusion body tag(s) from the peptide(s) of interest. In one embodiment, the cleavable sequence may be provided by a portion of the inclusion body tag and/or the peptide of interest (e.g., inclusion of an acid cleavable aspartic acid—proline moiety; see INK101 DP (SEQ ID NO: 20)). In a preferred embodiment, the cleavable sequence is provided by including (in the fusion peptide) at least one cleavable peptide linker between the inclusion body tag and the peptide of interest.

Means to cleave the peptide linkers are well known in the art and may include chemical hydrolysis, enzymatic cleavage agents, and combinations thereof. In one embodiment, one or more chemically cleavable peptide linkers are included in the fusion construct to facilitate recovery of the peptide of interest from the inclusion body fusion protein. Examples of chemical cleavage reagents include cyanogen bromide (cleaves methionine residues), N-chloro succinimide, iodobenzoic acid or BNPS-skatole [2-(2-nitrophenylsulfenyl)-3-methylindole] (cleaves tryptophan residues), dilute acids (cleaves at aspartyl-prolyl bonds), and hydroxylamine (cleaves at asparagine-glycine bonds at pH 9.0); see Gavit, P. and Better, M., *J. Biotechnol.*, 79:127-136 (2000); Szoka et al., *DNA*, 5(1):11-20 (1986); and Walker, J. M., *The Proteomics Protocols Handbook*, 2005, Humana Press, Totowa, N.J.)). In a preferred embodiment, one or more aspartic acid—proline acid cleavable recognition sites (i.e., a cleavable peptide linker comprising one or more D-P dipeptide moieties) are included in the fusion protein construct to facilitate separation of the inclusion body tag(s) form the peptide of interest. In another embodiment, the fusion peptide may include multiple regions encoding peptides of interest separated by one or more cleavable peptide linkers.

In another embodiment, one or more enzymatic cleavage sequences are included in the fusion protein construct to facilitate recovery of the peptide of interest. Proteolytic enzymes and their respective cleavage site specificities are well known in the art. In a preferred embodiment, the proteolytic enzyme is selected to specifically cleave only the peptide linker separating the inclusion body tag and the peptide of interest. Examples of enzymes useful for cleaving the peptide linker include, but are not limited to Arg-C proteinase, Asp-N endopeptidase, chymotrypsin, clostripain, enterokinase, Factor Xa, glutamyl endopeptidase, Granzyme B, *Achromobacter* proteinase I, pepsin, proline endopeptidase, proteinase K, *Staphylococcal* peptidase I, thermolysin, thrombin, trypsin, and members of the Caspase family of proteolytic enzymes (e.g. Caspases 1-10) (Walker, J. M., supra). An example of a cleavage site sequence is provided by SEQ ID NO: 445 (Caspase-3 cleavage site; Thornberry et al., *J. Biol. Chem.*, 272:17907-17911 (1997) and Tyas et al., *EMBO Reports*, 1 (3):266-270 (2000)).

Typically, the cleavage step occurs after the insoluble inclusion bodies and/or insoluble fusion peptides are isolated from the cell lysate. The cells can be lysed using any number of means well known in the art (e.g. mechanical and/or chemical lysis). Methods to isolate the insoluble inclusion bodies/fusion peptides from the cell lysate are well known in the art (e.g., centrifugation, filtration, and combinations thereof). Once recovered from the cell lysate, the insoluble inclusion bodies and/or fusion peptides can be treated with a cleavage agent (chemical or enzymatic) to cleavage the inclusion body tag from the peptide of interest. In one embodiment, the fusion protein and/or inclusion body is diluted and/or dissolved in a suitable solvent prior to treatment with the cleavage agent. In a further embodiment, the cleavage step may be omitted if the inclusion body tag does not interfere with the activity of the peptide of interest.

After the cleavage step, and in a preferred embodiment, the peptide of interest can be separated and/or isolated from the fusion protein and the inclusion body tags based on a differential solubility of the components. Parameters such as pH, salt concentration, and temperature may be adjusted to facilitate separation of the inclusion body tag from the peptide of interest. In one embodiment, the peptide of interest is soluble while the inclusion body tag and/or fusion protein is insoluble in the defined process matrix (typically an aqueous matrix). In another embodiment, the peptide of interest is insoluble while the inclusion body tag is soluble in the defined process matrix.

In an alternate embodiment, the peptide of interest may be further purified using any number of well known purification techniques in the art such as ion exchange, gel purification techniques, and column chromatography (see U.S. Pat. No. 5,648,244), to name a few.

Fusion Peptides

The present inclusion body tags are used to create chimeric polypeptides ("fusion peptides" or "fusion proteins") that are insoluble within the host cell, forming inclusion bodies. Synthesis and expression of expressible genetic constructs encoding the present fusion peptides is well known to one of skill in the art given the present inclusion body tags.

The present fusion peptides will include at least one of the present inclusion body tags (IBTs) operably linked to at least one peptide of interest. Typically, the fusion peptides will also include at least one cleavable peptide linker having a cleavage site between the inclusion body tag and the peptide of interest. In one embodiment, the inclusion body tag may include a cleavage site whereby inclusion of a separate cleavable peptide linker may not be necessary. In a preferred embodiment, the cleavage method is chosen to ensure that the peptide of interest is not adversely affected by the cleavage agent(s) employed. In a further embodiment, the peptide of interest may be modified to eliminate possible cleavage sites with the peptide so long as the desired activity of the peptide is not adversely affected.

One of skill in the art will recognize that the elements of the fusion protein can be structured in a variety of ways. Typically, the fusion protein will include at least one IBT, at least one peptide of interest (POI), and at least one cleavable linker (CL) located between the IBT and the POI. The inclusion body tag may be organized as a leader sequence or a terminator sequence relative to the position of the peptide of interest within the fusion peptide. In another embodiment, a plurality of IBTs, POIs, and CLs are used when engineering the fusion peptide. In a further embodiment, the fusion peptide may include a plurality of IBTs (as defined herein), POIs, and CLs that are the same or different.

The fusion peptide should be insoluble in an aqueous matrix at a temperature of 10° C. to 50° C., preferably 10° C. to 40° C. The aqueous matrix typically comprises a pH range of 5 to 12, preferably 6 to 10, and most preferably 6 to 8. The temperature, pH, and/or ionic strength of the aqueous matrix can be adjusted to obtain the desired solubility characteristics of the fusion peptide/inclusion body.

Method to Make a Peptide of Interest Using Insoluble Fusion Peptides

The present inclusion body tags are used to make fusion peptides that form inclusion bodies within the production host. This method is particularly attractive for producing significant amounts of soluble peptide of interest that (1) are difficult to isolation from other soluble components of the cell lysate and/or (2) are difficult to product in significant amounts within the target production host.

In the present methods, a peptide of interest is fused to at least one of the present inclusion body tags, forming an insoluble fusion protein. Expression of the genetic construct encoding the fusion protein produces an insoluble form of the peptide of interest that accumulates in the form of inclusion bodies within the host cell. The host cell is grown for a period of time sufficient for the insoluble fusion peptide to accumulate within the cell.

The host cell is subsequently lysed using any number of techniques well known in the art. The insoluble fusion peptide/inclusion bodies are then separated from the soluble components of the cell lysate using a simple and economical technique such as centrifugation and/or membrane filtration. The insoluble fusion peptide/inclusion body can then be further processed in order to isolate the peptide of interest. Typically, this will include resuspension of the fusion peptide/inclusion body in a liquid matrix suitable for cleaving the fusion peptide, separating the inclusion body tag from the peptide of interest. The fusion protein is typically designed to include a cleavable peptide linker separating the inclusion body tag from the peptide of interest. The cleavage step can be conducted using any number of techniques well known in the art (chemical cleavage, enzymatic cleavage, and combinations thereof). The peptide of interest can then be separated from the inclusion body tag(s) and/or fusion peptides using any number of techniques well known in the art (centrifugation, filtration, precipitation, column chromatography, etc.). Preferably, the peptide of interest (once cleaved from fusion peptide) has a solubility that is significantly different than that of the inclusion body tag and/or remaining fusion peptide.

Transformation and Expression

Once the inclusion body tag has been identified and paired with the appropriate peptide of interest, construction of cassettes and vectors that may be transformed in to an appropriate expression host is common and well known in the art. Typically, the vector or cassette contains sequences directing transcription and translation of the relevant chimeric gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters, which are useful to drive expression of the genetic constructs encoding the fusion peptides in the desired host cell, are numerous and familiar to those skilled in the art. Virtually any promoter capable of driving these constructs is suitable for the present invention including but not limited to CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, ara (pBAD), tet, trp, $IP_L$, $IP_R$, T7, tac, and trc (useful for expression in *Escherichia coli*) as well as the amy, apr, npr promoters and various phage promoters useful for expression in *Bacillus*.

Termination control regions may also be derived from various genes native to the preferred hosts. Optionally, a termination site may be unnecessary, however, it is most preferred if included.

Preferred host cells for expression of the present fusion peptides are microbial hosts that can be found broadly within the fungal or bacterial families and which grow over a wide range of temperature, pH values, and solvent tolerances. For example, it is contemplated that any of bacteria, yeast, and filamentous fungi will be suitable hosts for expression of the present nucleic acid molecules encoding the fusion peptides. Because of transcription, translation, and the protein biosynthetic apparatus is the same irrespective of the cellular feedstock, genes are expressed irrespective of the carbon feedstock used to generate the cellular biomass. Large-scale microbial growth and functional gene expression may utilize a wide range of simple or complex carbohydrates, organic acids and alcohols (i.e. methanol), saturated hydrocarbons such as methane or carbon dioxide in the case of photosynthetic or chemoautotrophic hosts. However, the functional genes may be regulated, repressed or depressed by specific growth conditions, which may include the form and amount of nitrogen, phosphorous, sulfur, oxygen, carbon or any trace micronutrient including small inorganic ions. In addition, the regulation of functional genes may be achieved by the presence or absence of specific regulatory molecules that are added to the culture and are not typically considered nutrient or energy sources. Growth rate may also be an important regulatory factor in gene expression. Examples of host strains include, but are not limited to fungal or yeast species such as *Aspergillus, Trichoderma, Saccharomyces, Pichia, Candida, Hansenula*, or bacterial species such as *Salmonella, Bacillus, Acinetobacter, Zymomonas, Agrobacterium, Erythrobacter, Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella*, and *Myxococcus*. Preferred bacterial host strains include *Escherichia* and *Bacillus*. In a highly preferred aspect, the host strain is *Escherichia coli*.

Fermentation Media

Fermentation media in the present invention must contain suitable carbon substrates. Suitable substrates may include but are not limited to monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally the carbon substrate may also be one-carbon substrates such as carbon dioxide, or methanol for which metabolic conversion into key biochemical intermediates has been demonstrated. In addition to one and two carbon substrates methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth C1 Compd.*, [Int. Symp.], 7th (1993), 415-32. Editor(s): Murrell, J. Collin; Kelly, Don P. Publisher: Intercept, Andover, UK). Similarly, various species of *Candida* will metabolize alanine or oleic acid (Sulter et al., *Arch. Microbiol.* 153:485-489 (1990)). Hence it is contemplated that the source of carbon utilized in the present invention may encompass a wide variety of carbon containing substrates and will only be limited by the choice of organism.

Although it is contemplated that all of the above mentioned carbon substrates and mixtures thereof are suitable in the present invention, preferred carbon substrates are glucose, fructose, and sucrose.

In addition to an appropriate carbon source, fermentation media must contain suitable minerals, salts, cofactors, buffers and other components, known to those skilled in the art, suitable for the growth of the cultures and promotion of the expression of the present fusion peptides.

Culture Conditions

Suitable culture conditions can be selected dependent upon the chosen production host. Typically, cells are grown at a temperature in the range of about 25° C. to about 40° C. in an appropriate medium. Suitable growth media in the present invention are common commercially prepared media such as Luria Bertani (LB) broth, Sabouraud Dextrose (SD) broth or Yeast medium (YM) broth. Other defined or synthetic growth media may also be used and the appropriate medium for growth of the particular microorganism will be known by one skilled in the art of microbiology or fermentation science. The use of agents known to modulate catabolite repression directly or indirectly, e.g., cyclic adenosine 2':3'-monophosphate, may also be incorporated into the fermentation medium.

Suitable pH ranges for the fermentation are typically between pH 5.0 to pH 9.0, where pH 6.0 to pH 8.0 is preferred.

Fermentations may be performed under aerobic or anaerobic conditions wherein aerobic conditions are preferred.

Industrial Batch and Continuous Fermentations

A classical batch fermentation is a closed system where the composition of the medium is set at the beginning of the fermentation and not subject to artificial alterations during the fermentation. Thus, at the beginning of the fermentation the medium is inoculated with the desired organism or organisms, and fermentation is permitted to occur without adding anything to the system. Typically, a "batch" fermentation is batch with respect to the addition of carbon source and attempts are often made at controlling factors such as pH and oxygen concentration. In batch systems the metabolite and biomass compositions of the system change constantly up to the time the fermentation is stopped. Within batch cultures cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the Fed-Batch system. Fed-Batch fermentation processes are also suitable in the present invention and comprise a typical batch system with the exception that the substrate is added in increments as the fermentation progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch fermentations are common and well known in the art and examples may be found in Thomas D. Brock in *Biotechnology: A Textbook of Industrial Microbiology*, Second Edition (1989) Sinauer Associates, Inc., Sunderland, Mass. (hereinafter "Brock"), or Deshpande, Mukund V., *Appl. Biochem. Biotechnol.*, 36:227, (1992).

Although the present invention is performed in batch mode it is contemplated that the method would be adaptable to continuous fermentation methods. Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to the medium being drawn off must be balanced against the cell growth rate in the fermentation.

Methods of modulating nutrients and growth factors for continuous fermentation processes as well as techniques for maximizing the rate of product formation are well known in the art of industrial microbiology and a variety of methods are detailed by Brock, supra.

It is contemplated that the present invention may be practiced using either batch, fed-batch or continuous processes and that any known mode of fermentation would be suitable.

Applicants specifically incorporate the entire contents of all cited references in this disclosure. Further, when an amount, concentration, or other value or parameter is given either as a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations used is as follows: "min" means minute(s), "h" means hour(s), "µL" means microliter(s), "mL" means milliliter(s), "L" means liter(s), "nm" means nanometer(s), "mm" means millimeter(s), "cm" means centimeter(s), "µm" means micrometer(s), "mM" means millimolar, "M" means molar, "mmol" means millimole(s), "µmole" means micromole(s), "pmol" means picomole(s), "g" means gram(s), "µg" means microgram(s), "mg" means milligram(s), "g" means the gravitation constant, "rpm" means revolutions per minute, "DTT" means dithiothreitol, and "cat#" means catalog number.

General Methods:

Standard recombinant DNA and molecular cloning techniques used in the Examples are well known in the art and are described by Maniatis, (supra); Silhavy et al., (supra); and Ausubel et al., (supra).

Materials and methods suitable for the maintenance and growth of bacterial cultures are also well known in the art. Techniques suitable for use in the following Examples may be found in *Manual of Methods for General Bacteriology*, Phillipp Gerhardt, R. G. E. Murray, Ralph N. Costilow, Eugene W. Nester, Willis A. Wood, Noel R. Krieg and G. Briggs Phillips, eds., American Society for Microbiology, Washington, D.C., 1994, or in Brock (supra). All reagents, restriction enzymes and materials used for the growth and maintenance of bacterial cells were obtained from BD Diagnostic Systems (Sparks, Md.), Invitrogen (Carlsbad, Calif.), Life Technologies (Rockville, Md.), QIAGEN (Valencia, Calif.) or Sigma-Aldrich Chemical Company (St. Louis, Mo.), unless otherwise specified.

Example 1

Preparation of Plasmid pLX121 for Evaluating Inclusion Body Tag Performance

A genetic construct was prepared for evaluating the performance of the present inclusion body tags when fused to a soluble peptide of interest. The peptide of interest used in the present examples was prepared from a previously reported peptide-based triblock dispersant (U.S. Ser. No. 10/935,254).

Cloning of the TBP1 Gene

The TBP1 gene, encoding the TBP1 peptide, was selected for evaluation of the present inclusion body tags. The synthetic TBP1 peptide is peptide-based triblock dispersant comprising a carbon-black binding domain, a hydrophilic peptide linker, and a cellulose binding domain (see Example 15 of U.S. patent application Ser. No. 10/935,254, herein incorporated by reference).

The TBP1 gene (SEQ ID NO: 3) encoding the 68 amino acid peptide TBP101 (SEQ ID NO: 4) was assembled from synthetic oligonucleotides (Sigma-Genosys, Woodlands, Tex.; Table 1).

TABLE 1

Oligonucleotides Used to Prepare the TBP1

| Oligonucleotide Name | Nucleotide Sequence (5'-3') | SEQ ID NO: |
|---|---|---|
| TBP1(+)1 | GGATCCATCGAAGGTCGTTTCCACGAA AACTGGCCGTCTGGTGGCGGTACCTC TACTTCCAAAGCTTCCACCACTACGAC TTCTAGCAAAACCACCACTACAT | 5 |
| TBP1(+)2 | CCTCTAAGACTACCACGACTACCTCCAA AACCTCTACTACCTCTAGCTCCTCTACG GGCGGTGGCACTCACAAGACCTCTACTC AGCGTCTGCTGGCTGCATAA | 6 |
| TBP1(-)1 | TTATGCAGCCAGCAGACGCTGAGTAGAG GTCTTGTGAGTGCCACCGCCCGTAGAG GAGCTAGAGGTAGT | 7 |
| TBP1(-)2 | AGAGGTTTTGGAGGTAGTCGTGGTAGTC TTAGAGGATGTAGTGGTGGTTTTGCTAG AAGTCGTAGTGGT | 8 |
| TBP1(-)3 | GGAAGCTTTGGAAGTAGAGGTACCGC CACCAGACGGCCAGTTTTCGTGGAAAC GAGCTTCGATGGATCC | 9 |

Each oligonucleotide was phosphorylated with ATP using T4 polynucleotide kinase. The resulting oligonucleotides were mixed, boiled for 5 min, and then cooled to room temperature slowly. Finally, the annealed oligonucleotides were ligated with T4 DNA ligase to give synthetic DNA fragment TBP1, given as SEQ ID NO: 3.

Construction of pINK101 Expression Plasmid:

Lambda phage site-specific recombination was used for preparation and expression of the present fusion proteins (Gateway™ System; Invitrogen, Carlsbad, Calif.). TBP1 was integrated into the Gateway™ system for protein over-expression. In the first step, 2 μL of the TBP1 ligation mixture was used in a 50-μL PCR reaction. Reactions were catalyzed by pfu DNA polymerase (Stratagene, La Jolla, Calif.), following the standard PCR protocol. Primer 5'TBP1 (5'-CAC-CGGATCCATCGAAGGTCGT-3'; SEQ ID NO: 10) and 3'TBP1 (5'-TCATTATGCAGCCAGCAGCGC-3'; SEQ ID NO: 11) were used for amplification of the TBP1 fragment. Due to the design of these primers, an additional sequence of CACC and another stop codon TGA were added to the 5' and 3' ends of the amplified fragments.

The amplified TBP1 was directly cloned into pENTR™/D-TOPO® vector (SEQ ID NO: 12) using Invitrogen's pENTR™ directional TOPO® cloning kit (Invitrogen; Catalog K2400-20), resulting in the Gateway™ entry plasmid pENTR-TBP1. This entry plasmid was propagated in One Shot® TOP10 E. coli cells (Invitrogen). The accuracy of the PCR amplification and cloning procedures were confirmed by DNA sequencing analysis. The entry plasmid was mixed with pDEST17 (Invitrogen, SEQ ID NO: 13). LR recombination reactions were catalyzed by LR Clonase™ (Invitrogen). The destination plasmid, pINK101 was constructed and propagated in the DH5α E. coli strain. The accuracy of the recombination reaction was determined by DNA sequencing. All reagents for LR recombination reactions (i.e., lambda phage site-specific recombination) were provided in Invitrogen's E. coli expression system with the Gateway™ Technology kit. The site-specific recombination process followed the manufacturer's instructions (Invitrogen).

The resulting plasmid, named pINK101, contains the coding regions for recombinant protein 6H-TBP1, named INK101 (SEQ ID NOs 14 and 15), which is an 11.6 kDa protein. The protein sequence includes a 6× His tag and a 24 amino acid linker that includes Factor Xa protease recognition site before the sequence of the TBP101 peptide.

The amino acid coding region for the 6× His tag and the following linker comprising the Factor Xa protease recognition site were excised from pINK101 by digestion with the NdeI and BamHI restriction enzymes.

The TBP1 gene (SEQ ID NO: 3) encodes a polypeptide (SEQ ID NO: 4) having a ST linker flanked by Gly-Gly-Gly amino acids. The system was made more modular by further mutagenesis to change the upstream amino acid sequence from Gly-Gly-Gly to Ala-Gly-Gly (codon GGT changed to GCC) and the downstream Gly-Gly-Gly to Gly-Gly-Ala (codon GGT GGC changed to GGC GCC). These changes provided a NgoMI restriction site and a KasI restriction site flanking the ST linker, thus facilitating replacement of any element in TBP1.

Further modifications were made to TBP101 including the addition of an acid cleavable site to facilitate the removal of any tag sequence encoded by the region between the NdeI and BamHI sites of the expression plasmid. The resulting plasmid was called pLX121 (also referred to as "pINK101 DP"; SEQ ID NO: 16). These modifications changed the amino acids E-G to D-P (acid cleavable aspartic acid—proline linkage) using the Stratagene QuikChange® II Site-Directed Mutagenesis Kit Cat# 200523 (La Jolla, Calif.) as per the manufacturer's protocol using the primers INK101+ (5'-CCCCTTCACCGGATCCATCGATC-CACGTTTCCACGAAAACTGGCC-3'; SEQ ID 17) and INK101− (5'-GGCCAGTTTTCGTGGAAACGTGGATC-GATGGATCCGGTGMGGGG-3'; SEQ ID NO 18). The sequences were confirmed by DNA sequence analysis. The coding region and the corresponding amino acid sequence of the modified protein, INK101DP, is provided as SEQ ID NOs 19 and 20, respectively. INK101DP (also referred to herein as "TBP101 DP") was used to evaluate the present inclusion body tags.

INK101DP Peptide (SEQ ID NO: 20)
MSYYHHHHHHLESTSLYKKAGSAAAPFTGSIDPRFHENWPSAGGTSTS

KASTTTTSSKTTTTSSKTTTTTSKTSTTSSSSTGGATHKTSTQRLLAA

The aspartic acid—proline acid cleavable linker is bolded. The DP moiety replaces the EG moiety found in the unmodified TBP101 peptide (SEQ ID, NO: 4). The modified TBP101 peptide is underlined.

Example 2

Generation of Zein-based Inclusion Body Tag Library

Several series of inclusion body tag libraries were generated from the *Zea mays* zein storage protein (GenBank® Accession No. AAP32017; SEQ ID NO: 2 encoded by the coding sequence as represented by SEQ ID NO:1). Three series of putative inclusion body tags (typically 15 amino acids in length; one being only 13 amino acids in length) were prepared from 15 amino acid segments of the zein protein. Library series #1 (IBTs 65-79) was prepared by creating a set of 15 amino acid long peptides (IBT-79 is only 13 amino acids in length) from consecutive sequences spanning the entire length of the zein protein starting with amino acid residue position 1 of SEQ ID NO: 2 (i.e. IBT–65=amino acid residues 1-15 of SEQ ID NO: 2, IBT–66=amino acid residues 16-30 of SEQ ID NO: 2, etc.). Library series #2 (IBTs 80-121) was prepared in a similar fashion, except that the first member of the library series started with amino acid residue position 6 of SEQ ID NO: 2. Library series #3 (IBTs 122-135) was also prepared in a similar fashion starting at amino acid position 11 of SEQ ID NO: 2. In this way, an overlapping library 13-15 amino acid long peptides were prepared that spanned the entire length of zein protein (Table 2).

Based on the expression ranking data (i.e. the ability of the inclusion body tag to induce insoluble fusion protein when fused to a normally soluble peptide of interest; see Example 3), several additional inclusion body tags (IBTs 158-159) of varying length were prepared from regions of the zein protein suitable for use as inclusion body tags (Table 2).

Synthesis and Cloning Procedure for Preparing Inclusion Body Tags

The inclusion body tags were assembled from two complementary synthetic *E. coli* biased oligonucleotides (Sigma Genosys). Overhangs were included in each oligonucleotide to generate cohesive ends compatible with the restriction sites NdeI and BamHI.

The oligonucleotides (Table 2) were annealed by combining 100 pmol of each oligonucleotide in deionized water into one tube and heated in a water bath set at 99° C. for 10 minutes after which the water bath was turned off. The oligonucleotides were allowed to anneal slowly until the water bath reached room temperature (20-25° C.). The annealed oligonucleotides were diluted in 100 μL water prior to ligation into the test vector. The vector pLX121 (SEQ ID NO: 16) comprises the open reading frame encoding the INK101DP peptide (SEQ ID NO: 20). The vector was digested in Buffer 2 (New England Biolabs, Beverly, Mass.) comprising 10 mM Tris-HCl, 10 mM MgCl$_2$, 50 mM NaCl, 1 mM dithiothreitol (DTT); pH ~7.9) with the NdeI and BamHI restriction enzymes to release a 90 bp fragment corresponding to the original His6 containing inclusion body fusion partner and the linker from the parental pDEST17 plasmid that includes the att site of the Gateway™ Cloning System. The NdeI-BamHI fragments from the digested plasmid were separated by agarose gel electrophoresis and the vector was purified from the gel by using Qiagen QIAquick® Gel Extraction Kit (QIAGEN Valencia, Calif.; cat# 28704).

The diluted and annealed oligonucleotides (approximately 0.2 pmol) were ligated with T4 DNA Ligase (New England Biolabs Beverly, Mass.; catalog # M0202) to NdeI-BamHI digested, gel purified, plasmid pLX121 (approximately 50 ng) at 12° C. for 18 hours. DNA sequence analysis confirmed the expected plasmid sequence.

TABLE 2

Oligonucleotide Sequences Used to Prepare the Various Inclusion Body Tags (IBTs)

| Inclusion Body Tag | DNA strand | Oligonucleotide (SEQ ID NO.) | IBT Amino Acid Sequence (SEQ ID NO.) | Amino Acid Residue Positions of the Zein Protein (SEQ ID NO: 2) |
|---|---|---|---|---|
| IBT-65 | + | 21 | 111 | 1-15 |
| IBT-65 | − | 22 | | |
| IBT-66 | + | 23 | 112 | 16-30 |
| IBT-66 | − | 24 | | |
| IBT-67 | + | 25 | 113 | 31-45 |
| IBT-67 | − | 26 | | |
| IBT-68 | + | 27 | 114 | 46-60 |
| IBT-68 | − | 28 | | |
| IBT-69 | + | 29 | 115 | 61-75 |
| IBT-69 | − | 30 | | |
| IBT-70 | + | 31 | 116 | 76-90 |
| IBT-70 | − | 32 | | |
| IBT-71 | + | 33 | 117 | 91-105 |
| IBT-71 | − | 34 | | |
| IBT-72 | + | 35 | 118 | 106-120 |
| IBT-72 | − | 36 | | |
| IBT-73 | + | 37 | 119 | 121-135 |
| IBT-73 | − | 38 | | |
| IBT-74 | + | 39 | 120 | 136-150 |
| IBT-74 | − | 40 | | |
| IBT-75 | + | 41 | 121 | 151-165 |
| IBT-75 | − | 42 | | |
| IBT-76 | + | 43 | 122 | 166-180 |
| IBT-76 | − | 44 | | |
| IBT-77 | + | 45 | 123 | 181-195 |
| IBT-77 | − | 46 | | |
| IBT-78 | + | 47 | 124 | 196-210 |
| IBT-78 | − | 48 | | |
| IBT-79 | + | 49 | 125[a] | 211-223[a] |
| IBT-79 | − | 50 | | |
| IBT-108 | + | 51 | 126 | 6-20 |
| IBT-108 | − | 52 | | |
| IBT-109 | + | 53 | 127 | 21-35 |
| IBT-109 | − | 54 | | |
| IBT-110 | + | 55 | 128 | 36-50 |
| IBT-110 | − | 56 | | |
| IBT-111 | + | 57 | 129 | 51-65 |
| IBT-111 | − | 58 | | |
| IBT-112 | + | 59 | 130 | 66-80 |
| IBT-112 | − | 60 | | |
| IBT-113 | + | 61 | 131 | 81-95 |
| IBT-113 | − | 62 | | |
| IBT-114 | + | 63 | 132 | 96-110 |
| IBT-114 | − | 64 | | |
| IBT-115 | + | 65 | 133 | 111-125 |
| IBT-115 | − | 66 | | |
| IBT-116 | + | 67 | 134 | 126-140 |
| IBT-116 | − | 68 | | |
| IBT-117 | + | 69 | 135 | 141-155 |
| IBT-117 | − | 70 | | |
| IBT-118 | + | 71 | 136 | 156-170 |
| IBT-118 | − | 72 | | |
| IBT-119 | + | 73 | 137 | 171-185 |
| IBT-119 | − | 74 | | |
| IBT-120 | + | 75 | 138 | 186-200 |
| IBT-120 | − | 76 | | |
| IBT-121 | + | 77 | 139 | 201-215 |
| IBT-121 | − | 78 | | |
| IBT-122 | + | 79 | 140 | 11-25 |
| IBT-122 | − | 80 | | |
| IBT-123 | + | 81 | 141 | 26-40 |
| IBT-123 | − | 82 | | |

TABLE 2-continued

Oligonucleotide Sequences Used to Prepare the Various Inclusion Body Tags (IBTs)

| Inclusion Body Tag | DNA strand | Oligonucleotide (SEQ ID NO.) | IBT Amino Acid Sequence (SEQ ID NO.) | Amino Acid Residue Positions of the Zein Protein (SEQ ID NO: 2) |
|---|---|---|---|---|
| IBT-124 | + | 83 | 142 | 41-55 |
| IBT-124 | − | 84 | | |
| IBT-125 | + | 85 | 143 | 56-70 |
| IBT-125 | − | 86 | | |
| IBT-126 | + | 87 | 144 | 71-85 |
| IBT-126 | − | 88 | | |
| IBT-127 | + | 89 | 145 | 86-100 |
| IBT-127 | − | 90 | | |
| IBT-128 | + | 91 | 146 | 101-115 |
| IBT-128 | − | 92 | | |
| IBT-129 | + | 93 | 147 | 116-130 |
| IBT-129 | − | 94 | | |
| IBT-130 | + | 95 | 148 | 131-145 |
| IBT-130 | − | 96 | | |
| IBT-131 | + | 97 | 149 | 146-160 |
| IBT-131 | − | 98 | | |
| IBT-132 | + | 99 | 150 | 161-175 |
| IBT-132 | − | 100 | | |
| IBT-133 | + | 101 | 151 | 176-190 |
| IBT-133 | − | 102 | | |
| IBT-134 | + | 103 | 152 | 191-205 |
| IBT-134 | − | 104 | | |
| IBT-135 | + | 105 | 153 | 206-220 |
| IBT-135 | − | 106 | | |
| IBT-158 | + | 107 | 154 | 86-110 |
| IBT-158 | − | 108 | | |
| IBT-159 | + | 109 | 155 | 91-110 |
| IBT-159 | − | 110 | | |

$^a$IBT-79 is 13 amino acids in length.

The resulting expression vectors were individually transformed into the arabinose inducible expression strain *E. coli* BL21-AI (Invitrogen; cat# C6070-03).

Transformation and Expression

Each expression vector was individually transferred into BL21-AI chemically competent *E. coli* cells for expression analysis. To produce the recombinant protein, 3 mL of LB-ampicillin broth (10 g/L bacto-tryptone, 5 g/L bacto-yeast extract, 10 g/L NaCl, 100 mg/L ampicillin; pH 7.0) was inoculated with one colony of the transformed bacteria and the culture was shaken at 37° C. until the OD$_{600}$ reached 0.6. Expression was induced by adding 0.03 mL of 20% L-arabinose (final concentration 0.2%, Sigma-Aldrich, St. Louis, Mo.) to the culture and shaking was continued for another 3 hours. For whole cell analysis, 0.1 OD$_{600}$ mL of cells were collected, pelleted, and 0.06 mL SDS PAGE sample buffer (1×LDS Sample Buffer (Invitrogen cat# NP0007), 6 M urea, 100 mM DTT) was added directly to the whole cells. The samples were heated at 99° C. for 10 minutes to solubilize the proteins. The solubilized proteins were then loaded onto 4-12% gradient MES NuPAGE® gels (NuPAGE® gels cat #NP0322, MES Buffer cat# NP0002; Invitrogen) and visualized with a Coomassie® G-250 stain (SimplyBlue™ SafeStain; Invitrogen; cat# LC6060).

Example 3

Verification of Inclusion Body Formation

To verify that the fusion partner drove expression into insoluble inclusion bodies, it was necessary to lyse the collected cells (0.1 OD$_{600}$ mL of cells) and fractionate the insoluble from the soluble fraction by centrifugation. Cells were lysed using CelLytic™ Express (Sigma, St. Louis, Mo. cat# C-1990) according to the manufacturer's instructions. Cells that do not produce inclusion bodies undergo complete lysis and yielded a clear solution. Cells expressing inclusion bodies appeared turbid even after complete lysis.

The method used to rank all inclusion body tags was a subjective visual inspection of SimplyBlue™ SafeStain stained PAGE gels. The scoring system was 0, 1, 2 or 3. If no band is detected then a zero score is given. A score of three is given to very heavily stained wide expressed bands. Bands that are weak are scored a one and moderate bands are scored a two. Any score above zero indicated the presence of inclusion bodies (Table 4). Every amino acid has up to three opportunities to be in a tag. Except for the extreme C— and N-terminals of the scanned protein, there are scores per amino acid. These scores are added to give a final activity score for an individual amino acid.

Soluble and insoluble fractions were separated by centrifugation and analyzed by polyacrylamide gel electrophoresis and visualized with SimplyBlue™ SafeStain. Analysis of the cell protein by polyacrylamide gel electrophoresis was used to detect the production of the fusion protein in the whole cell and insoluble fractions but not the soluble cell fraction. Several fusion proteins comprising a 15 amino acid long inclusion body tag derived from amino acid residues 76-175 of SEQ ID NO: 2 were found to be insoluble. This result suggested that it was possible to have very small fusion partners (at least 15 amino acids in length) to facilitate production of peptides in inclusion bodies (Table 4)

TABLE 3

Fusion Protein Sequences

| Fusion Protein | Expression Plasmid Designation | Fusion Protein Nucleic acid Sequence (SEQ ID NO.) | Fusion Protein Amino Acid Sequence (SEQ ID NO.) |
|---|---|---|---|
| IBT 65-TBP101 | pLX240 | 156 | 157 |
| IBT 66-TBP101 | pLX257 | 158 | 159 |
| IBT 67-TBP101 | pLX276 | 160 | 161 |
| IBT 68-TBP101 | pLX242 | 162 | 163 |
| IBT 69-TBP101 | pLX247 | 164 | 165 |
| IBT 70-TBP101 | pLX277 | 166 | 167 |
| IBT 71-TBP101 | pLX241 | 168 | 169 |
| IBT 72-TBP101 | pLX258 | 170 | 171 |
| IBT 73-TBP101 | pLX259 | 172 | 173 |
| IBT 74-TBP101 | pLX260 | 174 | 175 |
| IBT 75-TBP101 | pLX250 | 176 | 177 |
| IBT 76-TBP101 | pLX248 | 178 | 179 |
| IBT 77-TBP101 | pLX244 | 180 | 181 |
| IBT 78-TBP101 | pLX278 | 182 | 183 |
| IBT 79-TBP101 | pLX249 | 184 | 185 |
| IBT 108-TBP101 | pLX266 | 186 | 187 |
| IBT 109-TBP101 | pLX267 | 188 | 189 |
| IBT 110-TBP101 | pLX268 | 190 | 191 |
| IBT 111-TBP101 | pLX269 | 192 | 193 |
| IBT 112-TBP101 | pLX270 | 194 | 195 |
| IBT 113-TBP101 | pLX271 | 196 | 197 |
| IBT 114-TBP101 | pLX272 | 198 | 199 |
| IBT 115-TBP101 | pLX273 | 200 | 201 |
| IBT 116-TBP101 | pLX274 | 202 | 203 |
| IBT 117-TBP101 | pLX275 | 204 | 205 |
| IBT 118-TBP101 | pLX299 | 206 | 207 |
| IBT 119-TBP101 | pLX300 | 208 | 209 |
| IBT 120-TBP101 | pLX301 | 210 | 211 |
| IBT 121-TBP101 | pLX302 | 212 | 213 |
| IBT 122-TBP101 | pLX303 | 214 | 215 |
| IBT 123-TBP101 | pLX304 | 216 | 217 |
| IBT 124-TBP101 | pLX305 | 218 | 219 |
| IBT 125-TBP101 | pLX306 | 220 | 221 |
| IBT 126-TBP101 | pLX307 | 222 | 223 |

TABLE 3-continued

Fusion Protein Sequences

| Fusion Protein | Expression Plasmid Designation | Fusion Protein Nucleic acid Sequence (SEQ ID NO.) | Fusion Protein Amino Acid Sequence (SEQ ID NO.) |
|---|---|---|---|
| IBT 127-TBP101 | pLX319 | 224 | 225 |
| IBT 128-TBP101 | pLX308 | 226 | 227 |
| IBT 129-TBP101 | pLX235 | 228 | 229 |
| IBT 130-TBP101 | pLX309 | 230 | 231 |
| IBT 131-TBP101 | pLX320 | 232 | 233 |
| IBT 132-TBP101 | pLX310 | 234 | 235 |
| IBT 133-TBP101 | pLX311 | 236 | 237 |
| IBT 134-TBP101 | pLX312 | 238 | 239 |
| IBT 135-TBP101 | pLX321 | 240 | 241 |
| IBT 158-TBP101 | pLX343 | 242 | 243 |
| IBT 159-TBP101 | pLX344 | 244 | 245 |

TABLE 4

Inclusion Body Tag Expression Ranking

| IBT Designation | Zein-based Inclusion Body Tag Amino Acid Sequence (SEQ ID NO:) | Expression Ranking |
|---|---|---|
| IBT 65 | MRVLLVALALLALAA (SEQ ID NO: 111) | 0 |
| IBT 66 | SATSTHTSGGCGCQP (SEQ ID NO: 112) | 0 |
| IBT 67 | PPPVHLPPPVHLPPP (SEQ ID NO: 113) | 0 |
| IBT 68 | VHLPPPVHLPPPVHL (SEQ ID NO: 114) | 0 |
| IBT 69 | PPPVHLPPPVHVPPP (SEQ ID NO: 115) | 0 |
| IBT 70 | VHLPPPPCHYPTQ (SEQ ID NO: 116) | 2 |
| IBT 71 | RPQPHPQPHPCPCQQ (SEQ ID NO: 117) | 3 |
| IBT 72 | PHPSPCQLQGTCGVG (SEQ ID NO: 118) | 0 |
| IBT 73 | STPILGQCVEFLRHQ (SEQ ID NO: 119) | 2 |
| IBT 74 | CSPTATPYCSPQCQS (SEQ ID NO: 120) | 0 |
| IBT 75 | LRQQCCQQLRQVEPQ (SEQ ID NO: 121) | 1 |
| IBT 76 | HRYQAIFGLVLQSIL (SEQ ID NO: 122) | 0 |
| IBT 77 | QQQPQSGQVAGLLAA (SEQ ID NO: 123) | 0 |
| IBT 78 | QIAQQLTAMCGLQQP (SEQ ID NO: 124) | 0 |
| IBT 79 | TPCPYAAAGGVPH (SEQ ID NO: 125) | 1 |
| IBT 108 | VALALLALAASATST (SEQ ID NO: 126) | 0 |
| IBT 109 | HTSGGCGCQPPPPVH (SEQ ID NO: 127) | 0 |
| IBT 110 | LPPPVHLPPPVHLPP (SEQ ID NO: 128) | 0 |
| IBT 111 | PVHLPPPVHLPPPVH (SEQ ID NO: 129) | 0 |
| IBT 112 | LPPPVHVPPPVHLPP (SEQ ID NO: 130) | 0 |
| IBT 113 | PPCHYPTQPPRPQPH (SEQ ID NO: 131) | 3 |
| IBT 114 | PQPHPCPCQQPHPSP (SEQ ID NO: 132) | 2 |
| IBT 115 | CQLQGTCGVGSTPIL (SEQ ID NO: 133) | 1 |
| IBT 116 | GQCVEFLRHQCSPTA (SEQ ID NO: 134) | 0 |
| IBT 117 | TPYCSPQCQSLRQQC (SEQ ID NO: 135) | 1 |
| IBT 118 | CQQLRQVEPQHRYQA (SEQ ID NO: 136) | 0 |
| IBT 119 | IFGLVLQSILQQQPQ (SEQ ID NO: 137) | 0 |
| IBT 120 | SGQVAGLLAAQIAQQ (SEQ ID NO: 138) | 0 |
| IBT 121 | LTAMCGLQQPTPCPY (SEQ ID NO: 139) | 0 |
| IBT 122 | LALAASATSTHTSGG (SEQ ID NO: 140) | 0 |
| IBT 123 | CGCQPPPPVHLPPPV (SEQ ID NO: 141) | 0 |
| IBT 124 | HLPPPVHLPPPVHLP (SEQ ID NO: 142) | 0 |
| IBT 125 | PPVHLPPPVHLPPPV (SEQ ID NO: 143) | 0 |
| IBT 126 | HVPPPVHLPPPPCHY (SEQ ID NO: 144) | 0 |
| IBT 127 | PTQPPRPQPHPQPHP (SEQ ID NO: 145) | 3 |
| IBT 128 | CPCQQPHPSPCQLQG (SEQ ID NO: 146) | 0 |
| IBT 129 | TCGVGSTPILGQCVE (SEQ ID NO: 147) | 1 |
| IBT 130 | FLRHQCSPTATPYCS (SEQ ID NO: 148) | 3 |
| IBT 131 | PQCQSLRQQCCQQLR (SEQ ID NO: 149) | 2 |
| IBT 132 | QVEPQHRYQAIFGLV (SEQ ID NO: 150) | 1 |

TABLE 4-continued

Inclusion Body Tag Expression Ranking

| IBT Designation | Zein-based Inclusion Body Tag Amino Acid Sequence (SEQ ID NO:) | Expression Ranking |
|---|---|---|
| IBT 133 | LQSILQQQPQSGQVA (SEQ ID NO: 151) | 0 |
| IBT 134 | GLLAAQIAQQLTAMC (SEQ ID NO: 152) | 0 |
| IBT 135 | GLQQPTPCPYAAAGG (SEQ ID NO: 153) | 0 |
| IBT 158 | PTQPPRPQPHPQPHPCPCQQPHPSP (SEQ ID NO: 154) | 2 |
| IBT 159 | RPQPHPQPHPCPCQQPHPSP (SEQ ID NO: 155) | 2 |

Example 4

Synthesis, Cloning, and Evaluation of Fusion Peptides Comprising Inclusion Body Tags IBT-180 and IBT-181

The expression ranking data from the various inclusion body tags was evaluated and used to design two additional inclusion body tags (IBT-180 and IBT-181) comprising a T7 translational enhancer (MASMTGGQQMG; SEQ ID NO: 246) linked to the N-terminal portion of an inclusion body forming region of the zein protein. This sequence was provided to standardize the critical N-terminal translated sequence, which is known to be especially important in determining translation initiation efficiency (Stormo, G. "Translation Initiation" in Reznikov, W and Gold, L, *Maximizing Gene Expression Butterworths*, Boston, Mass. (1986) pp. 195-224.)

Design of Inclusion Body Tags IBT-180 and IBT-181

An alignment of the inclusion body tags exhibiting inclusion body forming ability was performed against the zein protein. The initial library of overlapping inclusion body tags was designed span the entire length of the zein protein. Based on the overlapping nature of the inclusion body tag library, every amino acid had up to three opportunities to be in a tag. Relative scores were assigned to each amino acid within the zein protein based on the frequency of occurrence within a peptide tag capable of inducing inclusion body formation. The relative scores were used to assign a final activity score for each amino acid. When activity score for each amino acid was plotted over the length of the scanned protein, a map was generated depicting the ability of certain domains on the scanned protein to induce inclusion body formation. From this assessment, it was determined that inclusion body tags prepared from the region of the zein protein encompassed by amino acid residues 76-175 of SEQ ID NO: 2 was particularly effective in inducing inclusion body formation.

A 100 amino acid long functional inclusion body tag, IBT-181 (SEQ ID NO: 248), comprising amino acid residues 76 to 175 of SEQ ID NO: 2 and a shorter 30 amino acid inclusion body tag, IBT-180 (SEQ ID NO: 247), comprising a subset of this region (amino acid residues 76 to 105 of SEQ ID NO: 2) were prepared. Both tags also included a short 11 amino acid T7 tag (a translational enhancer) (MASMTGGQQMG; SEQ ID NO: 246) added to the N-terminus of each tag.

Synthesis and Cloning Procedure of IBT-180 and IBT-181

The nucleic acid molecules encoding the inclusion body tags IBT-180 (SEQ ID NO: 247) and IBT-181 (SEQ ID NO: 248) were synthesized and delivered as plasmids harboring kanamycin resistance by DNA 2.0 Inc. (Menlo Park, Calif.). The nucleotide sequence encoding each inclusion body tag was flanked by NdeI and BamHI restriction sites.

The vector comprising the nucleic acid molecule encoding the IBT-180 tag was digested in Buffer 2 (New England Biolabs 10 mM Tris-HCl, 10 mM $MgCl_2$, 50 mM NaCl, 1 mM dithiothreitol; pH7.9) with the NdeI and BamHI restriction enzymes (New England Biolabs Beverly, Mass.). Likewise, the test system expression vector pLX121 (SEQ ID NO: 16) was digested with NdeI and BamHI as described in the previous examples. The IBT-180 inclusion body tag restriction digest was directly ligated to the NdeI/BamHI digested test expression vector pLX121 with T4 DNA Ligase (New England Biolabs Beverly, Mass. cat# M0202) at 12° C. for 18 hours. Ampicillin resistant colonies were sequenced. The sequence of the plasmid (pLX363) was confirmed. Expression plasmid pLX363 comprises the chimeric gene encoding the IBT 180-TBP101 fusion protein (SEQ ID NOs: 249 and 250), operably linked to an arabinose inducible promoter.

Inclusion body tag IBT-181 (SEQ ID BO: 248) was cloned using the same procedure as described for IBT-180, resulting in the expression plasmid pLX364. Expression plasmid pLX364 comprises the chimeric gene encoding the IBT 181-TBP101 fusion protein (SEQ ID NOs: 251 and 252), operably linked to an arabinose inducible promoter.

Transformation and Expression of IBT-180 and IBT-181

Expression plasmids pLX363 and pLX364 were transformed, expressed, and evaluated using the procedures described in Examples 2 and 3. The expression ranking results are provided in Table 5.

TABLE 5

Inclusion Body Tag Expression Ranking for IBT-180 and IBT-181

| IBT Designation | Zein-based Inclusion Body Tag Amino Acid Sequence (SEQ ID NO:) | Expression Ranking |
|---|---|---|
| IBT 180 | MASMTGGQQMGVHLPPPPCHYPTQPPRPQPHPQPHPCPCQQ (SEQ ID NO: 247) | 2 |
| IBT 181 | MASMTGGQQMGVHLPPPPCHYPTQPPRPQPHPQPHPCPCQQPHPSPCQLQGTCGVGSTPILGQCVEFLRHQCSPTATPYCSPQCQSLRQQCCQQLRQVEPQHRYQAIFGLV (SEQ ID NO: 248) | 2 |

What is claimed is:

1. An inclusion body tag consisting of 15 contiguous amino acids residues from amino acids residues 76 to 175 of SEQ ID NO: 2.

2. A fusion peptide comprising the inclusion body tag of claim 1 operably linked to at least one peptide of interest.

3. The fusion peptide of claim 2, further comprising at least one cleavable peptide linker having a cleavage site.

4. The fusion peptide of claim 2 wherein the peptide of interest is selected from the group consisting of a peptide that binds to a polymer, a peptide that binds to hair, a peptide that binds to nail, a peptide that binds to skin, a peptide that binds to an antimicrobial substance.

* * * * *

UNITED STATES PATENT AND TRADEMARK OFFICE
CERTIFICATE OF CORRECTION

PATENT NO. : 7,732,569 B2
APPLICATION NO. : 11/641936
DATED : June 8, 2010
INVENTOR(S) : Linda Jane Decarolis Page 1 of 1

It is certified that error appears in the above-identified patent and that said Letters Patent is hereby corrected as shown below:

Column 236, line 66, the word -- and -- should be inserted between "skin," and "a peptide that binds to an antimicrobial substance."

Signed and Sealed this

Seventeenth Day of August, 2010

David J. Kappos
*Director of the United States Patent and Trademark Office*